(12) United States Patent  (10) Patent No.: US 8,431,542 B2
Wang et al.  (45) Date of Patent: Apr. 30, 2013

(54) MICRORNAS THAT REGULATE MUSCLE CELL PROLIFERATION AND DIFFERENTIATION

(75) Inventors: Da-Zhi Wang, Chapel Hill, NC (US); Jianfu Chen, Chapel Hill, NC (US)

(73) Assignee: The University of North Carolina at Chapel Hill, Durham, NC (US)

( * ) Notice: Subject to any disclaimer, the term of this patent is extended or adjusted under 35 U.S.C. 154(b) by 609 days.

(21) Appl. No.: 12/086,109

(22) PCT Filed: Dec. 12, 2006

(86) PCT No.: PCT/US2006/047255
§ 371 (c)(1),
(2), (4) Date: Sep. 15, 2009

(87) PCT Pub. No.: WO2007/070483
PCT Pub. Date: Jun. 21, 2007

(65) Prior Publication Data
US 2010/0292297 A1 Nov. 18, 2010

Related U.S. Application Data

(60) Provisional application No. 60/749,544, filed on Dec. 12, 2005.

(51) Int. Cl.
*C12N 15/11* (2006.01)
(52) U.S. Cl.
USPC .................................................. 514/44 A
(58) Field of Classification Search .............. 514/44 A
See application file for complete search history.

(56) References Cited

U.S. PATENT DOCUMENTS

| 2004/0157790 | A1 | 8/2004 | Herweijer et al. |
| 2004/0242528 | A1 | 12/2004 | Hagstrom et al. |
| 2005/0059005 | A1 | 3/2005 | Tuschl et al. |
| 2005/0124566 | A1 | 6/2005 | Robin et al. |
| 2006/0246491 | A1* | 11/2006 | Srivastava ..................... 435/6 |
| 2009/0176723 | A1* | 7/2009 | Brown et al. ................ 514/44 |

FOREIGN PATENT DOCUMENTS

| CA | 2515586 | 9/2004 |
| CA | 2603881 | 10/2006 |
| EP | 1 969 125 | 6/2012 |
| KR | 10-2008-0080177 | 9/2008 |
| MX | 286931 | 9/2010 |
| NZ | 569738 | 7/2012 |
| WO | WO 2004/076622 | 9/2004 |
| WO | WO 2006/107826 | 10/2006 |

OTHER PUBLICATIONS

Office Communication corresponding to Mexican Patent Application No. MX/a/2008/007552 dated Oct. 25, 2009.
Ambros, "The functions of animal microRNAs," Nature, vol. 431, pp. 350-355 (2004).
Bartel, "MicroRNAs: genomics, biogenesis, mechanism, and function," Cell, vol. 116, pp. 281-297 (2004).

(Continued)

*Primary Examiner* — Jon E Angell
(74) *Attorney, Agent, or Firm* — Jenkins, Wilson, Taylor & Hunt, P.A.

(57) ABSTRACT

The presently disclosed subject matter provides methods and compositions for modulating gene expression in myocytes. Also provided are cells comprising the compositions of the presently disclosed subject matter.

20 Claims, 30 Drawing Sheets

OTHER PUBLICATIONS

Bernstein et al., "Dicer is essential for mouse development," Nat. Genet., vol. 35, pp. 215-217 (2003).
Bracht et al., "Trans-splicing and polyadenylation of let-7 microRNA primary transcripts," RNA, vol. 10, pp. 1586-1594 (2004).
Chang et al., "MicroRNAs act sequentially and asymmetrically to control chemosensory laterality in the nematode," Nature, vol. 430, pp. 785-789 (2004).
Chen et al., "MicroRNAs modulate hematopoietic lineage differentiation," Science, vol. 303, pp. 83-86 (2004).
Giraldez et al., "MicroRNAs regulate brain morphogenesis in zebrafish," Science, vol. 308, pp. 833-838 (2005).
Harfe et al., "The RNaseIII enzyme Dicer is required for morphogenesis but not patterning of the vertebrate limb," Proc. Nat'l Acad. Sci. U S A. (2005).
He et al., "A microRNA polycistron as a potential human oncogene," Nature, vol. 435, pp. 828-833 (2005).
Heanue et al., "Synergistic regulation of vertebrate muscle development by Dach2, Eya2, and Six1, homologs of genes required for *Drosophila* eye formation," Genes Dev., vol. 13, pp. 3231-3243 (1999).
Hutvagner et al., "A cellular function for the RNA-interference enzyme Dicer in the maturation of the let-7 small temporal RNA," Science, vol. 293, pp. 834-838 (2001).
John et al., "Human MicroRNA targets," PLoS Biol 2, e363 (2004).
Johnston et al., "A microRNA controlling left/right neuronal asymmetry in *Caenorhabditis elegans*," Nature, vol. 426, pp. 845-849 (2003).
Jones et al., "Ablation of the murine alpha myosin heavy chain gene leads to dosage effects and functional deficits in the heart," J. Clin. Invest., vol. 98, pp. 1906-1917 (1996).
Ketting et al., "Dicer functions in RNA interference and in synthesis of small RNA involved in developmental timing in *C. elegans*," Genes Dev., vol. 15, pp. 2654-2659 (2001).
Kiriakidou et al., "A combined computational-experimental approach predicts human microRNA targets," Genes Dev., vol. 18, pp. 1165-1178 (2004).
Krek et al., "Combinatorial microRNA target predictions," Nat. Genet., vol. 37, pp. 495-500 (2005).
Lee et al., "The *C. elegans* heterochronic gene lin-4 encodes small RNAs with antisense complementarity to lin-14," Cell, vol. 75, pp. 843-854 (1993).
Lee et al., "MicroRNA genes are transcribed by RNA polymerase II," Embo. J., vol. 23, pp. 4051-4060 (2004).
Lewis et al., "Prediction of mammalian microRNA targets," Cell, vol. 115, (2003). pp. 787-798 (2003).
Li et al., "Requirement for serum response factor for skeletal muscle growth and maturation revealed by tissue-specific gene deletion in mice," Proc. Nat'l Acad. Sci. USA, vol. 102, pp. 1082-1087 (2005).
Mansfield et al., "MicroRNA-responsive 'sensor' transgenes uncover Hox-like and other developmentally regulated patterns of vertebrate microRNA expression," Nat. Genet., vol. 36, pp. 1079-1083 (2004).
Office Communication corresponding to Mexican Patent Application No. MX/a/2008/007552 dated Feb. 25, 2009.
Poy et al., "A pancreatic islet-specific microRNA regulates insulin secretion," Nature, vol. 432, pp. 226-230 (2004).
Rajewsky et al., "Computational identification of microRNA targets," Dev. Biol., vol. 267, pp. 529-535 (2004).
Soulez et al., "Growth and differentiation of C2 myogenic cells are dependent on serum response factor," Mol. Cell Biol., vol. 16, pp. 6065-6074 (1996).
Thomson et al., "A custom microarray platform for analysis of microRNA gene expression," Nat. Methods, vol. 1, pp. 47-53 (2004).
Wang et al., "Regulation of cardiac growth and development by SRF and its cofactors," Cold Spring Harb. Symp. Quant. Biol., vol. 67, pp. 97-105 (2002).
Wienholds et al., "MicroRNA expression in zebrafish embryonic development," Science, vol. 309, pp. 310-311 (2005).
Wightman et al., "Posttranscriptional regulation of the heterochronic gene lin-14 by lin-4 mediates temporal pattern formation in *C. elegans*," Cell, vol. 75, pp. 855-862 (Dec. 3, 1993).
Xu et al., "Murine protein kinase CK2α: cDNA and genomic cloning and chromosomal mapping," Genomics, vol. 48, pp. 79-86 (1998).
Yekta et al., "MicroRNA-directed cleavage of HOXB8 mRNA," Science, vol. 304, pp. 594-596 (2004).
Zhao et al., "Serum response factor regulates a muscle-specific microRNA that targets Hand2 during cardiogenesis," Nature, vol. 436, pp. 214-220 (2005).
Notification of Publication corresponding to Hong Kong Patent Application No. 09102539.5 dated Jun. 22, 2009.
Decision to Grant a European Patent corresponding to European Patent Application No. 06845222.6-1212/1969125 dated May 18, 2012.
Basyuk et al., "Human let-7 stem-loop precursors harbor features of RNase III cleavage products," Nucleic Acids Res., vol. 31, pp. 6593-6597 (2003).
Bohnsack et al., "Exportin 5 is a RanGTP-dependent dsRNA-binding protein that mediates nuclear export of pre-miRNAs," RNA, vol. 10, pp. 185-191 (2004).
Borsani et al., "EYA4, a novel vertebrate gene related to *Drosophila* eyes absent," Hum. Mol. Genet., vol. 8, pp. 11-23 (1999).
Brown et al., "Tbx5 and Tbx20 act synergistically to control vertebrate heart morphogenesis," Development, vol. 132, pp. 553-563 (2005).
Cao et al., "Modulation of smooth muscle gene expression by association of histone acetyltransferases and deacetylases with myocardin," Mol. Cell Biol., vol. 25, pp. 364-376 (2005).
Chen et al., "The Role of Microrna-1 and Microrna-133 in Skeletal Muscle Proliferation and Differentiation," Nature Genetics, vol. 38, No. 2, pp. 228-233 (Feb. 1, 2006).
Communication pursuant to Article 94(3) EPC corresponding to European Patent Application No. 06 845 222.6-1212 dated Jul. 12, 2011.
Conlon et al., "Inhibition of Xbra transcription activation causes defects in mesodermal patterning and reveals autoregulation of Xbra in dorsal mesoderm," Development, vol. 122, pp. 2427-2435 (1996).
Cotta-de-Almeida et al., "A new method for rapidly generating gene targeting vectors by engineering BACs through homologous recombination in bacteria," Genome Res., vol. 13, 2190-2194 (2003).
Czubryt et al., "Regulation of peroxisome proliferator-activated receptor gamma coactivator 1 alpha (PGC-1 alpha) and mitochondrial' function by MEF2 and HDAC5," Proc. Natl. Acad. Sci. USA, vol. 100, pp. 1711-1716 (2003).
Darling et al., "Different dimerization activities of alpha and beta thyroid hormone receptor isoforms," J. Biol. Chem., vol. 268, 10221-10227 (1993).
Doench and Sharp, "Specificity of microRNA target selection in translational repression," Genes Dev., vol. 18, pp. 504-511 (2004).
Ebel et al. (1992). Very stable mismatch duplexes: structural and thermodynamic studies on tandem G.A mismatches in DNA. Biochem 31:12083-1208.
Esau et al., "MicroRNA-143 regulates adipocyte differentiation," J. Biol. Chem., vol. 279, pp. 52361-52365 (2004).
Everett et al. "Regulation of myosin synthesis by thyroid hormone: relative change in the alpha- and beta-myosin heavy chain mRNA levels in rabbit heart," Biochemistry, vol. 23, pp. 1596-1599 (1984).
Examination Report corresponding to Australian Patent Application No. 2006326517 dated May 16, 2011.
Examination Report corresponding to New Zealand Patent Application No. 569738 dated Apr. 13, 2010.
Examination Report corresponding to New Zealand Patent Application No. 569738 dated Oct. 19, 2011.
Fondell et al., "Ligand induction of a transcriptionally active thyroid hormone receptor coactivator complex," Proc. Natl. Acad. Sci. USA, vol. 93, pp. 8329-8333 (1996).
Freier et al., "Improved free-energy parameters for predictions of RNA duplex stability," Proc. Natl. Acad. Sci. USA, vol. 83, pp. 9373-9377 (1986). <saved to server>.
Granzier and Labeit, "The giant protein titin: a major player in myocardial mechanics, signaling, and disease," Circ. Res., vol. 94, 284-295 (2004).
Griffiths-Jones, S., "The microRNA Registry," NAR, vol. 32, Database Issue, pp. D109-D111 (2004).

Grishok et al., "Genes and mechanisms related to RNA interference regulate expression of the small temporal RNAs that control C. elegans developmental timing," Cell, vol. 106, pp. 23-34 (2001).

Gustafson et al., "Thyroid hormone regulates expression of a transfected alpha-myosin heavy-chain fusion gene in fetal heart cells," Proc. Natl. Acad. Sci. USA, vol. 84, pp. 3122-3126 (1987).

Gwizdek et al., "Minihelix-containing RNAs mediate exportin-5-dependent nuclear export of the double-stranded RNA-binding protein IIF3," J. Biol. Chem., vol. 279, pp. 884-891 (2004).

Hagen et al., "Sp1-mediated transcriptional activation is repressed by Sp3," Embo. J., vol. 13, 3843-3851 (1994).

Hagen et al., "Cloning by recognition site screening of two novel GT box binding proteins: a family of Sp1 related genes," Nucleic Acids Res., vol. 20, pp. 5519-5525 (1992).

Henikoff & Henikoff, "Amino acid substitution matrices from protein blocks," Proc. Natl. Acad. Sci. USA, vol. 89, pp. 10915-10919 (1992). <saved to server>.

Hutvagner et al., "Sequence-specific inhibition of small RNA function," PLoS Biol., vol. 2, E98 (2004).

Ito et al., "Identity between TRAP and SMCC complexes indicates novel pathways for the function of nuclear receptors and diverse mammalian activators," Mol. Cell., vol. 3, pp. 361-370 (1999).

James et al., "Molecular remodeling of cardiac contractile function," Am. J. Physiol., vol. 273, H2105-H2118 (1997).

Karlin & Altschul, "Applications and statistics for multiple high-scoring segments in molecular sequences," Proc. Natl. Acad. Sci. USA, vol. 90, pp. 5873-5877 (1993).

Khvorova et al., "Functional siRNAs and miRNAs exhibit strand bias," Cell, vol. 115, pp. 209-216 (2003).

Kroll et al., "Transgenic *Xenopus* embryos from sperm nuclear transplantations reveal FGF signaling requirements during gastrulation," Development, vol. 122, pp. 3173-3183 (1996).

Lagos-Quintana et al., "Identification of tissue-specific microRNAs from mouse," Curr. Biol., vol. 12, No. 9, pp. 735-739 (Apr. 30, 2002).

Lagos-Quintana et al., "New microRNAs from mouse and human," RNA, vol. 9, No. 2, pp. 175-179 (Feb. 2003).

Lee et al., "An extensive class of small RNAs in *Caenorhabditis elegans*," Science, vol. 294, pp. 862-864 (2001).

Lee et al., "The nuclear RNase III Drosha initiates microRNA processing," Nature, vol. 425, pp. 415-419 (2003).

Liu et al., "A highly efficient recombineering-based method for generating conditional knockout mutations," Genome Res., vol. 13, pp. 476-484 (2003).

Lompre et al., "Expression of the cardiac ventricular alpha- and beta-myosin heavy chain genes is developmentally and hormonally regulated," J. Biol. Chem., vol. 259, pp. 6437-6446 (1984).

Lu et al., "Regulation of skeletal myogenesis by association of the MEF2 transcription factor with class II histone deacetylases," Mol. Cell, vol. 6, pp. 233-244 (2000).

Lund et al., "Nuclear export of microRNA precursors," Science, vol. 303, pp. 95-98 (2004).

Meister et al., "Sequence-specific inhibition of microRNA- and siRNA-induced RNA silencing," RNA, vol. 10, pp. 544-550 (2004).

Muncke et al., "Missense mutations and gene interruption in PROSIT240, a novel TRAP240-like gene, in patients with congenital heart defect (transposition of the great arteries)," Circulation, vol. 108, pp. 2843-2850 (2003).

Needleman & Wunsch, "A general method applicable to the search for similarities in the amino acid sequence of two proteins," J Mol Biol. 48:443-453(1970). <saved to server>.

Nicol et al., "Activated MEK5 induces serial assembly of sarcomeres and eccentric cardiac hypertrophy," Embo. J., vol. 20, pp. 2757-2767 (2001).

Notice of Intent to Grant corresponding to European Patent Application 06845222.6 dated Dec. 30, 2011.

Office Communication corresponding to Chinese Patent Application No. 200680052681.X dated Dec. 1, 2010. Translation.

Office Communication corresponding to Chinese Patent Application No. 200680052681.X dated Nov. 9, 2011. Translation.

Office Communication corresponding to Mexican Patent Application No. MX/a/2009/007860 dated Dec. 4, 2010. Translation.

Office Communication corresponding to New Zealand Patent Application No. 569738 dated Oct. 19, 2011.

Pearson & Lipman, "Improved tools for biological sequence comparison," Proc. Natl. Acad. Sci. USA, vol. 85, pp. 2444-2448 (1988). <saved to server>.

Pillai et al., "Tethering of human go proteins to mRNA mimics the miRNA-mediated repression of protein synthesis," RNA, vol. 10, 1518-1525 (2004).

Pinna et al., "Protein kinase CK2 ("casein kinase-2") and its implication in cell division and proliferation," Prog. Cell Cycle Res., vol. 3, pp. 77-97 (1997).

Rodriguez et al., "Identification of mammalian microRNA host genes and transcription units," Genome Res., vol. 14, pp. 1902-1910 (2004).

Sanbe et al., Reengineering inducible cardiac-specific transgenesis with an attenuated myosin heavy chain promoter. Circ. Res., vol. 92, pp. 609-616 (2003).

Santalucia et al., "Factors involved in GLUT-1 glucose transporter gene transcription in cardiac muscle," J. Biol. Chem., vol. 274, pp. 17626-17634 (1999).

Schonberger et al., "Mutation in the transcriptional coactivator EYA4 causes dilated cardiomyopathy and sensorineural hearing loss," Nat. Genet., vol. 37, pp. 418-422 (2005).

Schwarz et al., "Asymmetry in the assembly of the RNAi enzyme complex," Cell, vol, 115, pp. 199-208 (2003).

Sempere et al., "Expression profiling of mammalian microRNAs uncovers a subset of brain-expressed microRNAs with possible roles in murine and human neuronal differentiation," Genome Biol., vol. 5, R13 (2004).

Sokol et al., "Mesodermally expressed *Drosophila* microRNA-1 is regulated by Twist and is required in muscles during larval growth" Genes and Development, vol. 19, No. 19, pp. 2343-2354 (Oct. 1, 2005).

Subramaniam et al., "Tissue-specific regulation of the alpha-myosin heavy chain gene promoter in transgenic mice," J. Biol. Chem., vol. 266, pp. 24613-24620 (1991).

Subramaniam et al., "Transgenic analysis of the thyroid-responsive elements in the alpha-cardiac myosin heavy chain gene promoter," J. Biol. Chem., vol. 268, 4331-4336 (1993).

Supplementary European Search Report corresponding to European Patent Application No. 06 845 222.6 dated Sep. 17, 2010.

Tibanyenda et al., "The effect of single base-pair mismatches on the duplex stability of d(T-A-T-T-A-A-T-A-T-C-A-A-G-T-T-G). d(C-A-A-C-T-T-G-A-T-A-T-T-A-A-T-A)," Eur. J. Biochem., vol. 139, vol. 19-27 (1984). <saved to server>.

Treisman, J., "*Drosophila* homologues of the transcriptional coactivation complex subunits TRAP240 and TRAP230 are required for identical processes in eye-antennal disc development," Development, vol. 128, pp. 603-615 (2001).

Turner et al., "Improved Parameters for Prediction of RNA Structure," Cold Spring Harb. Symp. Quant. Biol., LII, pp. 123-133 (1987).

Wang et al., "Activation of cardiac gene expression by myocardin, a transcriptional cofactor for serum response factor," Cell, vol. 105, 851-862 (2001).

Wayne et al., "Mutations in the transcriptional activator EYA4 cause late-onset deafness at the DFNA10 locus," Hum. Mol. Genet., vol. 10, pp. 195-200 (2001).

Yan et al., "Highly Coordinated Gene Regulation in Mouse Skeletal Muscle Regeneration," J. Biol. Chem., vol. 278, Issue 10, pp. 8826-8836 (2003).

Yi et al., "Exportin-5 mediates the nuclear, export of pre-microRNAs and short hairpin RNAs," Genes Dev., vol. 17, pp. 3011-3016 (2003).

Yi et al., "Overexpression of exportin 5 enhances RNA interference mediated by short hairpin RNAs and microRNAs," RNA, vol. 11, pp. 220-226 (2005).

Blau et al., "Plasticity of the differentiated state," Science, vol. 230, pp. 758-766 (1985).

Bonini et al., "The eyes absent gene: genetic control of cell survival and differentiation in the developing *Drosophila* eye," Cell, vol. 72, pp. 379-395 (1993).

Ito et al., "Involvement of the TRAP220 component of the TRAP/SMCC coactivator complex in embryonic development and thyroid hormone action," Mol. Cell., vol. 5, pp. 683-693 (2000).

McKinsey et al., "Signal-dependent nuclear export of a histone deacetylase regulates muscle differentiation," Nature, vol. 408, pp. 106-111 (2000).

Office Communication corresponding to New Zealand Patent Application No. 569738 dated Apr. 13, 2010.

Extended Eurpean Search Report corresponding to European Patent Application No. 12166173.0-1212 dated Aug. 14, 2012.

Kim et al., "MicroRNA miR-206 promotes muscle differentiation," The Journal of Cell Biology, vol. 174, No. 5, pp. 677-687 (Aug. 21, 2006).

McCroskery et al., "Improved muscle healing through enhanced regeneration and reduced fibrosis in myostatin-null mice," Journal of Cell Science, vol. 118, pp. 3531-3541 (Jan. 1, 2005).

Notice of Acceptance corresponding to New Zealand Patent Application No. 569738 dated Feb. 12, 2012.

Office Communication corresponding to Australian Patent Application No. 2006326517 dated Jun. 26, 2012.

Office Communication corresponding to Japanese Patent Application No. 2008-545718 dated Aug. 16, 2012.

Office Communication corresponding to Mexican Patent Application No. MX/a/20110001494 dated Aug. 29, 2012.

Sweetman et al., "Specific requirements of MRFs for the expression of muscle specific microRNAs, miR-1, miR-206 and miR-133," Developmental Biology, vol. 321, No. 2, pp. 491-499 (Sep. 15, 2008).

Townley et al., "MicroRNAs 1, 133, and 206: Critical factors of skeletal and cardiac muscle development, function, and disease," International Journal of Biochemistry and Cell Biology, vol. 42, No. 8, pp. 1252-1255 (Aug. 1, 2010).

Zhao et al., "Regulation of MEF2 by Histone Deacetylase 4- and SIRT1 Deacetylase-Mediated Lysine Modifications," vol. 25, No. 19, pp. 8456-8464 (Oct. 2005).

Notice of Acceptance corresponding to Australian Patent Application No. 2006326517 dated Feb. 7, 2013.

Notice of Acceptance corresponding to New Zealand Patent Application No. 593688 dated Jan. 30, 2013.

Office Communication corresponding to Canadian Patent Application No. 2,634,046 dated Nov. 21, 2012.

\* cited by examiner

Figure 10G

Chromosome 2 miR-1/133 cluster enhancer sequences

```
   1 GAGCAAGTTT CACTAGGGCC ACACAGTATC ATTGAGCACT GAGCGTGGAA GGAGACAGAT
  61 GGGCCACGTT TCTCCTCCCT CTTTCTAGCC TTCCTTCTCC CTCCCTTTTC TTATACATTA
 121 TATCCTGGCG GCAGTTTTCC CTCCCTCCAC TCCTCCCAGT TCCTTCCCCA CTTCCATTCT
 181 CCCCCAGATC CATTCCTCTT ATGCCCCCCC CCCCCAAGAG CAGGCTTTCC ATGAATACCC
 241 ACCAAACATG GCATAACAAG TTACAATAAG ATCAGGAACA AACCCTCATA TCAAGGCTGG
 301 ATGAGGCAAC CCAACAGGAG GAAAAGGGCC CCAAGAGCAG GCAAAAAACT CCCACTGTTG
 361 TGTCTTCTGC TAGAACACAA AGCTACACAA CTATAATGTA TATGCAGAGG ACCCAGCTCA
 421 GTCTCATCAG GGTCCGTGTT TGTTGCTACA GTTTCTGTGA ACCTCTGTGG GCTCTGCTTA
 481 GTTGGTTCTG TGGGTTGTGT TCTTGTGGCA TCCTCAACTC CTCTGGCTCC TACAATCTTT
 541 CCTCCCATCT TCTTTGGAGT TCCCCTGGCC ATGCCTGATG TTTGGTTGGC TTGGCTGTGT
 601 GGGCCTCTGC ATTTATTTCC GTCAGTTGCT GGAAAGCATC CCTCTGTTGA CAGTTGGTCC
 661 ATGCACTGAT CTATGAGGAT AGCAGAGTAT CACTAGGAAT TACTTTATTG TCTTTTTTGC
 721 CAGTCGTTTT TGGTTCTCTC CCGAGTCTCT GGGCTGTCCA GTCTCTGGTT CCTGGCCTTC
 781 CAGACACTGT CAGTTGTGGG TTCCCTTTTG TGGTGTTGGC CTCAACTTGG CCAGTCATTG
 841 GTTGGCCATT CCCACAAGTT CTACACCACC ATTACCCTAG CATGTCTCGC AGGCAGGACA
 901 GATTGTACGC GGAAGGATTT ATGGCTGGGT TATGTCTCAG TCCCAGGGCT GGAAGCCTTG
 961 CCTGGTTAAA GAAGACAGCT AGTTCTGACT CAGTATTCCC TGTTACTAGC AGAATTCACT
1021 AGGATTACCC TCACCCTCAG GGCATTTCCA CAGCACTAGG GTTCTGCATT GCCTCTCCAA
1081 TACCCCCTCC AATTCCAGTC GCCTTTCCCA GAACTCTCCT CCCCCAGCCT GATCCCTATT
1141 GTTCCCACCC CCATCCACCC CCAGTCCACC TACAAAGCTC TTTCCCCTTC CCAAGAAGAT
1201 CCATGAGTTT CTCTGTGTCT GTGGATTGGA GTATGATCTG TGGATTTAGC AGCTAATGTT
1261 CACTTACCAG TGAGTACACA CCGTTTGTCT TTTGGGTCTG GGTTACCTCA CTCAGGGTGG
1321 ATTTTGGATT TTTTTTTTTG AGTGCTATCC ATTTGTCTGC AAATGTCATG ATGTCATTTT
1381 TTTTAACAGC TGAGGAATTC TCTCAGAACC ACATTTTCTT TATCCATTAT TCAGATTGTT
              MEF2 site
1441 CCCAGTTTCT GGCTATTATA AGGCTGCTAT GAACATGGTT GAACAAGTGT CCTTGTGGTA
              tcggTAcA ca
              (MEF mutation)
1501 GGATGTGGCA TCCTTTGGGT ATATGCCTAG GAGTGGTATC GATGGGTCTC GAGGTAGATC
1561 AATTCCCGAT TTTCTGAGAA ACTGCCATAT CTGTTTCCAA AGTGGCTGTG TAAGTTTGCG
1621 CTCCCACCAG CAACGGAGGA GTGTTCTCCT TACTCCTCCC ACATTATCAA CAGTGTGAGC
1681 TGTCACTTGT GTTTTGATC TTAGCCTTTC TGACAGGTGT AAGATGGAAT CTCAAAGTAG
1741 CTTTGATTTG CATTTCCCTG CTGGCTAAGG ATGTTGAACA TTTCTTTAAG TGTTTCTCAG
1801 CCATTTGAGA TTTATCCATT GAGAATTCTG TTTAGATCTG AACTCCACCT TCTAATTGGA
1861 TTATTTGGTT TTTAAAATAT CCACTTTCTC GAGTTCTTAA TGGGTTCTGG ATATTAGCCC
1921 TCTGTCAAAT GTGGAGTTGG TGAAGATCTT TTCCCATTCG GTAGGTTTTG TCCTATTGAC
                                                      CArG Box
1981 AGTGTCCTTT GCTTCACAGA AGCTTTTCAG TTTCATGAGG TCCCATTTAT TGATTGTTGA
                                                       atcTTggT ct
                                                      (CArG Box mutation)
2041 TCTTAGTGCC TGTGCTATTG ATGTCTATTC AGGAAGTTGT CTCCTGTGCC AATGCGTTCA
2101 AGGCTATTTC CCACTTTCTC TTCTATTAGG TTCAGTGTAT CTCATTTTAT GTTGAGGTCT
2161 TTGATCCACT TAGAGTTGAG TTTTGTGCAG AGTGATAGAT ATGGATCTAT TTGCATTCTT
2221 CTACATGCAG ATATCCAGTA AGACCAGCAT CATTTATTGC GGATGCTTTT TAAATTTTTT
2281 CGCTTGTGTA TTTCTGGCTT CTTTATAAAA ATCAGGTGTT CACTGATTTC ATTGATCAGC
2341 CAATGCTTTT CTGCCGATAC CATGTGGTTT TATTGCTATA GCTCTGAGGT ACAGCTTGAG
2401 TCAGGGATGT GATGCCCCTG GACGTCCTTT TATTGTACAG GAGTATCCTA GGTTTAGCTA
2461 TCCTAGGTTT TTTGGTTTTC CACATGGAGT TAAGTATTGT CCTTTCAAGG TCTATAGAGA
2521 ATTGCATTGG GATTTTGGTG GAGATTGTAT TGCATTTGTA GATTTGGTAG GGTGGCCATT
2581 TTTACTATGG TAATCCTACC
```

Figure 12 miR-26 (SEQ ID NO:6)
    mmu-miR-26a MIMAT0000533
    UUCAAGUAAUCCAGGAUAGGC (SEQ ID NO:12)

mmu-miR-26b MIMAT0000534
    UUCAAGUAAUUCAGGAUAGGUU (SEQ ID NO:13)

miR-29 (SEQ ID NO:7)
    mmu-miR-29a MIMAT0000535
    UAGCACCAUCUGAAAUCGGUU (SEQ ID NO:14)

mmu-miR-29b MIMAT0000127
    UAGCACCAUUUGAAAUCAGUGUU (SEQ ID NO:15)

mmu-miR-29c MIMAT0000536
    UAGCACCAUUUGAAAUCGGU (SEQ ID NO:16)

miR-30 (SEQ ID NO:8)
    mmu-miR-30a-3p MIMAT0000129
    CUUUCAGUCGGAUGUUUGCAGC (SEQ ID NO:17)

mmu-miR-30b MIMAT0000130
    UGUAAACAUCCUACACUCAGCU (SEQ ID NO:18)

mmu-miR-30c MIMAT0000514
    UGUAAACAUCCUACACUCUCAGC (SEQ ID NO:19)

mmu-miR-30d MIMAT0000515
    UGUAAACAUCCCCGACUGGAAG (SEQ ID NO:20)

mmu-miR-30e* MIMAT0000249
    CUUUCAGUCGGAUGUUUACAG (SEQ ID NO:21)

miR-128 (SEQ ID NO:9)
    mmu-miR-128a MIMAT0000140
    UCACAGUGAACCGGUCUCUUUU (SEQ ID NO:22)

mmu-miR-128b MIMAT0000675
    UCACAGUGAACCGGUCUCUUUC (SEQ ID NO:23)

Figure 21 miR-1 is progressively expressed during skeletal muscle satellite cell differentiation miR-1/206 inhibits Pax7 but not Pax3 expression MiR-1/206 inhibits BDNF but not GDNF expression miR-1/206 enhances satellite cell differentiation B  miR-1/206 enhances satellite cell differentiation Overexpression of miR-1/206 enhances satellite cell differentiation kinetics

MICRORNAS THAT REGULATE MUSCLE CELL PROLIFERATION AND DIFFERENTIATION

CROSS REFERENCE TO RELATED APPLICATIONS

The presently disclosed subject matter claims the benefit of U.S. Provisional Patent Application Ser. No. 60/749,544, filed Dec. 12, 2005; the disclosure of which is incorporated herein by reference in its entirety.

GRANT STATEMENT

This work was supported by grant R01-HL075251 from the National Institutes of Health. Thus, the U.S. government has certain rights in the presently disclosed subject matter.

TECHNICAL FIELD

The presently disclosed subject matter relates, in general, to methods and compositions for modulating gene expression in a myocyte. More particularly, the presently disclosed subject matter relates to methods of using microRNAs (miRNAs) to modulate the expression level of a gene in a myocyte, and to compositions comprising miRNAs.

BACKGROUND

Understanding the molecular mechanisms that regulate cellular proliferation and differentiation is a central theme of developmental biology. MicroRNAs (miRNAs) are a recently discovered class of ~22-nucleotide regulatory RNAs that post-transcriptionally regulate gene expression[1,2]. Increasing evidence has pointed to the potential role of miRNAs in a variety of biological processes[3-8].

However, there remains a long-felt and continuing need in the art for characterization of the role or roles of miRNAs in biological processes. The presently disclosed subject matter addresses this and other needs in the art.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In one embodiment of the presently disclosed subject matter, a method for treating a muscle injury in a subject is provided. In some embodiments, the method comprises administering to a muscle injury site in a subject an effective amount of a miRNA or a vector encoding the miRNA or an inhibitor of miRNA, wherein the miRNA is targeted to a gene in a myocyte at the muscle injury site. In some embodiments, the inhibitor of miRNA is capable of hybridizing to a target miRNA and in some embodiments, the target miRNA is selected from the group consisting of miR-1, miR-133, miR-206, miR-208, miR-22, miR-26, miR-29, miR-30, miR-128, miR-143, and miR-145. In some particular embodiments, an miRNA-133 and an inhibitor of miRNA-1 are administered in combination to the muscle injury site at a first time point and an miRNA-1 and an inhibitor of miRNA-133 are administered in combination to the muscle injury site at a second time point to thereby treat the muscle injury. In some embodiments, the muscle injury results from a mechanical muscle trauma, a muscular degenerative disorder, a cardiac insult, or a combination thereof. In some embodiments, the subject is a mammal.

In another embodiment of the presently disclosed subject matter, a method for modulating myocyte differentiation, proliferation, or both is provided. In some embodiments, the method comprises contacting a myocyte with a miRNA or a vector encoding the miRNA targeted to a gene in the myocyte which can modulate myocyte differentiation, proliferation, or both. In some embodiments, the modulating is inhibiting and in some embodiments, the miRNA inhibits translation of the gene.

In still another embodiment of the presently disclosed subject matter, a method for modulating expression of a gene in a myocyte is provided. In some embodiments, the method comprises contacting a myocyte with a miRNA or a vector encoding the miRNA targeted to a gene in the myocyte. In some embodiments, the modulating is inhibiting and in some embodiments, the miRNA inhibits translation of the gene.

In a further embodiment of the presently disclosed subject matter, a method for inhibiting the expression of a gene in a myocyte is provided. In some embodiments, the method comprises transforming the myocyte with a vector encoding a miRNA molecule, wherein the miRNA molecule comprises a nucleotide sequence at least 70% identical to a contiguous 17-24 nucleotide subsequence of the gene, except that the miRNA will comprise a uracil in place of any thymidines that would be found in the gene. In some embodiments, the miRNA inhibits translation of the gene.

In some embodiments of the methods disclosed herein, the miRNA employed comprises a nucleotide sequence selected from the group consisting of any of SEQ ID NOs: 1-11 and sequences at least 70% identical to any of SEQ ID NOs: 1-11. In some embodiments, the miRNA is selected from the group consisting of miR-1, miR-133, miR-206, miR-208, miR-22, miR-26, miR-29, miR-30, miR-128, miR-143, and miR-145. Further, in some embodiments, the miRNA is targeted to a 3' untranslated region of the gene.

Further, in some embodiments of the methods, the gene targeted by the miRNA is selected from the group consisting of a myocyte differentiation gene (e.g., a gene encoding a histone deacetylase 4 (HDAC4) polypeptide or a thyroid hormone receptor protein 240 (TRAP240)), a myocyte proliferation gene (e.g., a gene encoding a serum response factor (SRF) polypeptide) and a hormone related protein (e.g. a gene encoding thyroid hormone associated protein 1 (Thrap1).

In another embodiment of the presently disclosed subject matter, a vector encoding an miRNA is provided. In some embodiments, the vector comprises a promoter operatively linked to a nucleic acid molecule encoding the miRNA molecule; and a transcription termination sequence. Further, in some embodiments, the vector is incorporated in a kit further comprising at least one reagent for introducing the vector into a myocyte. The kit, in some embodiments, further comprises instructions for introducing the vector into a myocyte.

Accordingly, it is an object of the presently disclosed subject matter to provide a method for manipulating gene expression in a myocyte using an miRNA-mediated approach. This object is achieved in whole or in part by the presently disclosed subject matter.

An object of the presently disclosed subject matter having been stated above, other objects and advantages will become apparent to those of ordinary skill in the art after a study of the following description of the presently disclosed subject matter and non-limiting examples.

BRIEF DESCRIPTION OF THE DRAWINGS

FIG. 1a shows miRNA array expression data from C2C12 myoblasts cultured in growth medium (GM) or in differentiation medium (DM) for 0, 1, 3 and 5 days, respectively. Normalized log (base 2) data was hierarchically clustered by gene and is plotted as a heat map. The range of signal was from −4 fold to +4 fold. Yellow denotes high expression and blue denotes low expression, relative to the median and only the miRNA nodes that are up-regulated in differentiation medium are shown.

FIG. 1b depicts a Northern blot analysis of the expression of miR-1 and miR-133 using total RNA isolated from C2C12 myoblasts cultured in GM or in DM for 0, 1, 3 and 5 days, respectively. tRNAs were used as a loading control.

FIG. 1c depicts a Northern blot analysis of the expression of miR-1 and miR-133 in adult mouse tissues.

FIG. 1d depicts a Northern blot analysis of the expression of miR-1 and miR-133 in embryonic day 13.5 (E13.5) and 16.5 (E16.5) mouse tissues.

FIG. 1e depicts a Northern blot analysis of the expression of miR-1 and miR-133 in neonatal mouse tissues. Same amount of total RNAs from adult heart and skeletal muscle were loaded into blots to serve as a comparison to embryonic and neonate RNA (FIGS. 1d and 1e).

FIGS. 2a-2e show results of experiments wherein cells were continuously cultured in GM for 24 hr after transfection, then transferred to differentiation medium (DM) for 12 hr before immunostaining for myogenin (FIG. 2a) or 36 hr before immunostaining for MHC (FIG. 2b). C2C12 myoblasts cultured in GM were electroporated with double-stranded miRNA duplexes for miR-1, miR-133 (or their mutants as indicated), or miR-208 and GFP as controls and cultured for 24 hr before: Western blotting using indicated antibodies (FIG. 2c); cells were transferred to DM for 24 hr and RT-PCR for the indicated genes were performed (FIG. 2d); or cells were transferred to DM for 24 hr and Western blotting using the indicated antibodies (FIG. 2e).

FIGS. 2f-2h show results of experiments wherein C2C12 myoblasts cultured in GM were electroporated with 2'-O-methyl antisense oligonucleotide inhibitors for miR-1, miR-133 or miR-208 and GFP as controls. Cells were cultured in GM for 24 hr after transfection then transferred into DM for: 12 hr before immunostaining for phospho-histone H3 (FIG. 2f); 24 hr before performing RT-PCR for the indicated genes (FIG. 2g); or 24 hr before Western blotting using indicated antibodies (FIG. 2h).

FIGS. 2i and 2j show results of experiments wherein C2C12 myoblasts cultured in GM were electroporated with either the miRNA duplexes or 2'-O-methyl antisense oligonucleotide inhibitors as indicated. Cells were cultured in GM for 24 hr after transfection, then transferred into DM for 12 hr before immunostaining for myogenin (FIG. 2i) or phospho-histone H3 (FIG. 2j). Positive stained cells were counted and data are presented as the expression level relative to a GFP control (100%).

FIGS. 3a-3h show data from Xenopus embryo experiments. Xenopus embryos derived from uninjected (FIGS. 3a and 3b), GFP RNA control-injected (FIGS. 3c and 3d), miR-1-injected (FIGS. 3e and 3f), or miR-133-injected (FIGS. 3g and 3h) embryos stained with anti-tropomyosin and shown at stage 32 under brightfield (FIGS. 3a, 3c, 3e, and 3g) or fluorescence (FIGS. 3b, 3d, 3f, and 3h). Note the lack of staining for heart tissue (FIGS. 3b and 3d, H arrows) and disruption of segmented somites (FIGS. 3f and 3h, S arrows).

FIGS. 3i-3k show data from transverse sections of the Xenopus embryos. Transverse sections of Xenopus embryos corresponding to the position of the heart at stage 32 from uninjected (FIG. 3i), miR-1 injected (FIG. 3j), or miR-133 injected (FIG. 3k) embryos stained with anti-tropomyosin to visualize somites (S arrows) and cardiac tissue (H arrows), and anti-phospho-histone H3 (red) to visualize cells in S phase. Each set of injections was conducted at least twice independently, and the phenotype was observed in at least 90% of a minimum of 50 embryos scored by whole mount immunostaining.

FIG. 4a depicts data showing repression of SRF and HDAC4 3' UTRs by miR-133 and miR-1. Luciferase reporters containing either miR-133 complementary sites from mouse SRF 3' UTR (SRF-3'-UTR), miR-1 complementary sites from mouse HDAC4 3' UTR (HDAC4-3'-UTR) or the perfect antisense sequences of miR-133 (miR-133-luc) or miR-1 (miR-1-luc) were co-transfected with the indicated miRNA expression vectors or their mutants. Luciferase activity was determined 48 hr after transfection. Data represent the mean±s.d. from at least three independent experiments in duplicate (* P<0.05).

FIG. 4b depicts data showing results of SRF-3'-UTR, HDAC4-3'-UTR, and MCK-luc luciferase reporters transfected into C2C12 myoblasts. Cells were maintained in GM for 24 hr (GM) or transferred into DM for 1 day (DM1) or 3 days (DM3) before luciferase activity was determined.

FIGS. 4c-4e depict data showing results of C2C12 myoblasts cultured in GM and electroporated with indicated double-stranded miRNA duplexes (or their mutants), or miR-208 and GFP as controls. Cells were cultured in GM for 24 hr after transfection before: Western blotting using anti-SRF and anti-HDAC4 antibodies (FIG. 4c); cells were transferred into DM for 24 hr and RT-PCR for the indicated genes performed (FIG. 4d); cells were transferred into DM for 24 hr and Western blotting using indicated antibodies. C2C12 myoblasts cultured in GM were electroporated with indicated 2'-O-methyl antisense oligonucleotide inhibitors (FIG. 4e).

FIGS. 4f and 4g depict data showing results of cells cultured in GM for 24 hr after transfection, then transferred into DM for 24 hr before: RT-PCR for the indicated genes performed (FIG. 4f); and Western blotting using indicated antibodies (FIG. 4g).

FIG. 4h depicts data showing results of C2C12 myoblasts cultured in GM and electroporated with indicated double-stranded miRNA duplexes or/and expression plasmids for SRF or HDAC4, as indicated. Cells were cultured in GM for 24 hr after transfection. Western blotting performed 24 hr after transfer into DM using indicated antibodies.

FIG. 4*i* depicts data showing results of C2C12 myoblasts cultured in GM or DM for 0, 1, 3 or 5 days. Western blotting was performed using indicated antibodies.

FIGS. 7*a* and 7*b* show Northern blot analysis of the expression of miR-1 (FIG. 7*a*) and miR-133 (FIG. 7*b*) using total RNA isolated from C2C12 myoblasts cultured in GM or in differentiation medium (DM) for 0, 1, 3 and 5 days, respectively. Both mature miRNAs and their precursors (Pre) are indicated. tRNAs were used as a loading control.

FIG. 7*c* shows semi-quantitative RT-PCR analysis of skeletal muscle differentiation marker genes. GAPDH was used as a control for equal loading.

FIG. 7*d* shows expression of skeletal muscle differentiation markers. C2C12 myoblasts were cultured in growth medium (GM) or in differentiation medium (DM) for 0, 1, 3 and 5 days, and Western blots performed with cell extracts using the indicated antibodies. β-tubulin serves as a loading control.

FIG. 9*a* is a diagram showing miR-1 and miR-133 genes clustered on mouse chromosomes 2 and 18. Probes used for Northern blots in FIGS. 9*b*-9*e* are denoted.

FIGS. 9*b*-9*e* show data of Northern blot analysis of the expression of primary transcripts for miR-1 (FIGS. 9*c* and 9*e*) and miR-133 (FIGS. 9*b* and 9*d*) from chromosome 2 (FIGS. 9*d* and 9*e*) and chromosome 18 (FIGS. 9*b* and 9*c*). 20 μg of total RNA from the indicated adult mouse tissues was used.

FIG. 10*a* shows data of *Xenopus laevis* transgenic for mouse miR-1 and miR-133 genomic sequence linked to dsRed illustrating somite (S, arrows) expression at stage 28.

FIG. 10*b* shows transgenic (Tg) *Xenopus laevis* carrying a miR-1 and miR-133-containing transgene at stage 46 (lower embryo) and negative control (non-transgenic, Ct, upper embryo) under bright field.

FIG. 10*c* is a photograph of the same embryos as shown in FIG. 10*b* under fluorescence.

FIG. 10*d* is a high power magnification photomicrograph of the transgenic embryo in FIG. 10*b* under bright field showing expression of the transgene in the heart (H, arrows) and branchial arches (BA, arrows).

FIG. 10*e* is a high power magnification photomicrograph of the transgenic embryo in FIG. 10*b* under fluorescence showing expression of the transgene in the heart (H, arrows) and branchial arches (BA, arrows).

FIG. 10*f* is a high power magnification photomicrograph of a stage 46 transgenic embryo showing expression of the transgene in the somites (S, arrows).

FIG. 10*g* shows genomic DNA sequences (SEQ ID No:82) of miR-1/133 enhancer from mouse chromosome 2. A putative MEF2 site and CArG box are marked out, and mutations introduced into these sites are indicated.

FIG. 12 shows sequences of the miR-1 and miR-133 target sites in the 3' UTR of HDAC4 and SRF genes. Upper panel: HDAC4 3' UTR sequences from conserved vertebrate species human (SEQ ID NO:24), chimp (SEQ ID NO:25), mouse (SEQ ID NO:26), rat (SEQ ID NO:27), dog (SEQ ID NO:28), and chicken (SEQ ID NO:29), and their alignment with miR-1 (SEQ ID NO:1) and miR-206 (SEQ ID NO:3). Lower panel: SRF 3' UTR sequences from human (SEQ ID NOs:30 and 31) and rat (SEQ ID NOs:32 and 33) and their alignment with miR-133. Conserved nucleotide sequences are listed in upper case.

FIG. 14*a* shows that a mouse precursor miR-208 sequence (SEQ ID NO:34) is folded using mFold and with mature miR-208 (SEQ ID NO:4) sequence to the right. FIG. 14*b* shows a sequence alignment of mouse (SEQ ID NO:35), rat (SEQ ID NO:36), and human (SEQ ID NO:37) precursor miR-208 sequences. Mature miR-208 sequence is shown in the upper right side of FIG. 14A. Asterisks denote perfect sequence conservation. FIG. 14*c* shows miR-208 originates from a alpha-MHC intron. Mouse miR-208 is located within intron 29 of α-MHC. Similarly, human miR-208 lies within intron 28 of α-MHC.

FIG. 15a shows data demonstrating miR-208 is cardiac-specific. The upper signal is pre-miR-208 transcript, while the lower signal is the mature 22 nt form.

FIG. 15b shows data of miR-208 expression in tissues from neonatal mouse relative to adult heart and skeletal muscle.

FIG. 15c shows data of miR-208 expression in various tissues from E13.5 and E16.5 mice relative to adult heart and skeletal muscle.

FIG. 16a shows a Northern blot prepared from cardiomyocytes infected with Ad-GFP or Ad-208 probed using radiolabeled miR-208 antisense oligonucleotide. FIG. 16b shows epifluorescent micrographs of infected cardiomyocytes at MOIs 1 and 10.

FIG. 18C shows the mature miR-208 sequence (SEQ ID NO:4) bound to predicted miR-208 target site within the 3' UTR of human (SEQ ID NO:38) and mouse (SEQ ID NO:39) Thrap1 gene. Note the perfectly conserved target seed region within both predicted targets (the $2^{nd}$ to $8^{th}$ nucleotides at the 5' end of miR-208).

FIG. 20A shows data from miRNAs that are down-regulated in injured muscle. FIG. 20B shows data from miRNAs that are up-regulated in injured muscle.

FIG. 21 lists exemplary sequences for SEQ ID NOs: 6-9.

FIG. 23A shows a diagram of the expression construct for the expression of miR-1/206 and a GFP protein (FIG. 23A, left panel). Northern blot analysis shows the expression of miR-1 (FIG. 23a, right panel). FIG. 23B demonstrates the repression of a miR-1/206 sensor by miR-1 in 293 cells. 293 cells stably expressing the miR-1/206 sensor were transfected with expression vector for miR-1/206 (SDSA::miR-1), and images were obtained using phasecontrast (293 cell) or fluorescence to show expression of the dsRed reporter gene (dsRed::miR-1) or miRNA::GFP (SDSA::miR-1) or overlay of both (Overlay). Note that the expression of dsRed sensor and miR-1 is exclusive, indicating that miR-1 specifically represses the expression of the sensor reporter.

FIG. 24A is a sequence alignment of mouse Pax7 UTR (SEQ ID NO:40-41) with MiR-1 (SEQ ID NO:1) and miR-206 (SEQ ID NO:3). FIG. 24B discloses graphs showing luciferase reporters containing either mouse Pax7 3' UTR (Luc-Pax7::UTR), or its mutant (Luc-Pax7::UTR-M) or BDNF 3' UTR (Luc-BDNF:: UTR) or its mutant (Luc-BDNF::UTR-M) were co-transfected with the indicated miRNA expression vectors. Luciferase activity was determined 48 hr after transfection. Data represent the mean±s.d. from at least three independent experiments in duplicate. Note that miR-1/206 strongly represses the expression of Pax7 and BDNF 3' UTR reporters.

FIG. 25A is a Northern blot analysis of Pax7 expression, demonstrating that the transcripts levels of Pax7 mRNAs are not inhibited by 3' UTRs. FIG. 25B is a Western blot analysis demonstrating that Pax7, but not Pax3, protein level is lower in miR-1/206 overexpressed satellite cells. FIG. 25C shows images obtained using phase contrast (Phase/Contrast panels) or fluorescence to show expression of the Pax7 or Pax3 proteins (Pax7 and Pax3 panels) or miRNA::GFP (SDSA::miR-1/206 panels) or overlay (Overlay panels) in skeletal muscle satellite cells. Note the expression of Pax7, but not that of Pax3, is inhibited by miR-1/206.

FIG. 27A shows satellite cell images obtained using phase contrast or fluorescence to show cell proliferation index as marked by BrdU (BrdU panels) or miRNA::GFP (SDSA::miR-1+206 panel). Fewer BrdU positive cells were observed in miR-1/206 overexpressed satellite cells. FIG. 27B is a graph showing results of experiments wherein BrdU positive stained cells were counted in control and miR-1/206 overexpressed cells and data are presented as the ratio of BrdU positive cells versus total cells.

FIGS. 28A and 28B show results of experiments wherein satellite cells stably overexpress either miR-1/206 (SDSA-miR-1+206) or GFP (Control), then transferred to differentiation medium, where bFGF was removed, for 24 hr (FIG. 28A) or 48 hr (FIG. 28B) before immunostaining for myosin heavy chain (MyHC). Note enhanced MyHC staining in miR-1/206 overexpressed cells. DAPI labels cell nuclei.

BRIEF DESCRIPTION OF THE TABLES

Figure 1:
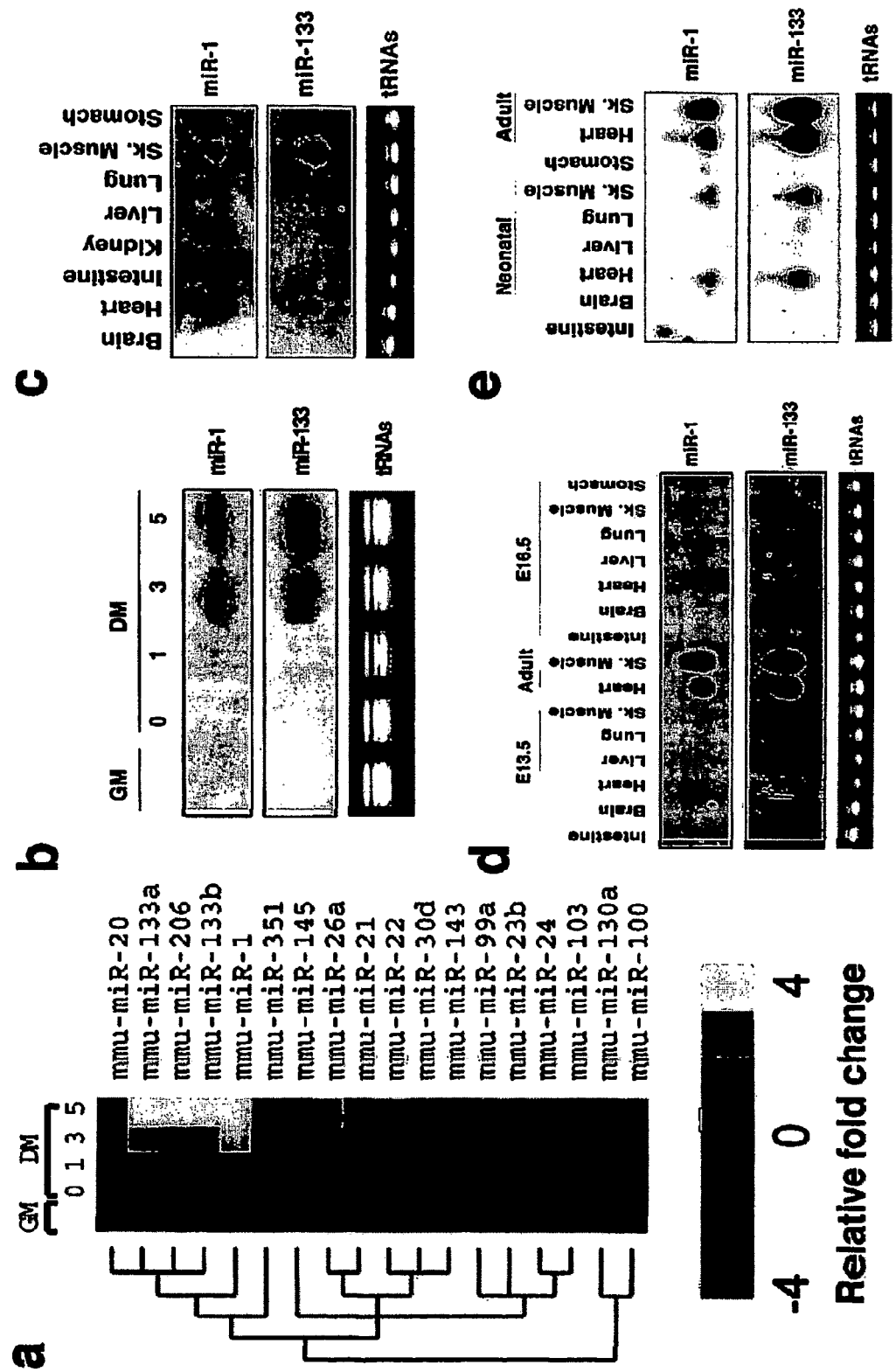
FIGS. 1a-1e depict data for expression of miR-1 and miR-133 in cardiac and skeletal muscle during development.

Table 1 is a list of one-letter nucleotide abbreviations used herein.

Table 2 shows the effect on myogenic proliferation and differentiation by miR-1 and miR-133. C2C12 myoblasts cultured in growth medium (GM) were electroporated with double-stranded miRNA duplex or 2'-O-methyl antisense oligos for miR-1, miR-133 or GFP as a negative control. 36 hr later, GM was replaced with differentiation medium (DM) for 8, 12 and 24 hr and cells were fixed for immunohistochemistry analysis using antibodies against myogenin, phospho-histone H3 and Myosin heavy chain (MHC). Positive cells were counted out of 5000 DAPI staining cell from randomly chosen field. Assays were performed three times independently with comparable results.

Table 3 lists the names and sequences of oligonucleotides disclosed herein.

BRIEF DESCRIPTION OF THE SEQUENCE LISTING

The Sequence Listing discloses, inter alia, the sequences of various miRNAs, specifically miR-1, miR-133, miR-206, miR-208, miR-22, miR-26, miR-29, miR-30, miR-128, miR-143, and miR-145 (SEQ ID NOs: 1-11, respectively) as well as additional polynucleotide sequences disclosed herein. In some cases RNA sequences are presented in the form of DNA (i.e. with thymidine present instead of uracil), it is understood that these sequences are also intended to correspond to the RNA transcripts of these DNA sequences (i.e. with each T replaced by a U).

DETAILED DESCRIPTION

Disclosed herein is the determination that particular miRNAs can modulate expression of specific genes in myocytes that affect differentiation and/or proliferation of the myocytes. This discovery has therapeutic applications, as disclosed herein, including treating muscle injuries having a wide variety of causes, such as for example mechanical muscle trauma, muscular degenerative disorders, and cardiac insult. Application of the discoveries disclosed herein further include modulating expression of one or more specific genes in myocytes utilizing miRNAs having specificity for the genes, and in turn, modulating functionality of the myocytes, such as for example differentiation and/or proliferation of the myocytes. Exemplary non-limiting miRNAs useful with the presently disclosed subject matter include miRNA-1, miRNA-133, miRNA-206, and miRNA-208.

For example, miRNA-1 (miR-1) and miRNA-133 (miR-133), which are clustered on the same chromosomal loci, are transcribed together in a tissue-specific manner during development. miR-1 and miR-133 each play distinct roles in modulating skeletal muscle proliferation and differentiation in cultured myoblasts in vitro and in *Xenopus* embryos in vivo. miR-1 promotes myogenesis by targeting histone deacetylase 4 (HDAC4), a transcriptional repressor of muscle gene expression. In contrast, miR-133 enhances myoblast proliferation by repressing serum response factor (SRF). The results reveal, for the first time, that two mature miRNAs, derived from the same miRNA polycistron and transcribed together, can perform distinct biological functions. The present disclosure thus provides molecular mechanisms in which miRNAs participate in transcriptional circuits that control muscle gene expression and embryonic development.

Figure 18:
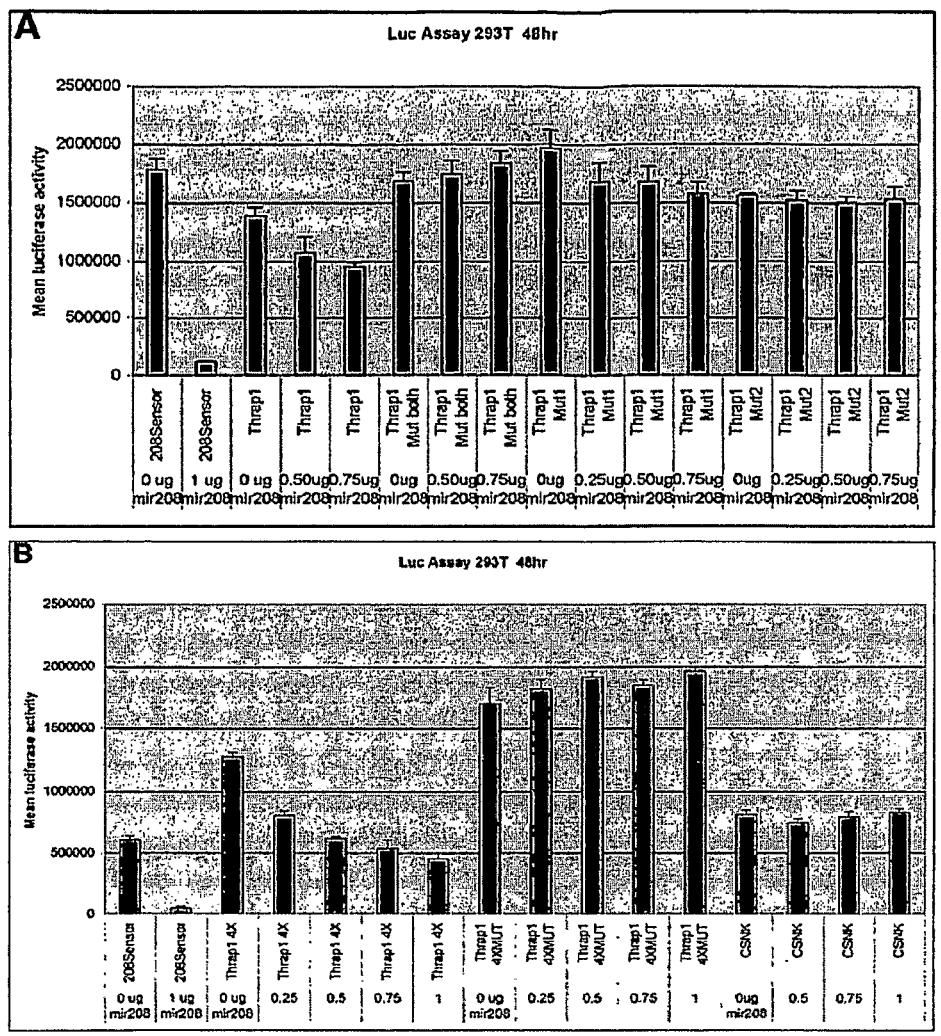
FIGS. 18A-18C are graphs and a sequence alignment showing data demonstrating miR-208 targets Thrap1. Luciferase reporters with an antisense miR-208 sequence (mir-208 sensor), or 3' UTRs of Hemoglobin-β (Hbb) and Thyroid hormone associated protein 1 (Thrap1) (FIG. 18A) or four copies of putative miR-208 binding sites from Thrap 1 3' UTR (FIG. 18B) were attached directly downstream of the luciferase gene and were co-transfected with increasing amounts of pCDNA3.1 miR-208 in 293T cells. miR-208 Sensor, Thrap1 and 4× Thrap1 reporters were both repressed in a dosage-dependent manner, while the negative control CSNK was not changed significantly.

As another non-limiting example, Thrap1 expression is likely regulated by miR-208. The 3' UTR of Thrap1 contains two predicted miR-208 binding sites (FIG. 18). The two targets are located ~80 by downstream of the Thrap1 stop codon and are separated from one another by only ~50 bp. Both targets are perfectly complementary with the seed region of miR-208. The Thrap1 gene encodes TRAP240, a 240 kd subunit of the TRAP (thyroid hormone receptor protein) complex that is ubiquitously expressed. TRAP is a multisubunit protein complex that is a coactivator for nuclear receptors and TRAP family members are important for proper development. Thus, miR-208 can regulate production of TRAP240 and promote hormone-dependent cardiomyocyte differentiation.

I. General Considerations

The first miRNA described, the lin-4 gene, which controls the timing of *C. elegans* larval development, was discovered to unexpectedly produce a 21-nucleotide long noncoding RNA that suppressed lin-14 protein expression without noticeably affecting lin-14 mRNA levels. This small RNA was found to target complementary sites in the 3' untranslated region (UTR) of lin-14[49,50]. Although this phenomenon was initially treated as a genetic oddity and virtually ignored, it is now appreciated that hundreds of small RNAs, now called miRNAs, similar to lin-4 exist in the genomes of divergent species and regulate translation of complementary mRNAs. While recent reports suggest roles for a few miRNAs in remarkably diverse biological processes, the majority remains largely uncharacterized.

I.A. miRNA Biogenesis & Mechanism

Figure 13:
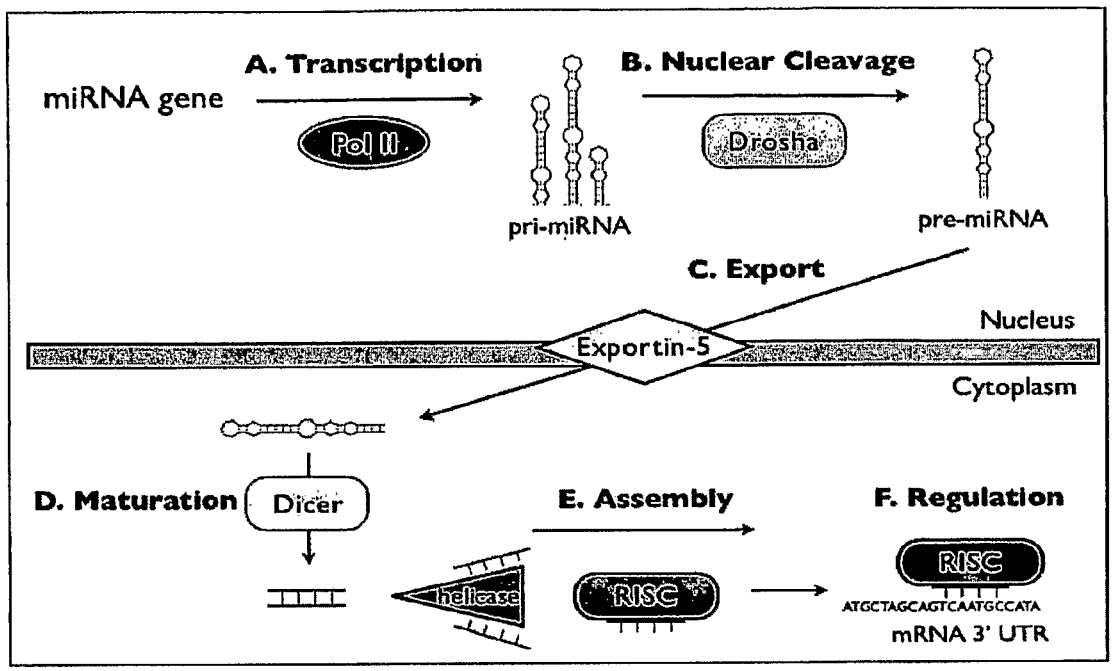
FIG. 13 depicts a model of miRNA biogenesis. (A) pri-miRNAs are transcribed in the nucleus by RNA polymerase II and (B) are processed by Drosha to pre-miRNAs containing a stem-loop. (C) Exportin-5 recognizes the 3' overhang left by Drosha and exports pre-miRNAs into the cytoplasm, where (D) Dicer cleaves pre-miRNAs below the stem-loop to produce a ~22 nucleotide duplex. (E) A single strand is incorporated in the RISC, which (F) recognizes complementary sequences within 3' untranslated regions of mRNAs and regulates gene expression by translational suppression or mRNA cleavage.

A general model for miRNA biogenesis is depicted in FIG. 13. Mature miRNAs are ~22 nucleotides (nt) in length that were processed from longer transcripts[51,52]. Primary-miRNAs (pri-miRNAs) can be transcribed by RNA Pol II as independent transcriptional units or can originate from spliced-out introns of host genes[53]. The miRNA processing pathway can begin with pri-miRNA nuclear cleavage by RNAse III endonuclease Drosha, which produces a ~70-nt long intermediate precursor-miRNA (pre-miRNA) that has a stem-loop structure[54]. Exportin-5 recognizes the staggered cut left by Drosha cleavage and exports the pre-miRNA to the cytoplasm in a Ran-GTP dependent manner[54-60]. Once in the cytoplasm, both strands of the pre-miRNA can be cleaved by Dicer, another RNAse III enzyme, approximately two helical turns away from the base of the stem-loop[61-63]. The resulting ~22 mer RNA duplex is released by Dicer and a single stem-arm can be incorporated into RISC (RNA-induced silencing complex). RISC is a ribonucleoprotein complex that contains members of the Argonaute protein family and accessory factors, along with a miRNA and mRNA target. The relative thermal stabilities of the stem-arm duplex are thought to determine which strand becomes incorporated into RISC: the strand that enters RISC is often the one whose 5' end is less stable[64,65]. Translation inhibition is mediated by miRNA complementarity to target sequence(s) within the 3' UTR of the target mRNA by an as yet unknown mechanism[66,67]. Generally, imperfect complementarity results in translation suppression while perfect or near-perfect complementarity results in mRNA cleavage[68]. Many aspects of miRNA biogenesis, trafficking, RISC assembly, and the mechanism of RISC function await clarification, however functional studies of specific miRNAs and genetic and biochemical analyses of miRNA pathway components have shown that miRNAs are important in diverse biological processes.

I.B. miRNAs in Development

The development of a multicellular organism requires spatial and temporal control of genetic pathways. miRNAs are proposed to control or fine-tune those complex genetic pathways by post-transcriptional regulation of target genes. One approach to determine the necessity of miRNAs in animal development has been to create mutations in Dicer, an upstream enzyme required for the processing miRNAs to their mature, active form. Vertebrates are believed to have only a single copy of Dicer, which is likely required to fully process all vertebrate miRNAs[62,63,69]. In mice, ablation of Dicer function resulted in lethality by embryonic day (E) 7.5[69]. The Dicer null mice did not express primitive streak marker T (brachyury), indicating that development was likely arrested before the body was configured during gastrulation. Decreased limb size and increased programmed cell death resulted from the conditional loss of Dicer function specifically in the mouse limb mesoderm[70]. Completely blocking miRNA formation in zebrafish by making maternal-zygotic Dicer mutants revealed that loss of miRNAs did not affect axis formation or patterning of many cell types in the embryos. However, morphogenesis during gastrulation, brain formation, somitogenesis, and heart development all proved abnormal, and resulted in lethality[71]. Collectively, the genetic analyses of Dicer function suggest that mature miRNAs are required for proper development. Studies that remove all miRNA function are informative, however they are also blunt tools and do not provide insight into the precise functions of specific miRNAs.

I.C. Biological Roles of Specific miRNAs

There is a growing amount of evidence that suggests miRNAs participate in diverse biological processes. In pancreatic islet cells, overexpression of miR-375 suppressed glucose-induced insulin secretion, while inhibiting endogenous miR-375 enhanced insulin secretion[72]. A similar overexpression and inhibition strategy identified a role for miR-143 in adipocyte differentiation through regulating ERK5 protein expression[73]. In another example, a polycistronic. miRNA gene coding for 5 miRNAs was linked to tumorigenesis[74]. Other functions for miRNAs have been proposed in hematopoiesis[75], neuronal differentiation[76,77], and the regulation of Hox gene expression[78,79].

There are now over 300 known human miRNAs, however only a handful has any assigned biological function. Studies of specific miRNAs are required for understanding the prevalence and importance of miRNA-mediated regulation in development and pathology. The presently disclosed subject matter provides for the first time a role for miRNAs in regulating muscle differentiation and proliferation.

I.D. miRNAs in Heart Development

Cardiogenesis requires precise control of different genetic programs, thus it is intriguing to speculate that differentially expressed cardiac-enriched miRNAs might help regulate those complex pathways. Such tissue-specific expression patterns are disclosed herein by the presently disclosed subject matter for several miRNAs. miR-1 and miR-133 are expressed in both skeletal and cardiac muscle tissue, while miR-208 is detected solely in cardiac muscle tissue. Prior to the present disclosure, the functions of these muscle-specific miRNAs were unclear.

I.E. miRNA Target Identification

Identifying the targets of specific miRNAs facilitates understanding their precise role in regulatory pathways. Most animal miRNAs are imperfectly complementary to their target site, which thwarts using simple homology searches to identify animal miRNA target sites. To overcome this obstacle, several computational methods have been developed that incorporate sequence conservation and characteristics of known miRNA targets as criteria to predict new animal miRNA targets[80-85]. For example, some algorithms take into account that the majority of miRNAs have exhibited high complementarity between the second and eighth nucleotide within validated target sites, which is called the 'seed' region. Other algorithms do not since, in some cases, complementarity at the 3' end of a miRNA can compensate for weak 5' end binding. These algorithms also rank predictions by target sequence conservation across two or more species relative to flanking regions. These types of computational approaches have successfully predicted some mammalian miRNA target sites. The predictions produced for any particular miRNA almost certainly contains false positives. However, the predictions are extremely useful as hypothesis generators. Any prediction can be verified experimentally and placed into a relevant biological context.

I.F. Significance

There are currently several active areas in miRNA research that seek to understand the precise molecular mechanisms behind miRNA-directed repression, to develop better tools for analyzing miRNA expression and identifying target sites, and to determine biologically relevant roles for specific miRNAs within regulatory pathways.

Heart development and pathology are intimately linked to the regulation of complex genetic pathways, and much effort has been expended in attempt to understand these pathways. Most studies have focused on the role of transcription factors and regulatory enhancer sequences required for cardiac gene transcription. The regulation of cardiac gene expression has proved quite complex, with individual cardiac genes being controlled by multiple independent enhancers that direct very restricted expression patterns in the heart. Potentially, miRNAs have dramatically increased this complexity even further by adding another layer of regulation at the post-transcriptional level. The presently disclosed subject matter provides, in part, a new understanding of how cardiac and skeletal muscle gene expression is regulated and discloses therapeutic and research applications for the discoveries. Further, the discoveries related to miRNA control of muscle differentiation and proliferation disclosed herein serve as a model for understanding the function of miRNAs in other pathways as well.

II. Definitions

For convenience, certain terms employed in the specification, examples, and appended claims are collected here. While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, the articles "a", "an", and "the" are used herein to refer to one or to more than one (i.e., to at least one) of the grammatical object of the article. By way of example, "an element" refers to one element or more than one element.

As used herein, the term "about", when referring to a value or to an amount of mass, weight, time, volume, concentration, or percentage is meant to encompass variations of in some embodiments ±20% or ±10%, in some embodiments ±5%, in some embodiments ±1%, in some embodiments ±0.5%, and in some embodiments ±0.1% from the specified amount, as such variations are appropriate to practice the presently disclosed subject matter. Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the terms "amino acid" and "amino acid residue" are used interchangeably and refer to any of the twenty naturally occurring amino acids, as well as analogs, derivatives, and congeners thereof; amino acid analogs having variant side chains; and all stereoisomers of any of the foregoing. Thus, the term "amino acid" is intended to embrace all molecules, whether natural or synthetic, which include both an amino functionality and an acid functionality and are capable of being included in a polymer of naturally occurring amino acids.

An amino acid can be formed upon chemical digestion (hydrolysis) of a polypeptide at its peptide linkages. The amino acid residues described herein are in some embodiments in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, abbreviations for amino acid residues are shown in tabular form presented hereinabove.

It is noted that all amino acid residue sequences represented herein by formulae have a left-to-right orientation in the conventional direction of amino terminus to carboxy terminus. In addition, the phrases "amino acid" and "amino acid residue" are broadly defined to include modified and unusual amino acids.

Furthermore, it is noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

As used herein, the term "cell" is used in its usual biological sense. In some embodiments, the cell is present in an organism, for example, a vertebrate subject. The cell can be eukaryotic (e.g., a myocyte, such as a skeletal myocyte or a cardiac myocyte) or prokaryotic (e.g. a bacterium). The cell can be of somatic or germ line origin, totipotent, pluripotent, or differentiated to any degree, dividing or non-dividing. The cell can also be derived from or can comprise a gamete or embryo, a stem cell, or a fully differentiated cell.

As used herein, the terms "host cells" and "recombinant host cells" are used interchangeably and refer to cells (for example, myocytes) into which the compositions of the presently disclosed subject matter (for example, an expression vector encoding an miRNA) can be introduced. Furthermore, the terms refer not only to the particular cell into which an expression construct is initially introduced, but also to the progeny or potential progeny of such a cell. Because certain modifications can occur in succeeding generations due to either mutation or environmental influences, such progeny might not, in fact, be identical to the parent cell, but are still included within the scope of the term as used herein.

As used herein, the term "gene" refers to a nucleic acid that encodes an RNA, for example, nucleic acid sequences including, but not limited to, structural genes encoding a polypeptide. The term "gene" also refers broadly to any segment of DNA associated with a biological function. As such, the term "gene" encompasses sequences including but not limited to: a coding sequence; a promoter region; a transcriptional regulatory sequence; a non-expressed DNA segment that is a specific recognition sequence for regulatory proteins; a non-expressed DNA segment that contributes to gene expression, such as for example a DNA segment that can be transcribed into a 3' untranslated region of an mRNA, which is in turn targeted and bound by exemplary miRNAs of the presently disclosed subject matter; a DNA segment designed to have desired parameters; or combinations thereof. A gene can be obtained by a variety of methods, including cloning from a biological sample, synthesis based on known or predicted sequence information, and recombinant derivation from one or more existing sequences.

As is understood in the art, a gene typically comprises a coding strand and a non-coding strand. As used herein, the terms "coding strand" and "sense strand" are used interchangeably, and refer to a nucleic acid sequence that has the same sequence of nucleotides as an mRNA from which the gene product is translated. As is also understood in the art, when the coding strand and/or sense strand is used to refer to a DNA molecule, the coding/sense strand includes thymidine residues instead of the uridine residues found in the corresponding mRNA. Additionally, when used to refer to a DNA molecule, the coding/sense strand can also include additional elements not found in the mRNA including, but not limited to promoters, enhancers, and introns. Similarly, the terms "template strand" and "antisense strand" are used interchangeably and refer to a nucleic acid sequence that is complementary to the coding/sense strand. It should be noted, however, that for those genes that do not encode polypeptide products, for example an miRNA gene, the term "coding strand" is used to refer to the strand comprising the miRNA. In this usage, the strand comprising the miRNA is a sense strand with respect to the miRNA precursor, but it would be antisense with respect to its target RNA (i.e., the miRNA hybridizes to the target RNA because it comprises a sequence that is antisense to the target RNA).

As used herein, the terms "complementarity" and "complementary" refer to a nucleic acid that can form one or more hydrogen bonds with another nucleic acid sequence by either traditional Watson-Crick or other non-traditional types of interactions. In reference to the nucleic molecules of the presently disclosed subject matter, the binding free energy for a nucleic acid molecule with its complementary sequence is sufficient to allow the relevant function of the nucleic acid to proceed, in some embodiments, ribonuclease activity. For example, the degree of complementarity between the sense and antisense strands of an miRNA precursor can be the same or different from the degree of complementarity between the miRNA-containing strand of an miRNA precursor and the target nucleic acid sequence. Determination of binding free energies for nucleic acid molecules is well known in the art. See e.g., Freler et al., 1986[31]; Turner et al., 1987[32].

As used herein, the phrase "percent complementarity", "percent identity", and "percent identical" are used interchangeably herein and refer to the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). The terms "100% complementary", "fully complementary", and "perfectly complementary" indicate that all of the contiguous residues of a nucleic acid sequence can hydrogen bond with the same number of contiguous residues in a second nucleic acid sequence. As miRNAs are about 17-24 nt, and up to 5 mismatches (e.g., 1, 2, 3, 4, or 5 mismatches) are typically tolerated during miRNA-directed modulation of gene expression, a percent complementarity of at least about 70% between an miRNA and the RNA to which it is targeted should be sufficient for the miRNA to modulate the expression of the gene from which the target RNA was derived.

The term "gene expression" generally refers to the cellular processes by which a biologically active polypeptide is produced from a DNA sequence and exhibits a biological activity in a cell. As such, gene expression involves the processes of transcription and translation, but also involves post-transcriptional and post-translational processes that can influence a biological activity of a gene or gene product. These processes include, but are not limited to RNA synthesis, processing, and transport, as well as polypeptide synthesis, transport, and post-translational modification of polypeptides. Additionally, processes that affect protein-protein interactions within the cell can also affect gene expression as defined herein.

However, in the case of genes that do not encode protein products, for example miRNA genes, the term "gene expression" refers to the processes by which a precursor miRNA is produced from the gene. Typically, this process is referred to as transcription, although unlike the transcription directed by RNA polymerase II for protein-coding genes, the transcription products of an miRNA gene are not translated to produce a protein. Nonetheless, the production of a mature miRNA from an miRNA gene is encompassed by the term "gene expression" as that term is used herein.

As used herein, the term "isolated" refers to a molecule substantially free of other nucleic acids, proteins, lipids, carbohydrates, and/or other materials with which it is normally associated, such association being either in cellular material or in a synthesis medium. Thus, the term "isolated nucleic acid" refers to a ribonucleic acid molecule or a deoxyribonucleic acid molecule (for example, a genomic DNA, cDNA, mRNA, miRNA, etc.) of natural or synthetic origin or some combination thereof, which (1) is not associated with the cell in which the "isolated nucleic acid" is found in nature, or (2) is operatively linked to a polynucleotide to which it is not linked in nature. Similarly, the term "isolated polypeptide" refers to a polypeptide, in some embodiments prepared from recombinant DNA or RNA, or of synthetic origin, or some combination thereof, which (1) is not associated with proteins that it is normally found with in nature, (2) is isolated from the cell in which it normally occurs, (3) is isolated free of other proteins from the same cellular source, (4) is expressed by a cell from a different species, or (5) does not occur in nature.

The term "isolated", when used in the context of an "isolated cell", refers to a cell that has been removed from its natural environment, for example, as a part of an organ, tissue, or organism.

As used herein, the terms "label" and "labeled" refer to the attachment of a moiety, capable of detection by spectroscopic, radiologic, or other methods, to a probe molecule. Thus, the terms "label" or "labeled" refer to incorporation or attachment, optionally covalently or non-covalently, of a detectable marker into a molecule, such as a polypeptide. Various methods of labeling polypeptides are known in the art and can be used. Examples of labels for polypeptides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for antibodies, metal binding domains, epitope tags). In some embodiments, labels are attached by spacer arms of various lengths to reduce potential steric hindrance.

As used herein, the term "modulate" refers to an increase, decrease, or other alteration of any, or all, chemical and biological activities or properties of a biochemical entity. For example, the term "modulate" can refer to a change in the expression level of a gene or a level of an RNA molecule or equivalent RNA molecules encoding one or more proteins or protein subunits; or to an activity of one or more proteins or protein subunits that is upregulated or downregulated, such that expression, level, or activity is greater than or less than that observed in the absence of the modulator. For example, the term "modulate" can mean "inhibit" or "suppress", but the use of the word "modulate" is not limited to this definition.

The term "modulation" as used herein refers to both upregulation activation or stimulation) and downregulation (i.e., inhibition or suppression) of a response. Thus, the term "modulation", when used in reference to a functional property or biological activity or process (e.g., enzyme activity or receptor binding), refers to the capacity to upregulate (e.g., activate or stimulate), downregulate (e.g., inhibit or suppress), or otherwise change a quality of such property, activity, or process. In certain instances, such regulation can be contingent on the occurrence of a specific event, such as activation of a signal transduction pathway, and/or can be manifest only in particular cell types.

The term "modulator" refers to a polypeptide, nucleic acid, macromolecule, complex, molecule, small molecule, compound, species, or the like (naturally occurring or non-naturally occurring), or an extract made from biological materials such as bacteria, plants, fungi, or animal cells or tissues, that can be capable of causing modulation. Modulators can be evaluated for potential activity as inhibitors or activators (directly or indirectly) of a functional property, biological activity or process, or a combination thereof (e.g., agonist, partial antagonist, partial agonist, inverse agonist, antagonist, antimicrobial agents, inhibitors of microbial infection or proliferation, and the like), by inclusion in assays. In such assays, many modulators can be screened at one time. The activity of a modulator can be known, unknown, or partially known.

Modulators can be either selective or non-selective. As used herein, the term "selective" when used in the context of a modulator (e.g. an inhibitor) refers to a measurable or otherwise biologically relevant difference in the way the modulator interacts with one molecule (e.g. a target RNA of interest) versus another similar but not identical molecule (e.g. an RNA derived from a member of the same gene family as the target RNA of interest).

It must be understood that for a modulator to be considered a selective modulator, the nature of its interaction with a target need not entirely exclude its interaction with other molecules related to the target (e.g. transcripts from family members other than the target itself). Stated another way, the term selective modulator is not intended to be limited to those molecules that only bind to mRNA transcripts from a gene of interest and not to those of related family members. The term is also intended to include modulators that can interact with transcripts from genes of interest and from related family members, but for which it is possible to design conditions under which the differential interactions with the targets versus the family members has a biologically relevant outcome. Such conditions can include, but are not limited to differences in the degree of sequence identity between the modulator and the family members, and the use of the modulator in a specific tissue or cell type that expresses some but not all family members. Under the latter set of conditions, a modulator might be considered selective to a given target in a given tissue if it interacts with that target to cause a biologically relevant effect despite the fact that in another tissue that expresses additional family members the modulator and the target would not interact to cause a biological effect at all because the modulator would be "soaked out" of the tissue by the presence of other family members.

When a selective modulator is identified, the modulator binds to one molecule (for example an mRNA transcript of a gene of interest) in a manner that is different (for example, stronger) from the way it binds to another molecule (for example, an mRNA transcript of a gene related to the gene of interest). As used herein, the modulator is said to display "selective binding" or "preferential binding" to the molecule to which it binds more strongly as compared to some other possible molecule to which the modulator might bind.

As used herein, the terms "inhibit", "suppress", "down regulate", and grammatical variants thereof are used interchangeably and refer to an activity whereby gene product (e.g., a polypeptide), expression of a gene, activity of a polynucleotide, such as for example an miRNA, or a level of an RNA encoding one or more gene products is reduced below that observed in the absence of an implementation of an approach of the presently disclosed subject matter.

In some embodiments, inhibition with an miRNA molecule results in a decrease in the steady state expression level of a target RNA. In some embodiments, inhibition with an miRNA molecule results in an expression level of a target gene that is below that level observed in the presence of an inactive or attenuated molecule that is unable to downregulate the expression level of the target. In some embodiments, inhibition of gene expression with an miRNA molecule of the presently disclosed subject matter is greater in the presence of the miRNA molecule than in its absence. In some embodiments, inhibition of gene expression is associated with an enhanced rate of degradation of the mRNA encoded by the gene (for example, by miRNA-mediated inhibition of gene expression). In some embodiments, inhibition with an miRNA molecule of the presently disclosed subject matter results in an expression level of a gene product from a target gene that is below that level observed in the absence of the miRNA.

In some embodiments, an miRNA, such as for example an endogenous miRNA, can be inhibited by an miRNA inhibitor, resulting in an increase in expression of a gene targeted by the miRNA, as compared to the level of gene expression (e.g., production of a gene product) when the miRNA is not inhibited. As used herein, the terms "miRNA inhibitor" and "inhibitor of miRNA" are used interchangeably and refer to a molecule that inhibits activity of an miRNA.

In some embodiments, an miRNA inhibitor is a polynucleotide that hybridizes to a particular target miRNA under specified conditions, thereby inhibiting activity of the target miRNA. Conditions under which the miRNA inhibitor can hybridize to the target miRNA include, for example, physiological conditions. The miRNA inhibitor can hybridize to the target miRNA to a greater or lesser degree based on complementarity of the miRNA inhibitor polynucleotide sequence to the target miRNA polynucleotide. In some embodiments, the miRNA can be fully complementary to all or a portion of the target miRNA, or less than fully complementary, including for example, 99%, 98%, 97%, 96%, 95%, 90%, 80%, or 70% complementary to the target miRNA, depending on the particular application and need for specificity, as would be generally understood by one of skill in the art. The miRNA inhibitor need only share complementary with the target miRNA as is necessary to inhibit a desired amount of target miRNA activity under a particular set of conditions. Examples of miRNA inhibitors useful with the presently disclosed subject matter include, but are not limited to, modified polynucleotides such as 2'-O-methyl polynucleotides. Representative, non-limiting examples are set forth in Tables 2 and 3, and include 2'-O-methyl-miR-1, 2'-O-methyl-miR-133, and 2'-O-methyl-miR-208, which can specifically inhibit the activity of miR-1, miR-133, or miR-208, respectively.

As used herein, the term "mutation" carries its traditional connotation and refers to a change, inherited, naturally occurring, or introduced, in a nucleic acid or polypeptide sequence, and is used in its sense as generally known to those of skill in the art.

As used herein, the term "myocyte" refers broadly to all classifications of muscle cells at all stages of development. Thus, "myocyte" encompasses both undifferentiated muscle cells, such as for example myoblasts, as well as differentiated muscle cells, such as for example terminally differentiated myotubes. "Myocyte" also encompasses muscle cells of varying histological types, including but not limited to striated muscle cells (e.g., skeletal muscle cells), smooth muscle cells (e.g., intestinal muscle cells), and cardiac muscle cells. Further, "myocyte" as used herein is not species specific.

The term "naturally occurring", as applied to an object, refers to the fact that an object can be found in nature. For example, a polypeptide or polynucleotide sequence that is present in an organism (including bacteria) that can be isolated from a source in nature and which has not been intentionally modified by man in the laboratory is naturally occurring. It must be understood, however, that any manipulation by the hand of man can render a "naturally occurring" object an "isolated" object as that term is used herein.

As used herein, the terms "nucleic acid", "polynucleotide", and "nucleic acid molecule" refer to any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids can comprise monomers that are naturally occurring nucleotides (such as deoxyribonucleotides and ribonucleotides), or analogs of naturally occurring nucleotides (e.g., α-enantiomeric forms of naturally occurring nucleotides), or a combination of both. Modified nucleotides can have modifications in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as azasugars and carbocyclic sugar analogs. Examples of modifications in a base moiety include alkylated purines and pyrimidines, acylated purines or pyrimidines, or other well-known heterocyclic substitutes.

Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid" also includes so-called "peptide nucleic acids", which comprise naturally occurring or modified nucleic acid bases attached to a polyamide backbone. Nucleic acids can be either single stranded or double stranded.

The term "operatively linked", when describing the relationship between two nucleic acid regions, refers to a juxtaposition wherein the regions are in a relationship permitting them to function in their intended manner. For example, a control sequence "operatively linked" to a coding sequence can be ligated in such a way that expression of the coding sequence is achieved under conditions compatible with the control sequences, such as when the appropriate molecules (e.g., inducers and polymerases) are bound to the control or regulatory sequence(s). Thus, in some embodiments, the phrase "operatively linked" refers to a promoter connected to a coding sequence in such a way that the transcription of that coding sequence is controlled and regulated by that promoter. Techniques for operatively linking a promoter to a coding sequence are known in the art; the precise orientation and location relative to a coding sequence of interest is dependent, inter alia, upon the specific nature of the promoter.

Thus, the term "operatively linked" can refer to a promoter region that is connected to a nucleotide sequence in such a way that the transcription of that nucleotide sequence is controlled and regulated by that promoter region. Similarly, a nucleotide sequence is said to be under the "transcriptional control" of a promoter to which it is operatively linked. Techniques for operatively linking a promoter region to a nucleotide sequence are known in the art.

The term "operatively linked" can also refer to a transcription termination sequence that is connected to a nucleotide sequence in such a way that termination of transcription of that nucleotide sequence is controlled by that transcription termination sequence. In some embodiments, a transcription termination sequence comprises a sequence that causes transcription by an RNA polymerase III to terminate at the third or fourth T in the terminator sequence, TTTTTTT. Therefore, the nascent small transcript typically has 3 or 4 U's at the 3' terminus.

The phrases "percent identity" and "percent identical," in the context of two nucleic acid or protein sequences, refer to two or more sequences or subsequences that have in some embodiments at least 60%, in some embodiments at least 70%, in some embodiments at least 80%, in some embodiments at least 85%, in some embodiments at least 90%, in some embodiments at least 95%, in some embodiments at least 96%, in some embodiments at least 97%, in some embodiments at least 98%, and in some embodiments at least 99% nucleotide or amino acid residue identity, when compared and aligned for maximum correspondence, as measured using one of the following sequence comparison algorithms or by visual inspection. The percent identity exists in some embodiments over a region of the sequences that is at least about 10 residues in length, in some embodiments over a region that is at least about 20 residues in length, in some embodiments over a region of the sequences that is at least about 50 residues in length, in some embodiments over a region of at least about 100 residues, and in some embodiments the percent identity exists over at least about 150 residues. In some embodiments, the percent identity exists over the entire length of a given region, such as a coding region or an entire miRNA.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm described in Smith & Waterman, 1981[33], by the homology alignment algorithm described in Needleman & Wunsch, 1970[34], by the search for similarity method described in Pearson & Lipman, 1988[35], by computerized implementations of these algorithms (GAP, BESTFIT, FASTA, and TFASTA in the GCG® WISCONSIN PACKAGE®, available from Accelrys, Inc., San Diego, Calif., United States of America), or by visual inspection. See generally, Ausubel et al., 1989[36].

One example of an algorithm that is suitable for determining percent sequence identity and sequence similarity is the BLAST algorithm, which is described in Altschul et al., 1990[37]. Software for performing BLAST analyses is publicly available through the National Center for Biotechnology Information via the World Wide Web. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold[37]. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix.[38]

In addition to calculating percent sequence identity, the BLAST algorithm also performs a statistical analysis of the similarity between two sequences. See e.g., Karlin & Altschul 1993[39]. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in some embodiments less than about 0.1, in some embodiments less than about 0.01, and in some embodiments less than about 0.001.

The term "substantially identical", in the context of two nucleotide sequences, refers to two or more sequences or subsequences that have in some embodiments at least about 70% nucleotide identity, in some embodiments at least about 75% nucleotide identity, in some embodiments at least about 80% nucleotide identity, in some embodiments at least about 85% nucleotide identity, in some embodiments at least about 90% nucleotide identity, in some embodiments at least about 95% nucleotide identity, in some embodiments at least about 97% nucleotide identity, and in some embodiments at least about 99% nucleotide identity, when compared and aligned for maximum correspondence, as measured using one of the following sequence comparison algorithms or by visual inspection. In one example, the substantial identity exists in nucleotide sequences of at least 17 residues, in some embodiments in nucleotide sequence of at least about 18 residues, in some embodiments in nucleotide sequence of at least about 19 residues, in some embodiments in nucleotide sequence of at least about 20 residues, in some embodiments in nucleotide sequence of at least about 21 residues, in some embodiments in nucleotide sequence of at least about 22 residues, in some embodiments in nucleotide sequence of at least about 23 residues, in some embodiments in nucleotide sequence of at least about 24 residues, in some embodiments in nucleotide sequence of at least about 25 residues, in some embodiments in nucleotide sequence of at least about 26 residues, in some embodiments in nucleotide sequence of at least about 27 residues, in some embodiments in nucleotide sequence of at least about 30 residues, in some embodiments in nucleotide sequence of at least about 50 residues, in some embodiments in nucleotide sequence of at least about 75 residues, in some embodiments in nucleotide sequence of at least about 100 residues, in some embodiments in nucleotide sequences of at least about 150 residues, and in yet another example in nucleotide sequences comprising complete coding sequences. In some embodiments, polymorphic sequences can be substantially identical sequences. The term "polymorphic" refers to the occurrence of two or more genetically determined alternative sequences or alleles in a population. An allelic difference can be as small as one base pair. Nonetheless, one of ordinary skill in the art would recognize that the polymorphic sequences correspond to the same gene.

Another indication that two nucleotide sequences are substantially identical is that the two molecules specifically or substantially hybridize to each other under stringent conditions. In the context of nucleic acid hybridization, two nucleic acid sequences being compared can be designated a "probe sequence" and a "test sequence". A "probe sequence" is a reference nucleic acid molecule, and a "test sequence" is a test nucleic acid molecule, often found within a heterogeneous population of nucleic acid molecules.

An exemplary nucleotide sequence employed for hybridization studies or assays includes probe sequences that are complementary to or mimic in some embodiments at least an about 14 to 40 nucleotide sequence of a nucleic acid molecule of the presently disclosed subject matter. In one example, probes comprise 14 to 20 nucleotides, or even longer where desired, such as 30, 40, 50, 60, 100, 200, 300; or 500 nucleotides or up to the full length of a given gene. Such fragments can be readily prepared by, for example, directly synthesizing the fragment by chemical synthesis, by application of nucleic acid amplification technology, or by introducing selected sequences into recombinant vectors for recombinant production.

The phrase "targeted to" includes "hybridizing specifically to", which refers to the binding, duplexing, or hybridizing of a molecule only to a particular nucleotide sequence under stringent conditions when that sequence is present in a complex nucleic acid mixture (e.g., total cellular DNA or RNA).

By way of non-limiting example, hybridization can be carried out in 5×SSC, 4×SSC, 3×SSC, 2×SSC, 1×SSC, or 0.2×SSC for at least about 1 hour, 2 hours, 5 hours, 12 hours, or 24 hours (see Sambrook & Russell, 2001, for a description of SSC buffer and other hybridization conditions). The temperature of the hybridization can be increased to adjust the stringency of the reaction, for example, from about 25° C. (room temperature), to about 45° C., 50° C., 55° C., 60° C., or 65° C. The hybridization reaction can also include another agent affecting the stringency; for example, hybridization conducted in the presence of 50% formamide increases the stringency of hybridization at a defined temperature.

The hybridization reaction can be followed by a single wash step, or two or more wash steps, which can be at the same or a different salinity and temperature. For example, the temperature of the wash can be increased to adjust the stringency from about 25° C. (room temperature), to about 45° C., 50° C., 55° C., 60° C., 65° C., or higher. The wash step can be conducted in the presence of a detergent, e.g., SDS. For example, hybridization can be followed by two wash steps at 65° C. each for about 20 minutes in 2×SSC, 0.1% SDS, and optionally two additional wash steps at 65° C. each for about 20 minutes in 0.2×SSC, 0.1% SDS.

The following are examples of hybridization and wash conditions that can be used to clone homologous nucleotide sequences that are substantially identical to reference nucleotide sequences of the presently disclosed subject matter: a probe nucleotide sequence hybridizes in one example to a target nucleotide sequence in 7% sodium dodecyl sulfate (SDS), 0.5M NaPO$_4$, 1 mm ethylenediamine tetraacetic acid (EDTA) at 50° C. followed by washing in 2×SSC, 0.1% SDS at 50° C.; in some embodiments, a probe and test sequence hybridize in 7% sodium dodecyl sulfate (SDS), 0.5M NaPO$_4$, 1 mm EDTA at 50° C. followed by washing in 1×SSC, 0.1% SDS at 50° C.; in some embodiments, a probe and test sequence hybridize in 7% sodium dodecyl sulfate (SDS), 0.5M NaPO$_4$, 1 mm EDTA at 50° C. followed by washing in 0.5×SSC, 0.1% SDS at 50° C.; in some embodiments, a probe and test sequence hybridize in 7% sodium dodecyl sulfate (SDS), 0.5M NaPO$_4$, 1 mm EDTA at 50° C. followed by washing in 0.1×SSC, 0.1% SDS at 50° C.; in yet another example, a probe and test sequence hybridize in 7% sodium dodecyl sulfate (SDS), 0.5M NaPO$_4$, 1 mm EDTA at 50° C. followed by washing in 0.1×SSC, 0.1% SDS at 65° C.

Additional exemplary stringent hybridization conditions include overnight hybridization at 42° C. in a solution comprising or consisting of 50% formamide, 10×Denhardt's (0.2% Ficoll, 0.2% polyvinylpyrrolidone, 0.2% bovine serum albumin) and 200 mg/ml of denatured carrier DNA, e.g., sheared salmon sperm DNA, followed by two wash steps at 65° C. each for about 20 minutes in 2×SSC, 0.1% SDS, and two wash steps at 65° C. each for about 20 minutes in 0.2× SSC, 0.1% SDS.

Hybridization can include hybridizing two nucleic acids in solution, or a nucleic acid in solution to a nucleic acid attached to a solid support, e.g., a filter. When one nucleic acid is on a solid support, a prehybridization step can be conducted prior to hybridization. Prehybridization can be carried out for at least about 1 hour, 3 hours, or 10 hours in the same solution and at the same temperature as the hybridization (but without the complementary polynucleotide strand).

Thus, upon a review of the present disclosure, stringency conditions are known to those skilled in the art or can be determined by the skilled artisan without undue experimentation.[36, 40-44]

The phrase "hybridizing substantially to" refers to complementary hybridization between a probe nucleic acid molecule and a target nucleic acid molecule and embraces minor mismatches that can be accommodated by reducing the stringency of the hybridization media to achieve the desired hybridization.

The term "phenotype" refers to the entire physical, biochemical, and physiological makeup of a cell or an organism, e.g., having any one trait or any group of traits. As such, phenotypes result from the expression of genes within a cell or an organism, and relate to traits that are potentially observable or assayable.

As used herein, the terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. As used herein, the terms "protein", "polypeptide", and "peptide" are used interchangeably herein when referring to a gene product. The term "polypeptide" encompasses proteins of all functions, including enzymes. Thus, exemplary polypeptides include gene products, naturally occurring proteins, homologs, orthologs, paralogs, fragments, and other equivalents, variants and analogs of the foregoing.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. A fragment can retain one or more of the biological activities of the reference polypeptide. Further, fragments can include a sub-fragment of a specific region, which sub-fragment retains a function of the region from which it is derived.

As used herein, the term "primer" refers to a sequence comprising in some embodiments two or more deoxyribonucleotides or ribonucleotides, in some embodiments more than three, in some embodiments more than eight, and in some embodiments at least about 20 nucleotides of an exonic or intronic region. Such oligonucleotides are in some embodiments between ten and thirty bases in length.

The term "purified" refers to an object species that is the predominant species present (i.e., on a molar basis it is more abundant than any other individual species in the composition). A "purified fraction" is a composition wherein the object species comprises at least about 50 percent (on a molar basis) of all species present. In making the determination of the purity of a species in solution or dispersion, the solvent or matrix in which the species is dissolved or dispersed is usually not included in such determination; instead, only the species (including the one of interest) dissolved or dispersed are taken into account. Generally, a purified composition will have one species that comprises more than about 80 percent of all species present in the composition, more than about 85%, 90%, 95%, 99% or more of all species present. The object species can be purified to essential homogeneity (contaminant species cannot be detected in the composition by conventional detection methods) wherein the composition consists essentially of a single species. Purity of a polypeptide can be determined by a number of methods known to those of skill in the art, including for example, amino-terminal amino acid sequence analysis, gel electrophoresis, and mass-spectrometry analysis.

A "reference sequence" is a defined sequence used as a basis for a sequence comparison. A reference sequence can be a subset of a larger sequence, for example, as a segment of a full-length nucleotide or amino acid sequence, or can comprise a complete sequence. Because two proteins can each (1) comprise a sequence (i.e., a portion of the complete protein sequence) that is similar between the two proteins, and (2) can further comprise a sequence that is divergent between the two proteins, sequence comparisons between two (or more) proteins are typically performed by comparing sequences of the two proteins over a "comparison window" (defined hereinabove) to identify and compare local regions of sequence similarity.

The term "regulatory sequence" is a generic term used throughout the specification to refer to polynucleotide sequences, such as initiation signals, enhancers, regulators, promoters, and termination sequences, which are necessary or desirable to affect the expression of coding and non-coding sequences to which they are operatively linked. Exemplary regulatory sequences are described in Goeddel, 1990[45], and include, for example, the early and late promoters of simian virus 40 (SV40), adenovirus or cytomegalovirus immediate early promoter, the CMV minimal promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast a-mating factors, the polyhedron promoter of the baculovirus system and other sequences known to control the expression of genes of prokaryotic or eukaryotic cells or their viruses, and various combinations thereof. The nature and use of such control sequences can differ depending upon the host organism. In prokaryotes, such regulatory sequences generally include promoter, ribosomal binding site, and transcription termination sequences. The term "regulatory sequence" is intended to include, at a minimum, components the presence of which can influence expression, and can also include additional components the presence of which is advantageous, for example, leader sequences and fusion partner sequences.

In certain embodiments, transcription of a polynucleotide sequence is under the control of a promoter sequence (or other regulatory sequence) that controls the expression of the polynucleotide in a cell type in which expression is intended. It will also be understood that the polynucleotide can be under the control of regulatory sequences that are the same or different from those sequences which control expression of the naturally occurring form of the polynucleotide. In some embodiments, a promoter sequence is selected from the group consisting of a CMV minimal promoter, muscle creatine kinase (MCK), and an a-myosin heavy chain (MHC) promoter. For example, muscle creatine kinase (MCK) promoter, which directs gene expression in skeletal muscle, can be used to express miRNAs, such as for example, miR-1, miR-133 or miR-206 in tissue, including skeletal muscle using currently available transgenic techniques. It is understood that the entire promoter identified for any promoter (for example, the promoters listed herein) need not be employed, and that a functional derivative thereof can be used. As used herein, the phrase "functional derivative" refers to a nucleic acid sequence that comprises sufficient sequence to direct transcription of another operatively linked nucleic acid molecule. As such, a "functional derivative" can function as a minimal promoter, as that term is defined herein.

Termination of transcription of a polynucleotide sequence is typically regulated by an operatively linked transcription termination sequence (for example, an RNA polymerase III termination sequence). In certain instances, transcriptional terminators are also responsible for correct mRNA polyadenylation. The 3' non-transcribed regulatory DNA sequence includes from in some embodiments about 50 to about 1,000, and in some embodiments about 100 to about 1,000, nucleotide base pairs and contains transcriptional and translational termination sequences. In some embodiments, an RNA polymerase III termination sequence comprises the nucleotide sequence TTTTTTT.

The term "reporter gene" refers to a nucleic acid comprising a nucleotide sequence encoding a protein that is readily detectable either by its presence or activity, including, but not limited to, luciferase, fluorescent protein (e.g., green fluorescent protein), chloramphenicol acetyl transferase, β-galactosidase, secreted placental alkaline phosphatase, 3-lactamase, human growth hormone, and other secreted enzyme reporters. Generally, a reporter gene encodes a polypeptide not otherwise produced by the host cell, which is detectable by analysis of the cell(s), e.g., by the direct fluorometric, radioisotopic or spectrophotometric analysis of the cell(s) and typically without the need to kill the cells for signal analysis. In certain instances, a reporter gene encodes an enzyme, which produces a change in fluorometric properties of the host cell, which is detectable by qualitative, quantitative, or semiquantitative function or transcriptional activation. Exemplary enzymes include esterases, β-lactamase, phosphatases, peroxidases, proteases (tissue plasminogen activator or urokinase), and other enzymes whose function can be detected by appropriate chromogenic or fluorogenic substrates known to those skilled in the art or developed in the future.

As used herein, the term "sequencing" refers to determining the ordered linear sequence of nucleic acids or amino acids of a DNA, RNA, or protein target sample, using conventional manual or automated laboratory techniques.

As used herein, the term "substantially pure" refers to that the polynucleotide or polypeptide is substantially free of the sequences and molecules with which it is associated in its natural state, and those molecules used in the isolation procedure. The term "substantially free" refers to that the sample is in some embodiments at least 50%, in some embodiments at least 70%, in some embodiments 80% and in some embodiments 90% free of the materials and compounds with which is it associated in nature.

As used herein, the term "target cell" refers to a cell, into which it is desired to insert a nucleic acid sequence or polypeptide, or to otherwise effect a modification from conditions known to be standard in the unmodified cell. A nucleic acid sequence introduced into a target cell can be of variable length. Additionally, a nucleic acid sequence can enter a target cell as a component of a plasmid or other vector or as a naked sequence.

As used herein, the term "target gene" refers to a gene that is targeted for modulation using the methods and compositions of the presently disclosed subject matter. A target gene, therefore, comprises a nucleic acid sequence the expression level of which, either at the mRNA or polypeptide level, is downregulated by a miRNA. Similarly, the terms "target RNA" or "target mRNA" refers to the transcript of a target gene to which the miRNA is intended to bind, leading to modulation of the expression of the target gene. The target gene can be a gene derived from a cell, an endogenous gene, a transgene, or exogenous genes such as genes of a pathogen, for example a virus, which is present in the cell after infection thereof. The cell containing the target gene can be derived from or contained in any organism, for example a plant, animal, protozoan, virus, bacterium, or fungus.

As used herein, the term "transcription" refers to a cellular process involving the interaction of an RNA polymerase with a gene that directs the expression as RNA of the structural information present in the coding sequences of the gene. The process includes, but is not limited to, the following steps: (a) the transcription initiation; (b) transcript elongation; (c) transcript splicing; (d) transcript capping; (e) transcript termination; (f) transcript polyadenylation; (g) nuclear export of the transcript; (h) transcript editing; and (i) stabilizing the transcript.

As used herein, the term "transcription factor" refers to a cytoplasmic or nuclear protein which binds to a gene, or binds to an RNA transcript of a gene, or binds to another protein which binds to a gene or an RNA transcript or another protein which in turn binds to a gene or an RNA transcript, so as to thereby modulate expression of the gene. Such modulation can additionally be achieved by other mechanisms; the essence of a "transcription factor for a gene" pertains to a factor that alters the level of transcription of the gene in some way.

The term "transfection" refers to the introduction of a nucleic acid, e.g., an expression vector, into a recipient cell, which in certain instances involves nucleic acid-mediated gene transfer. The term "transformation" refers to a process in which a cell's genotype is changed as a result of the cellular uptake of exogenous nucleic acid. For example, a transformed cell can express an miRNA of the presently disclosed subject matter.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed as a "p-value". Those p-values that fall below a user-defined cutoff point are regarded as significant. In one example, a p-value less than or equal to 0.05, in some embodiments less than 0.01, in some embodiments less than 0.005, and in some embodiments less than 0.001, are regarded as significant.

As used herein, the phrase "target RNA" refers to an RNA molecule (for example, an mRNA molecule encoding a gene product) that is a target for modulation. In some embodiments the target RNA is encoded by a target gene. Similarly, the phrase "target site" refers to a sequence within a target RNA that is "targeted" for cleavage mediated by an miRNA construct that contains sequences within its antisense strand that are complementary to the target site. Also similarly, the phrase "target cell" refers to a cell that expresses a target RNA and into which an miRNA is intended to be introduced. A target cell is in some embodiments a myocyte.

An miRNA is "targeted to" an RNA molecule if it has sufficient nucleotide similarity to the RNA molecule that it would be expected to modulate the expression of the RNA molecule under conditions sufficient for the miRNA and the RNA molecule to interact. In some embodiments, the interaction occurs within a myocyte. In some embodiments the interaction occurs under physiological conditions. As used herein, the phrase "physiological conditions" refers to in vivo conditions within a myocyte, whether that myocyte is part of a subject or a subject's tissue, or that myocyte is being grown in vitro. Thus, as used herein, the phrase "physiological conditions" refers to the conditions within a myocyte under any conditions that the myocyte can be exposed to, either as part of a subject or when grown in vitro.

As used herein, the phrase "detectable level of cleavage" refers to a degree of cleavage of target RNA (and formation of cleaved product RNAs) that is sufficient to allow detection of cleavage products above the background of RNAs produced by random degradation of the target RNA. Production of miRNA-mediated cleavage products from at least 1-5% of the target RNA is sufficient to allow detection above background for most detection methods.

The terms "microRNA" and "miRNA" are used interchangeably and refer to a nucleic acid molecule of about 17-24 nucleotides that is produced from a pri-miRNA, a pre-miRNA, or a functional equivalent. miRNAs are to be contrasted with short interfering RNAs (siRNAs), although in the context of exogenously supplied miRNAs and siRNAs, this distinction might be somewhat artificial. The distinction to keep in mind is that an miRNA is necessarily the product of nuclease activity on a hairpin molecule such as has been described herein, and an siRNA can be generated from a fully double-stranded RNA molecule or a hairpin molecule. Further information related to miRNAs generally, as well as a database of known published miRNAs and searching tools for mining the database can be found at the Wellcome Trust Sanger Institute miRBase::Sequences website, herein incorporated by reference. See also *The microRNA Registry*, Griffiths-Jones S., NAR, 2004, 32, Database Issue, D109-D111, herein incorporated by reference.

As used herein, the term "RNA" refers to a molecule comprising at least one ribonucleotide residue. By "ribonucleotide" is meant a nucleotide with a hydroxyl group at the 2' position of a β-D-ribofuranose moiety. The terms encompass double stranded RNA, single stranded RNA, RNAs with both double stranded and single stranded regions, isolated RNA such as partially purified RNA, essentially pure RNA, synthetic RNA, and recombinantly produced RNA. Thus, RNAs include, but are not limited to mRNA transcripts, miRNAs and miRNA precursors, and siRNAs. As used herein, the term "RNA" is also intended to encompass altered RNA, or analog RNA, which are RNAs that differ from naturally occurring RNA by the addition, deletion, substitution, and/or alteration of one or more nucleotides. Such alterations can include addition of non-nucleotide material, such as to the end(s) of the RNA or internally, for example at one or more nucleotides of the RNA. Nucleotides in the RNA molecules of the presently disclosed subject matter can also comprise non-standard nucleotides, such as non-naturally occurring nucleotides or chemically synthesized nucleotides or deoxynucleotides. These altered RNAs can be referred to as analogs or analogs of a naturally occurring RNA.

As used herein, the phrase "double stranded RNA" refers to an RNA molecule at least a part of which is in Watson-Crick base pairing forming a duplex. As such, the term is to be understood to encompass an RNA molecule that is either fully or only partially double stranded. Exemplary double stranded RNAs include, but are not limited to molecules comprising at least two distinct RNA strands that are either partially or fully duplexed by intermolecular hybridization. Additionally, the term is intended to include a single RNA molecule that by intramolecular hybridization can form a double stranded region (for example, a hairpin). Thus, as used herein the phrases "intermolecular hybridization" and "intramolecular hybridization" refer to double stranded molecules for which the nucleotides involved in the duplex formation are present on different molecules or the same molecule, respectively.

As used herein, the phrase "double stranded region" refers to any region of a nucleic acid molecule that is in a double stranded conformation via hydrogen bonding between the nucleotides including, but not limited to hydrogen bonding between cytosine and guanosine, adenosine and thymidine, adenosine and uracil, and any other nucleic acid duplex as would be understood by one of ordinary skill in the art. The length of the double stranded region can vary from about 15 consecutive basepairs to several thousand basepairs. In some embodiments, the double stranded region is at least 15 basepairs, in some embodiments between 15 and 300 basepairs, and in some embodiments between 15 and about 60 basepairs. As describe hereinabove, the formation of the double stranded region results from the hybridization of complementary RNA strands (for example, a sense strand and an antisense strand), either via an intermolecular hybridization (i.e., involving 2 or more distinct RNA molecules) or via an intramolecular hybridization, the latter of which can occur when a single RNA molecule contains self-complementary regions that are capable of hybridizing to each other on the same RNA molecule. These self-complementary regions are typically separated by a short stretch of nucleotides (for example, about 5-10 nucleotides) such that the intramolecular hybridization event forms what is referred to in the art as a "hairpin" or a "stem-loop structure".

III. Nucleic Acids

The nucleic acid molecules employed in accordance with the presently disclosed subject matter include nucleic acid molecules encoding a myocyte gene product, as well as the nucleic acid molecules that are used in accordance with the presently disclosed subject matter to modulate the expression of a myocyte gene (e.g., an miRNA nucleic acid molecule). Thus, the nucleic acid molecules employed in accordance with the presently disclosed subject matter include, but are not limited to, the nucleic acid molecules described herein. For example, the nucleic acid molecules employed herein include, but are not limited to miR-1 (UGGAAUGUAAA-GAAGUAUGUA; SEQ ID NO:1), miR-133 (UUGGUC-CCCUUCAACCAGCUGU; SEQ ID NO:2), miR-206 (UG-GAAUGUAAGGAAGUGUGUGG; SEQ ID NO:3), miR-208 (AUAAGACGAGCAAAAAGCUUGU; SEQ ID NO:4), miR-22 (AAGCUGCCAGUUGAAGAACUGU; SEQ ID NO:5), miR-26 (UUCAAGUAAUyCAGGAUAGGy(U); SEQ ID NO:6), miR-29 (UAGCACCAUyUGAAAUCrGU (kUU); SEQ ID NO:7), miR-30 (ykUwmAswysshhswyUvn-vv(bC); SEQ ID NO:8), miR-128 (UCACAGUGAACCG-GUCUCUUUy; SEQ ID NO:9), miR-143 (UGAGAUGAAGCACUGUAGCUCA; SEQ ID NO:10), and miR-145 (GUCCAGUUUUCCCAGGAAUCCCUU; SEQ ID NO:11); sequences substantially identical to those described herein (for example, in some embodiments, sequences at least 70%, 80%, 85%, 90%, 91%, 92%, 93%, 94%, 95%, 96%, 97%, 98%, or 99% identical to any of SEQ ID NOs: 1-11); and subsequences and elongated sequences thereof. The presently disclosed subject matter also encompasses genes, cDNAs, chimeric genes, and vectors comprising the disclosed nucleic acid sequences.

The one-letter nucleotide codes used above and elsewhere herein are in accordance with WIPO Standard ST.25 (1998), Appendix 2, Table 1, (M.P.E.P. 2422, Table 1), herein incorporated by reference. In particular, the following one-letter codes represent the associated nucleotide(s) as set forth in Table 1. Nucleotide(s) in parenthesis (e.g., (n)) is intended to mean the nucleotide(s) can be present or absent. Further, FIG. 21 lists individual sequences possible for SEQ ID NOs: 5-11 based on the nucleotide permutations set forth in SEQ ID NOs: 5-11.

TABLE 1

One-Letter Nucleotide Abbreviations

| | |
|---|---|
| A | adenine |
| G | guanine |
| C | cytosine |
| T | thymine |
| U | uracil |
| k | G or U/T |
| w | U/T or A |
| m | C or A |
| s | G or C |
| h | A, C, or U/T |
| v | G, A, or C |
| b | C, G, or U/T |
| n | A, G, C, or U/T |
| y | C or T/U |

An exemplary nucleotide sequence employed in the methods disclosed herein comprises sequences that are complementary to each other, the complementary regions being capable of forming a duplex of, in some embodiments, at least about 15 to 300 basepairs, and in some embodiments, at least about 15-24 basepairs. One strand of the duplex comprises a nucleic acid sequence of at least 15 contiguous bases having a nucleic acid sequence of a nucleic acid molecule of the presently disclosed subject matter. In one example, one strand of the duplex comprises a nucleic acid sequence comprising 15, 16, 17, or 18 nucleotides, or even longer where desired, such as 19, 20, 21, 22, 23, 24, 25, 26, 27, 28, 29, or 30 nucleotides, or up to the full length of any of those nucleic acid sequences described herein. Such fragments can be readily prepared by, for example, directly synthesizing the fragment by chemical synthesis, by application of nucleic acid amplification technology, or by introducing selected sequences into recombinant vectors for recombinant production. The phrase "hybridizing specifically to" refers to the binding, duplexing, or hybridizing of a molecule only to a particular nucleotide sequence under stringent conditions when that sequence is present in a complex nucleic acid mixture (e.g., total cellular DNA or RNA).

The term "subsequence" refers to a sequence of a nucleic acid molecule or amino acid molecule that comprises a part of a longer nucleic acid or amino acid sequence. An exemplary subsequence is a sequence that comprises part of a duplexed region of a pri-miRNA or a pre-miRNA ("miRNA precursors") including, but not limited to the nucleotides that become the mature miRNA after nuclease action or a single-stranded region in an miRNA precursor.

The term "elongated sequence" refers to an addition of nucleotides (or other analogous molecules) incorporated into the nucleic acid. For example, a polymerase (e.g., a DNA polymerase) can add sequences at the 3' terminus of the nucleic acid molecule. In addition, the nucleotide sequence can be combined with other DNA sequences, such as promoters, promoter regions, enhancers, polyadenylation signals, intronic sequences, additional restriction enzyme sites, multiple cloning sites, and other coding segments.

Nucleic acids of the presently disclosed subject matter can be cloned, synthesized, recombinantly altered, mutagenized, or subjected to combinations of these techniques. Standard recombinant DNA and molecular cloning techniques used to isolate nucleic acids are known in the art. Exemplary, non-limiting methods are described by Silhavy et al., 1984[46]; Ausubel et al., 1989[36]; Glover & Hames, 1995[47]; and Sambrook & Russell, 2001[40]. Site-specific mutagenesis to create base pair changes, deletions, or small insertions is also known in the art as exemplified by publications (see e.g., Adelman et al., 1983[48]; Sambrook & Russell, 2001[40]).

IV. miRNA-Expression Vectors

In some embodiments of the presently disclosed subject matter, miRNA molecules or miRNA precursor molecules are expressed from transcription units inserted into nucleic acid vectors (alternatively referred to generally as "recombinant vectors" or "expression vectors"). A vector can be used to deliver a nucleic acid molecule encoding an miRNA into a myocyte to target a specific gene. The recombinant vectors can be, for example, DNA plasmids or viral vectors. A variety of expression vectors are known in the art. The selection of the appropriate expression vector can be made on the basis of several factors including, but not limited to the cell type wherein expression is desired.

The term "vector" refers to a nucleic acid capable of transporting another nucleic acid to which it has been linked. Vectors include those capable of autonomous replication and expression of nucleic acids to which they are linked. Vectors capable of directing the expression of genes to which they are operatively linked are referred to herein as "expression vectors". In general, expression vectors of utility in recombinant techniques are often in the form of plasmids. However, the presently disclosed subject matter is intended to include such other forms of expression vectors which serve equivalent functions and which become known in the art subsequently hereto.

The term "expression vector" as used herein refers to a nucleotide sequence capable of directing expression of a particular nucleotide sequence in an appropriate host cell, comprising a promoter operatively linked to the nucleotide sequence of interest which is operatively linked to transcription termination sequences. It also typically comprises sequences required for proper translation of the nucleotide sequence. The construct comprising the nucleotide sequence of interest can be chimeric. The construct can also be one that is naturally occurring but has been obtained in a recombinant form useful for heterologous expression. The nucleotide sequence of interest, including any additional sequences designed to effect proper expression of the nucleotide sequences, can also be referred to as an "expression cassette".

The terms "heterologous gene", "heterologous DNA sequence", "heterologous nucleotide sequence", "exogenous nucleic acid molecule", or "exogenous DNA segment", as used herein, each refer to a sequence that originates from a source foreign to an intended host cell or, if from the same source, is modified from its original form. Thus, a heterologous gene in a host cell includes a gene that is endogenous to the particular host cell but has been modified, for example by mutagenesis or by isolation from native transcriptional regulatory sequences. The terms also include non-naturally occurring multiple copies of a naturally occurring nucleotide sequence. Thus, the terms can refer to a DNA segment that is foreign or heterologous to the cell, or homologous to the cell but in a position within the host cell nucleic acid wherein the element is not ordinarily found.

The term "promoter" or "promoter region" each refers to a nucleotide sequence within a gene that is positioned 5' to a coding sequence and functions to direct transcription of the coding sequence. The promoter region comprises a transcriptional start site, and can additionally include one or more transcriptional regulatory elements. In some embodiments, a method of the presently disclosed subject matter employs a RNA polymerase III promoter.

A "minimal promoter" is a nucleotide sequence that has the minimal elements required to enable basal level transcription to occur. As such, minimal promoters are not complete promoters but rather are subsequences of promoters that are capable of directing a basal level of transcription of a reporter construct in an experimental system. Minimal promoters include but are not limited to the cytomegalovirus (CMV) minimal promoter, the herpes simplex virus thymidine kinase (HSV-tk) minimal promoter, the simian virus 40 (SV40) minimal promoter, the human β-actin minimal promoter, the human EF2 minimal promoter, the adenovirus E1B minimal promoter, and the heat shock protein (hsp) 70 minimal promoter. Minimal promoters are often augmented with one or more transcriptional regulatory elements to influence the transcription of an operatively linked gene. For example, cell-type-specific or tissue-specific transcriptional regulatory elements can be added to minimal promoters to create recombinant promoters that direct transcription of an operatively linked nucleotide sequence in a cell-type-specific or tissue-specific manner. As used herein, the term "minimal promoter" also encompasses a functional derivative of a promoter disclosed herein, including, but not limited to an RNA polymerase III promoter (for example, an H1, 7SL, 5S, or U6 promoter), an adenovirus VA1 promoter, a Vault promoter, a telomerase RNA promoter, and a tRNA gene promoter.

Different promoters have different combinations of transcriptional regulatory elements. Whether or not a gene is expressed in a cell is dependent on a combination of the particular transcriptional regulatory elements that make up the gene's promoter and the different transcription factors that, are present within the nucleus of the cell. As such, promoters are often classified as "constitutive", "tissue-specific", "cell-type-specific", or "inducible", depending on their functional activities in vivo or in vitro. For example, a constitutive promoter is one that is capable of directing transcription of a gene in a variety of cell types (in some embodiments, in all cell types) of an organism. Exemplary constitutive promoters include the promoters for the following genes which encode certain constitutive or "housekeeping" functions: hypoxanthine phosphoribosyl transferase (HPRT), dihydrofolate reductase (DHFR; (Scharfmann et al., 1991), adenosine deaminase, phosphoglycerate kinase (PGK), pyruvate kinase, phosphoglycerate mutase, the β-actin promoter (see e.g., Williams et al., 1993), and other constitutive promoters known to those of skill in the art. "Tissue-specific" or "cell-type-specific" promoters, on the other hand, direct transcription in some tissues or cell types of an organism but are inactive in some or all others tissues or cell types. Exemplary tissue-specific promoters include those promoters described in more detail hereinbelow, as well as other tissue-specific and cell-type specific promoters known to those of skill in the art.

When used in the context of a promoter, the term "linked" as used herein refers to a physical proximity of promoter elements such that they function together to direct transcription of an operatively linked nucleotide sequence.

The term "transcriptional regulatory sequence" or "transcriptional regulatory element", as used herein, each refers to a nucleotide sequence within the promoter region that enables responsiveness to a regulatory transcription factor. Responsiveness can encompass a decrease or an increase in transcriptional output and is mediated by binding of the transcription factor to the nucleotide sequence comprising the transcriptional regulatory element. In some embodiments, a transcriptional regulatory sequence is a transcription termination sequence, alternatively referred to herein as a transcription termination signal.

The term "transcription factor" generally refers to a protein that modulates gene expression by interaction with the transcriptional regulatory element and cellular components for transcription, including RNA Polymerase, Transcription Associated Factors (TAFs), chromatin-remodeling proteins, and any other relevant protein that impacts gene transcription.

V. Methods for Modulating Gene Expression in Myocytes

The presently disclosed subject matter provides method for modulating expression of genes in myocytes with specificity. In some embodiments, the methods comprise contacting a myocyte with a miRNA or a vector encoding the miRNA targeted to a gene in the myocyte. Targeting one or more particular genes in myocyte allows for manipulation of myocyte function or development (e.g., differentiation) with a high level of specificity. Thus, in some embodiments, the presently disclosed subject matter further provides methods for modulating myocyte function or development by contacting a myocyte with an miRNA targeted to a gene in the myocyte that can modulate myocyte function or development.

In some embodiments, the miRNA targeted to a particular gene is selected from the group consisting of miR-1, miR-133, miR-206, miR-208, miR-22, miR-26, miR-29, miR-30, miR-128, miR-143, and miR-145 (SEQ ID NOs: 1-11, respectively), including miRNAs having sequences at least about 70%, 80%, 85%, 90%, 91%, 92%, 93%, 94%, 95%, 96%, 97%, 98%, or 99% identical to the sequences set forth in any one of SEQ ID NOs 1-11.

An miRNA is "targeted to" an RNA molecule if it has sufficient nucleotide similarity to the RNA molecule that it would be expected to modulate the expression of the RNA molecule under conditions sufficient for the miRNA and the RNA molecule to interact. In some embodiments, the interaction occurs within a myocyte. In some embodiments the interaction occurs under physiological conditions. As used herein, the phrase "physiological conditions" refers to in vivo conditions within a myocyte, whether that myocyte is part of a subject or a subject's tissue, or that myocyte is being grown in vitro. Thus, as used herein, the phrase "physiological conditions" refers to the conditions within a myocyte under any conditions that the myocyte can be exposed to, either as part of an organism or when grown in vitro.

In some embodiments, the targeted gene is a myocyte differentiation gene or a myocyte proliferation gene and when expressed can modulate myocyte differentiation and/or proliferation, respectively. In some embodiments, the targeted gene can express a gene product that inhibits myocyte differentiation and/or proliferation. Thus, targeted inhibition of expression of one or more of these differentiation and/or proliferation target genes by the miRNA can result in an increase in differentiation and/or proliferation of the treated myocyte. In non-limiting exemplary embodiments of the presently disclosed subject matter, the myocyte differentiation gene can encode a histone deacetylase 4 (HDAC4) polypeptide or a thyroid hormone receptor protein 240 (TRAP240) and the myocyte proliferation gene can encode a serum response factor (SRF) polypeptide.

Expression of one or more of the myocyte differentiation or proliferation genes can be targeted for inhibition utilizing one of the miRNAs disclosed herein. For example, the miRNAs miR-1 and miRNA-133 each specifically target the 3' untranslated region of HDAC4 and SRF, respectively, and inhibit expression of the gene products encoded by these genes. Thus, in some embodiments of the presently disclosed subject matter, differentiation of a myocyte can be increased by contacting the myocyte with miR-1, which targets the gene encoding HDAC4, thereby substantially preventing expression of HDAC4 and increasing myocyte differentiation. Likewise, in some embodiments of the presently disclosed subject matter, proliferation of a myocyte can be increased by contacting the myocyte with miR-133, which targets the gene encoding SRF, thereby substantially preventing expression of SRF and increasing myocyte proliferation.

VI. Therapeutic Methods

The presently disclosed subject matter provides in some embodiments therapeutic methods for treating a muscle injury in a subject. As disclosed herein, miRNAs can be targeted to genes to modulate expression of the genes. In particular, genes expressing products that function to inhibit myocyte differentiation and/or proliferation can be targeted by miRNAs to inhibit expression of these genes, resulting in increased myocyte differentiation and/or proliferation. Further, miRNA inhibitors can be targeted to endogenous miRNAs to facilitate in relative increase in expression of particular gene products in a manner beneficial to treatment of the muscle injury. Additionally, combinations of miRNAs and/or miRNA inhibitors can be co-administered to the muscle injury in an approach to optimize healing of the injury. Increased myocyte differentiation and/or proliferation can be beneficial in healing damaged muscle tissue or stimulating regrowth of lost muscle tissue.

Thus, in some embodiments of the presently disclosed subject matter, methods for treating a muscle injury in a subject comprise administering to a muscle injury site in a subject an effective amount of a miRNA, a vector encoding the miRNA, an inhibitor of an miRNA, or combinations thereof, wherein the miRNA is targeted to a gene in a myocyte at the muscle injury site.

Muscle development, and comparably muscle growth and/or healing, such as after injury, can occur in phases. Representative phases include undifferentiated myocyte proliferation, followed by differentiation of the myocytes into mature cells of the muscle tissue. Thus, repair of muscle tissue at a site of muscle injury can be facilitated by the coordinated administration to the injury site of miRNAs and/or miRNA inhibitors that enhance proliferation of undifferentiated myocytes, and the administration to the injury site of miRNAs and/or miRNA inhibitors that enhance differentiation of the proliferated myocytes into mature functioning muscle tissue.

For example, as disclosed herein, it has been determined that miR-1 and miR-133 each play distinct roles in modulating skeletal muscle proliferation and differentiation. miR-133 enhances myocyte proliferation by repressing SRF. In contrast, miR-1 promotes myocyte differentiation by targeting HDAC4, a transcriptional repressor of muscle gene expression. Thus, in a non-limiting representative embodiment of the presently disclosed subject matter, miR-133 and an inhibitor of miR-1 (e.g., 2'-O-methyl-miR-1) are first co-administered to the muscle injury site at a first time point to increase myocyte proliferation at the injury site. Then, miR-1 and an inhibitor of miR-133 (e.g., 2'-O-methyl-miR-133) are co-administered to the muscle injury site at a second time point increase differentiation of the proliferated myocytes. The temporally coordinated co-administration of multiple miRNAs and/or miRNA inhibitors can further improve recovery from muscle injury.

In some embodiments, the muscle injury results from a mechanical muscle trauma, a muscular degenerative disorder, a cardiac insult, or a combination thereof. Mechanical muscle trauma can be the result of, for example, blunt force trauma such as occurs in automobile accidents or impaling injuries, wherein the muscle tissue is sliced or torn. Exemplary non-limiting muscular degenerative disorders include muscular dystrophies (e.g., Duchenne muscular dystrophy (DMD)), motor neuron diseases (e.g., amyotrophic lateral sclerosis (ALS)), inflammatory myopathies (e.g., dermatomyositis (DM)), neuromuscular junction diseases (e.g., myasthenia gravis (MG)), endocrine myopathies (e.g., hyperthyroid myopathy (HYPTM)), and metabolic muscular diseases (e.g., phosphorylase deficiency (MPD)). Exemplary non-limiting cardiac insult muscle injuries include myocardial infarction and cardiac muscle reperfusion injury. In some embodiments, the miRNA targeted to a particular gene is selected from the group consisting of miR-1, miR-133, miR-206, miR-208, miR-22, miR-26, miR-29, miR-30, miR-128, miR-143, and miR-145 (SEQ ID NOs: 1-11, respectively), including miRNAs having sequences at least 70%, 80%, 85%, 90%, 91%, 92%, 93%, 94%, 95%, 96%, 97%, 98%, or 99% identical to the sequences set forth in any one of SEQ ID NOs 1-11. In some embodiments, the gene is a myocyte differentiation gene (e.g., encoding HDAC4 or TRAP240) or a myocyte proliferation gene (e.g., encoding SRF).

With respect to the therapeutic methods of the presently disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently disclosed subject matter.

As such, the presently disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economical importance to humans. Thus, also provided is the treatment of livestock, including, but not limited to, domesticated swine, ruminants, ungulates, horses (including race horses), poultry, and the like.

Suitable methods for administering to a subject an miRNA or a vector encoding the miRNA include but are not limited to systemic administration, parenteral administration (including intravascular, intramuscular, intraarterial administration), oral delivery, buccal delivery, subcutaneous administration, inhalation, intratracheal installation, surgical implantation, transdermal delivery, local injection, and hyper-velocity injection/bombardment. Where applicable, continuous infusion can enhance drug accumulation at a target site.

The particular mode of administration used in accordance with the methods of the present subject matter depends on various factors, including but not limited to the miRNA and/or vector carrier employed, the severity of the condition to be treated, and mechanisms for metabolism or removal of the active compound(s) following administration.

The term "effective amount" is used herein to refer to an amount of the therapeutic composition (e.g., a composition comprising an miRNA or a vector encoding the miRNA) sufficient to produce a measurable biological response (e.g., an increase in myocyte differentiation and/or proliferation). Actual dosage levels of active compounds in a therapeutic composition of the presently disclosed subject matter can be varied so as to administer an amount of the active compound(s) that is effective to achieve the desired therapeutic response for a particular subject and/or application. The selected dosage level will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and dose is escalated in the absence of dose-limiting toxicity to a minimally effective amount. Determination and adjustment of an effective dose, as well as evaluation of when and how to make such adjustments, are within the ordinary skill in the art.

EXAMPLES

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

Figure 6:
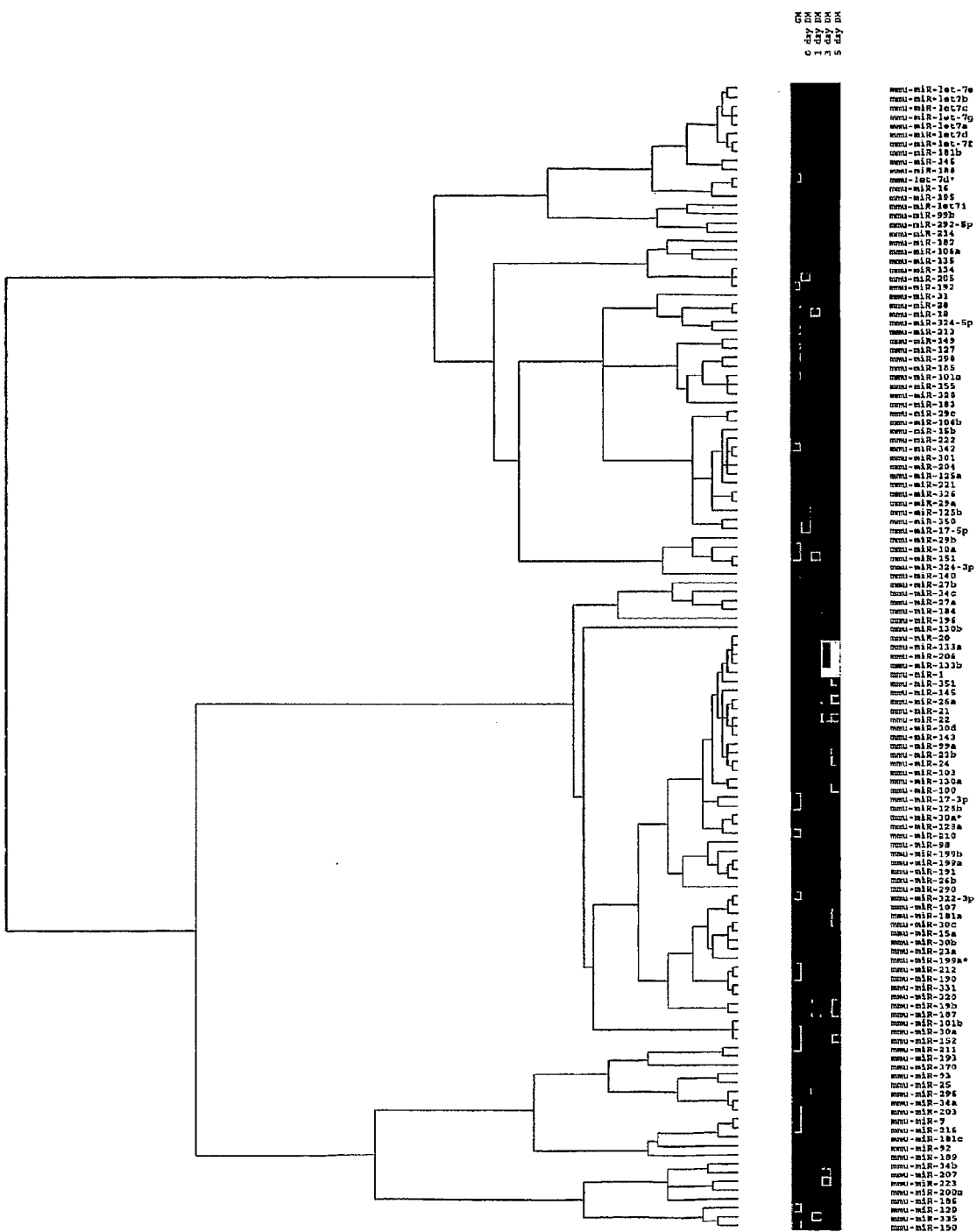
FIG. 6 shows analysis data from miRNA array expression data from C2C12 myoblasts cultured in growth medium (GM) or in differentiation medium (DM) for 0, 1, 3 and 5 days, respectively. Normalized log (base 2) data was hierarchically clustered by gene and is plotted as a heat map. The range of signal was from −4 fold to +4 fold. Light shading denotes high expression and dark shading denotes low expression, relative to the median.
Figure 7:
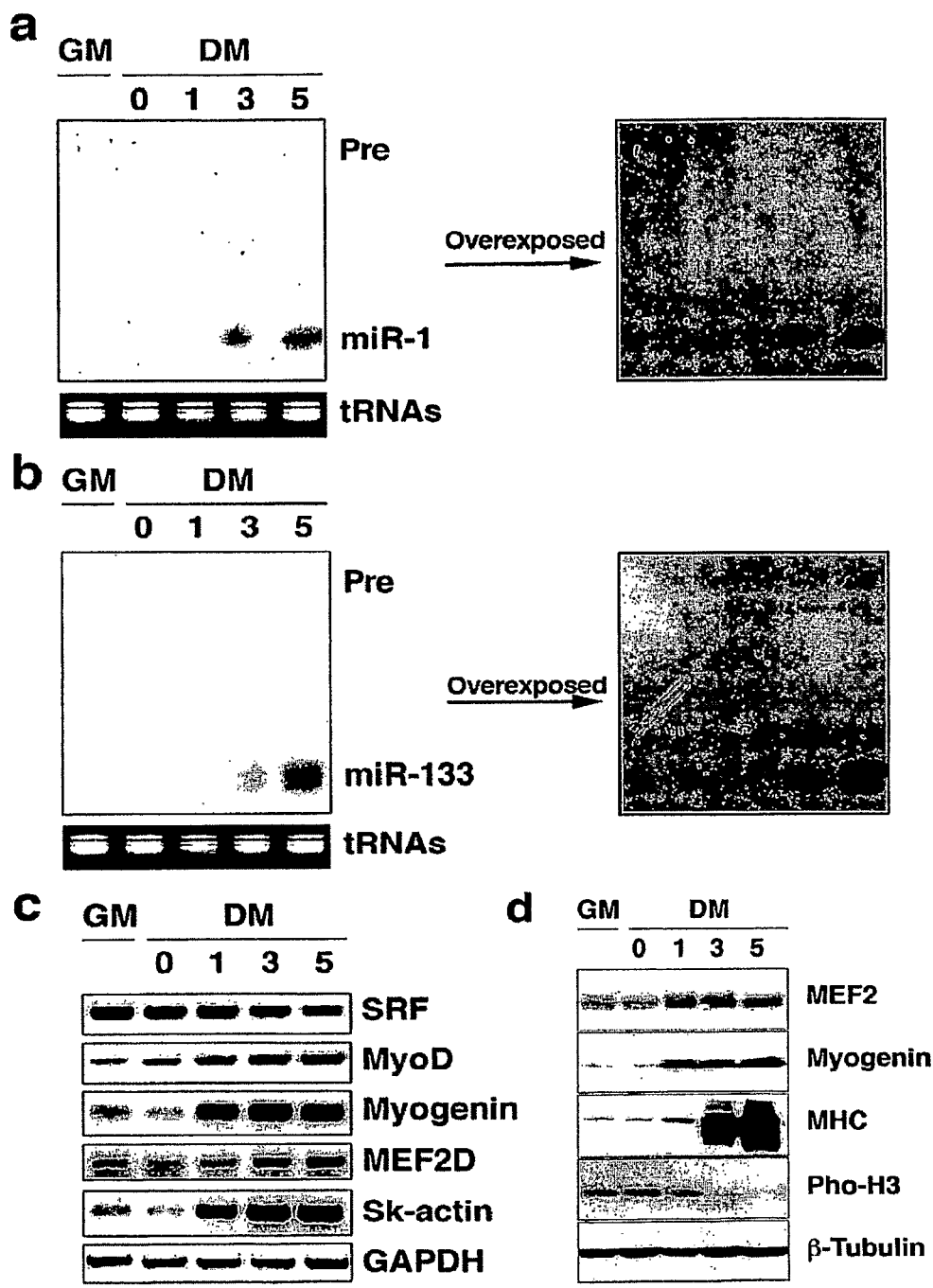
FIGS. 7*a*-7*d* shows data of expression of miR-1, miR-133 and skeletal muscle differentiation marker genes in C2C12 cells.

In order to understand the potential involvement of microRNAs (miRNAs) in skeletal muscle proliferation and differentiation, we analyzed the expression of miRNAs during skeletal muscle differentiation using the established microarray analysis[9]. We chose to use C2C12 myoblasts because this line of cells faithfully mimics skeletal muscle differentiation in vitro as myoblasts can be induced to become terminally differentiated myotubes when serum is withdrawn from the culture medium.[10-12] We found that the expression of a fraction of the miRNAs examined was up-regulated in differentiated C2C12 myoblasts/myotubes (FIG. 1a and FIG. 6). The increase in expression of miR-1 and miR-133 in differentiated myoblasts was confirmed by Northern blot analysis (FIG. 1b and FIG. 7).

Figure 8:
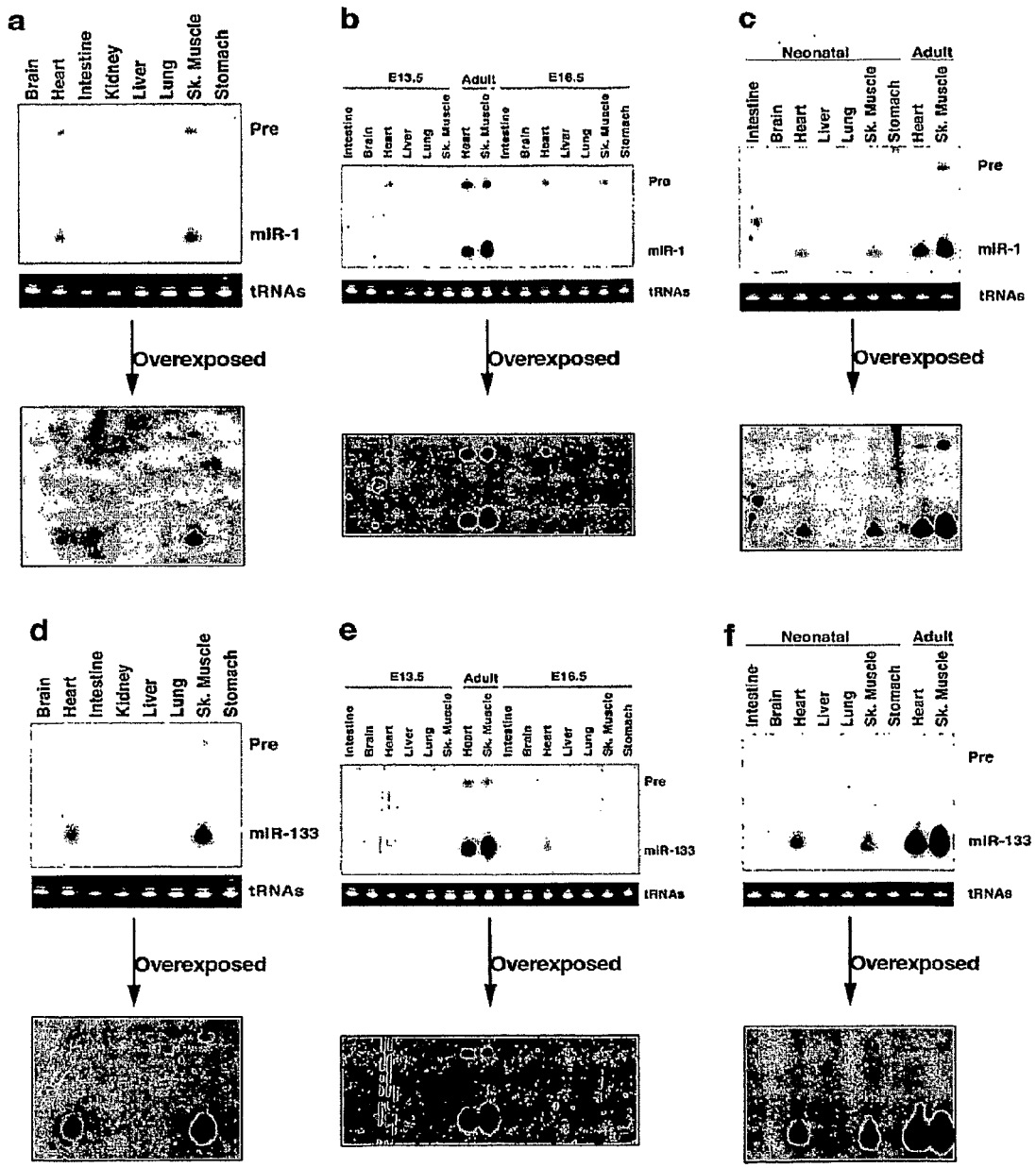
FIGS. 8*a*-8*f* show data of expression of miR-1 and miR-133 in cardiac and skeletal muscle in adult mice and throughout development. Northern blot analysis is shown of the expression of miR-1 (FIG. 8*a*) and miR-133 (FIG. 8*d*) in adult mouse tissues. Northern blot analysis is shown of the expression of miR-1 (FIG. 8*b*) and miR-133 (FIG. 8*e*) in embryonic day 13.5 (E13.5) and 16.5 (E16.5) mouse tissues. The same amount of total RNA from adult heart and skeletal muscle was also loaded in the blot to serve as a comparison. Northern blot analysis is shown of the expression of miR-1 (FIG. 8*c*) and miR-133 (FIG. 8*f*) in neonatal mouse tissues. The same amount of total RNA from adult heart and skeletal muscle was also loaded in the blot to serve as a comparison. Both mature miRNAs and their precursors (Pre) are indicated. tRNAs were used as loading controls.

Example 2 miR-1 and miR-133 are specifically expressed in adult cardiac and skeletal muscle tissues, but not in other tissues tested (FIG. 1c, FIG. 8). However, little is known about the temporospatial distribution of specific miRNAs during mammalian development. We therefore examined the expression of miR-1 and miR-133 in mouse embryos and neonates. miR-1 and miR-133 are expressed at very low levels in the developing hearts and skeletal muscle of E13.5 and E16.5 embryos, (FIG. 1d and FIG. 8). An increasing level of miR-1 and miR-133 expression was found in neonatal hearts and skeletal muscle, though it is still significantly lower than that of adults (FIG. 1e and FIG. 8). These data are consistent with findings from zebrafish in which the majority of miRNAs are expressed relatively late during embryogenesis[16].

Example 3

Figure 9:
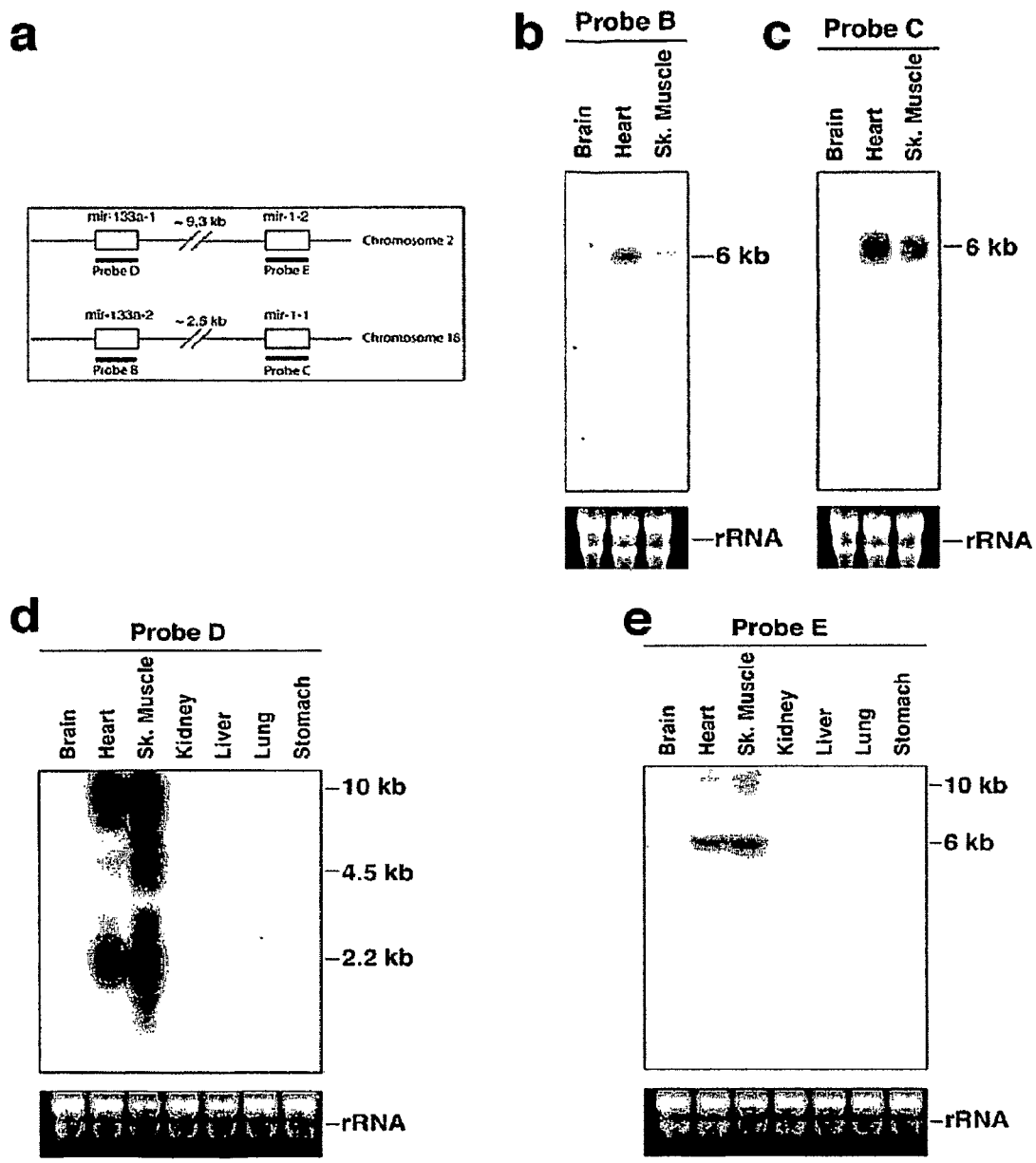
FIGS. 9*a*-9*e* show data for expression of miR-1 and miR-133 primary transcripts in cardiac and skeletal muscle.

Both miR-1 and miR-133 are clustered together on mouse chromosomes 2 (separated by 9.3 kb) and 18 (separated by 2.5 kb) (FIG. 9 and ref. 14). We performed a Northern blot analysis using ~300 by genomic probes including the miR-1 or miR-133 sequences (FIGS. 9a-9e). miR-1 and miR-133 probes from chromosome 18 detected a single primary transcript of ~6 kb from total RNAs isolated from heart and skeletal muscle (FIGS. 9b and 9c), indicating that miR-1 and miR-133 are indeed transcribed together. While both miR-1 and miR-133 probes from chromosome 2 detected a transcript of ~10 kb from the heart and skeletal muscle, the miR-133 probe also hybridized to two additional transcripts of ~4.5 kb and ~2.2 kb, while the miR-1 probe also detected a major transcript of ~6 kb (FIGS. 9d and 9e), suggesting the potential involvement of post-transcriptional processing. Together, our data indicate that cardiac- and skeletal muscle-specific expression of miR-1 and miR-133 is dictated at the primary transcription step.

Example 4

Figure 10:
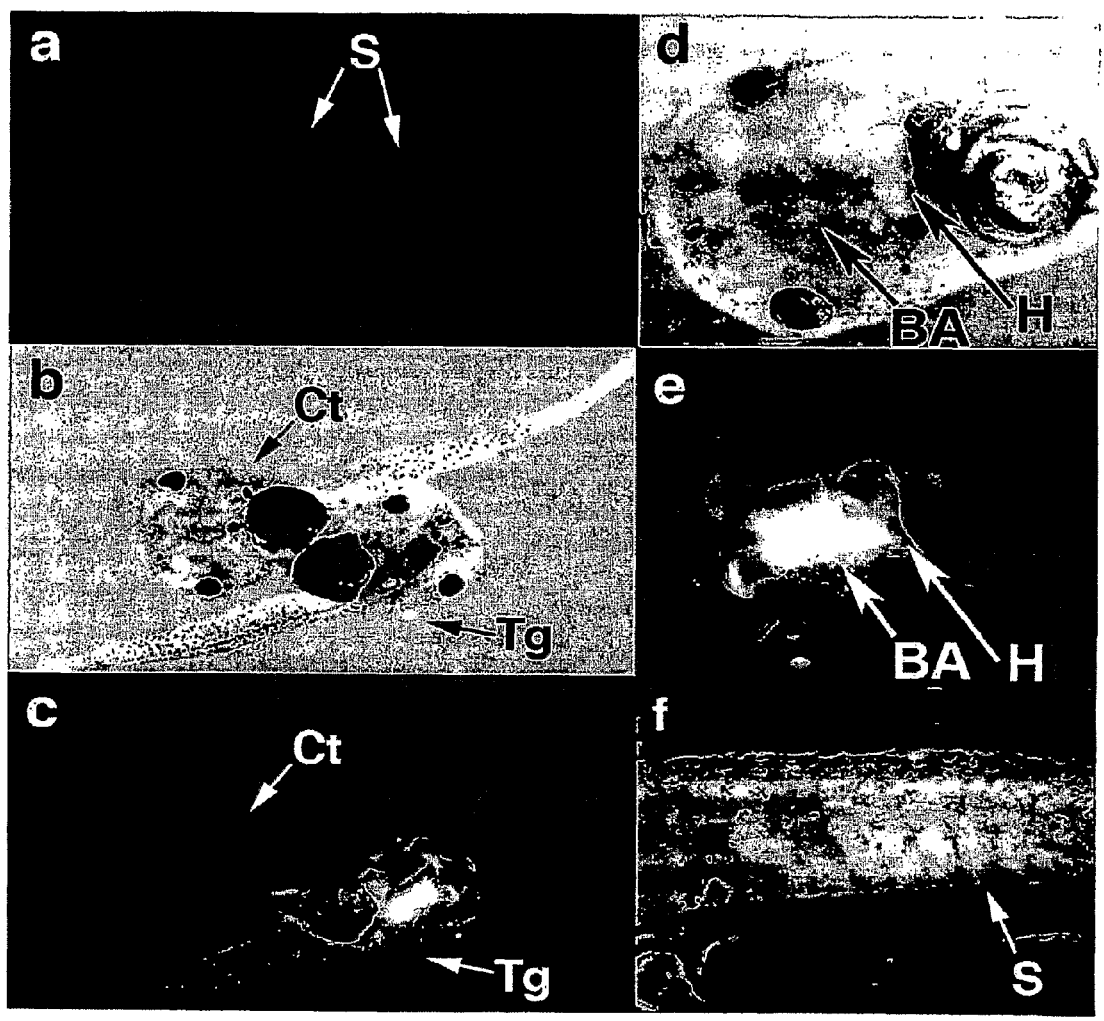
FIGS. 10*a*-10*g* provide data showing miR-1 and miR-133 enhancer can direct reporter gene expression in cardiac and skeletal muscle_

We reasoned that the regulatory elements which control the transcription of both chromosome 2 and 18 miR-1 and miR-133 clusters are likely conserved. We therefore performed sequence analysis and identified a highly conserved region (~2 kb), which lies about 50 kb upstream of the miR-1/133 clusters on both chromosome 2 and 18 (FIG. 10). When this genomic fragment from chromosome 2 was used to drive the expression of a dsRed reporter gene in transgenic Xenopus, we found cardiac- and skeletal-muscle specific expression of the transgene (FIG. 10).

Example 5

Figure 2:
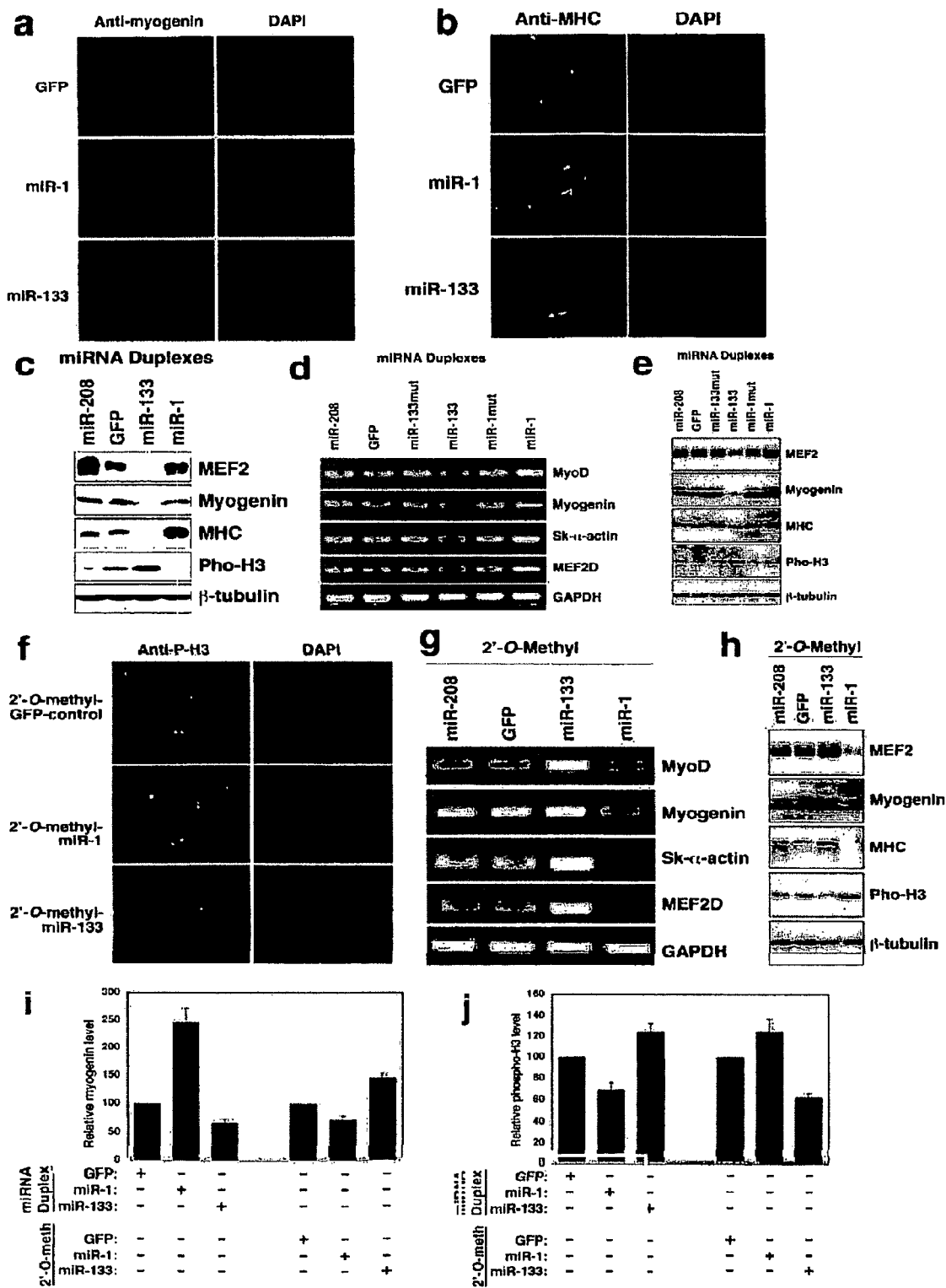
FIGS. 2a-2j depict data showing regulation of myoblast proliferation and differentiation by miR-1 and miR-133. C2C12 myoblasts cultured in growth medium (GM) were electroporated with double-stranded miRNA duplexes for miR-1, miR-133, and GFP as a control.
Figure 11:
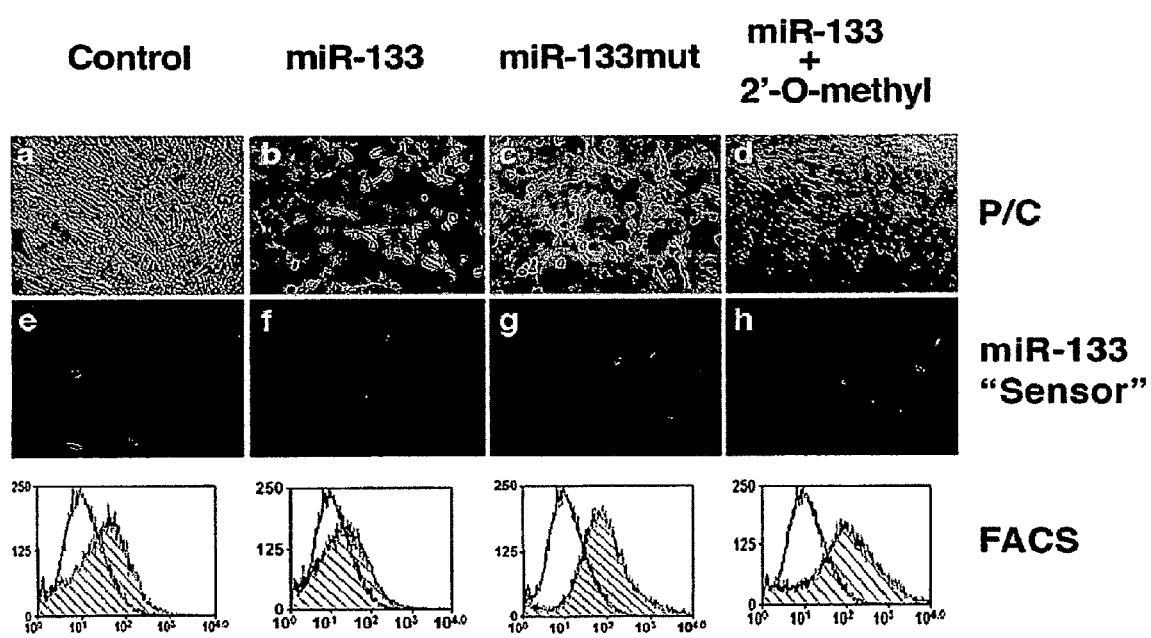
FIGS. 11*a*-11*h* show data demonstrating repression of a miR-133 sensor by miR-133 in C2C12 cells. C2C12 cells stably expressing the miR-133 sensor were transfected with expression vectors for GFP (control), wild-type miR-133 (miR-133), mutant miR-133 (miR-133mut) in which the "seed" sequence has been mutated, or a combination of miR-133 expression vector and 2'-O-methyl antisense oligos (miR-133+2'-O-methyl). Cells were transferred into differentiation medium for 12 hr and images were obtained using phasecontrast (P/C) (FIGS. 11*a*-11*d*) or fluorescence to show expression of the dsRed reporter gene (FIGS. 11*e*-11*h*). Cells from each condition were harvested and the expression of the dsRed reporter gene was quantified using FACS analysis (lower panels). Open area under the line denotes autofluorescein of the cell and striped area under the line indicates the ds-Red expression.

To assess the function of miR-1 and miR-133 in skeletal muscle, we first attempted to overexpress miR-1 and miR-133 in mammalian cells. We tested and validated the expression and activity of both miRNAs using Northern blot analysis as well as miR-1 and miR-133 "sensors"[17], in which the complementary sequences for miR-1 or miR-133 were cloned downstream of a dsRed coding sequence (FIG. 11 and data not shown). We transfected C2C12 myoblasts with miR-1 or miR-133 and then either maintained cells in growth medium (GM) or transferred them to differentiation medium (DM) after transfection. miR-1 strongly enhanced myogenesis as indicated by increased expression of both the early and late myogenic markers myogenin and myosin heavy chain (MHC), respectively, as well as other myogenic markers, including MyoD, Mef2, and skeletal α-actin (FIGS. 2a-2e, 2i, 2j and Table 2). miR-1 induced myogenic marker gene expression in cells maintained in both the log-phase growth condition (FIG. 2c) and the differentiation condition (FIGS. 2, 2d, 2e). Accelerated myogenic differentiation induced by miR-1 is also accompanied by a decrease in cell proliferation, as marked by a significant decrease in the expression of phospho-histone H3 (FIGS. 2, 2c, 2e and Table 2). Of particular note, miR-1 induced myogenesis is specific, since overexpression of a GFP control or miR-208, which is not endogenously expressed in skeletal myocytes, showed no effect (FIGS. 2a-2e). Furthermore, mutations introduced into miR-1 "seed" sequences abolished its ability to activate myogenic gene expression (FIGS. 2d-2e). In contrast, overexpression of miR-133 repressed the expression of myogenin and MHC (FIG. 2, a-e and Table 2) and promoted myoblast proliferation (FIGS. 2c-2e and Table 2). Again, the effect of miR-133 on myoblasts proliferation is specific, as controls showed no effect and mutation introduced abolished the function of miR-133 (FIGS. 2a-2e, 2j).

(FIGS. 3e, 3f, 3j). Cardiac tissue is completely absent as judged by histology, tropomyosin staining (FIGS. 3f, 3j) and cardiac actin staining. In addition to these defects, there is a dramatic decrease in phospho-histone H3 staining (FIGS. 3i-3k), consistent with the essential role of miR-1 in regulating myocyte proliferation and differentiation. Although misexpression of miR-133 also leads to a reduction in anterior structures and detects in somite development, in contrast to miR-1, there is only a modest reduction in anterior-posterior length and somatic defects are most severe in the more anterior or posterior aspects of the embryo where somites fail to form (FIGS. 3g, 3h). In addition, cardiac tissue frequently forms in miR-133 embryos, though it is highly disorganized and fails to undergo cardiac looping or chamber formation

TABLE 2

Effect on myogenic proliferation and differentiation by miR-1 and miR-133 overexpress and knock down

| | DM (8 hr) | | DM (12 hr) | | | | DM (24 hr) | | | | | |
|---|---|---|---|---|---|---|---|---|---|---|---|---|
| Treatment | Myogenin positive cells | Relative to control | Myogenin positive cells | Relative to control | Phospho-H3 positive cells | Relative to control | Myogenin positive cells | Relative to control | Phospho-H3 positive cells | Relative to control | MHC positive cells | Relative to control |
| GFP | 172 | 100% | 93 | 100% | 135 | 100% | 118 | 100% | 137 | 100% | 22 | 100% |
| miR-1 | 206 | 121% | 230 | 247.3% | 93 | 68.9% | 251 | 212.7% | 76 | 55.5% | 56 | 254.5% |
| miR-133 | 89 | 51.7% | 68 | 73.1% | 168 | 124.4% | 93 | 78.8% | 201 | 146.7% | 12 | 54.5% |
| 2'-O-methyl-GFP | 146 | 100% | 145 | 100% | 172 | 100% | 348 | 100% | 207 | 100% | 22 | 100% |
| 2'-O-methyl-miR-1 | 120 | 82.2% | 98 | 67.6% | 214 | 124.4% | 299 | 85.9% | 283 | 136.7% | 18 | 81.8% |
| 2'-O-methyl-miR-133 | 205 | 140.4% | 211 | 145.5% | 107 | 62.2% | 498 | 143.1% | 191 | 92.3% | 44 | 200% |

We performed the reciprocal experiment wherein we transfected C2C12 myoblasts with the miR-1 or miR-133 2'-O-methyl antisense inhibitory oligos (or control GFP and miR-208), which have been shown to inhibit the function of miRNAs[18,19]. Cells transfected with the miR-1 inhibitor showed inhibition of myogenesis and promotion of myoblast proliferation, as indicated by a decrease in myogenic markers and an increase in phospho-histone H3 (FIGS. 2f-2i and Table 2). Consistent with the role of miR-133 in promoting myoblast proliferation and repressing differentiation, inhibition of miR-133 caused an opposing effect, where myogenesis was enhanced and cell proliferation repressed (FIGS. 2f-2j and Table 2). In contrast, control 2'-O-methyl inhibitors showed no effects (FIGS. 2f-2j). We conclude that miR-1 and miR-133 have distinct roles in skeletal muscle proliferation and differentiation: miR-1 promotes myoblast differentiation, whereas miR-133 stimulates myoblast proliferation.

Example 6

Figure 3:
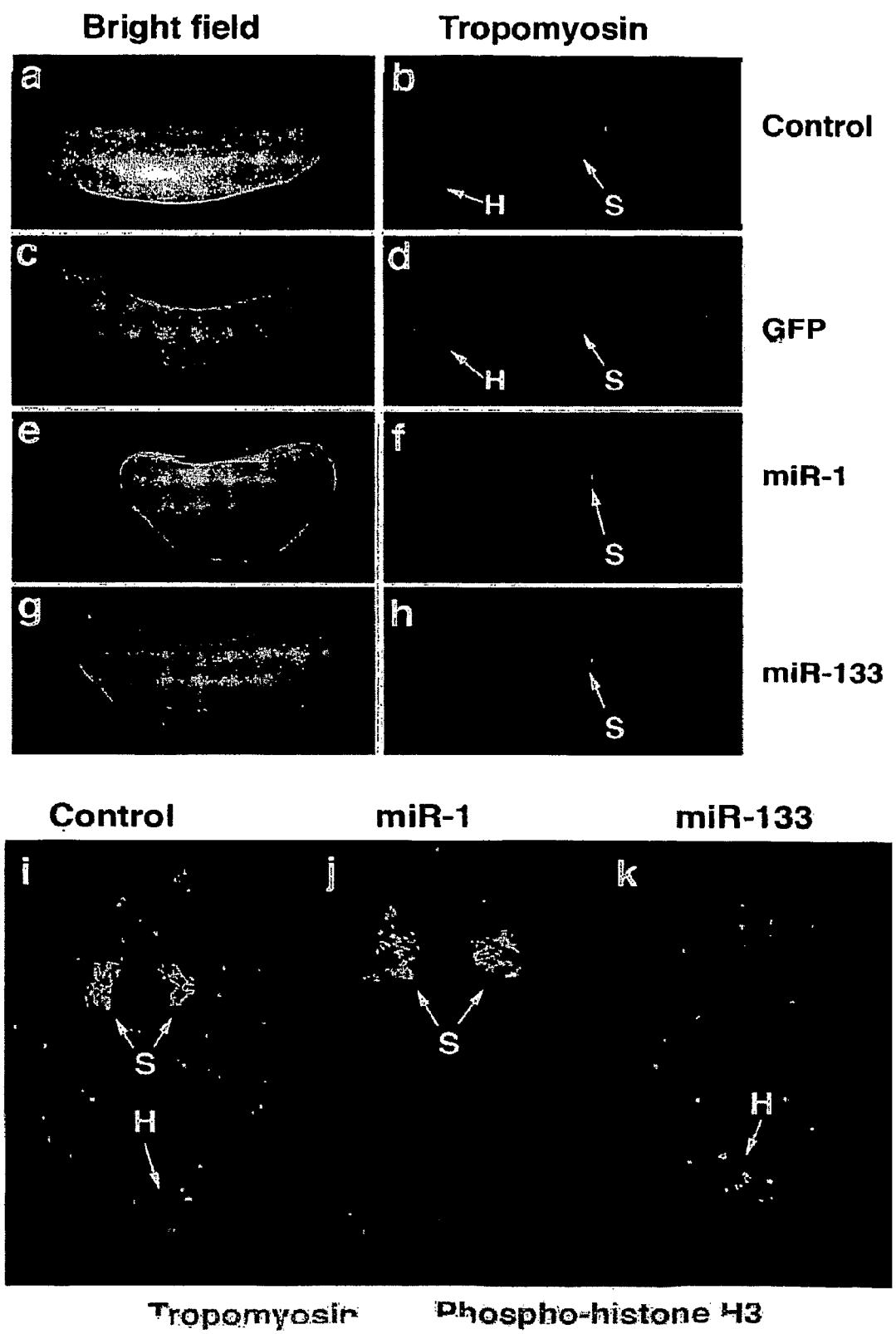
FIGS. 3a-3k depict data showing control of cardiac and skeletal muscle development by miR-1 and miR-133 in vivo.

Both miR-1 and miR-133 have been found in most animal species, from *Drosophila* to human, suggesting they are evolutionary conserved. To test the effects of miR-1 and miR-133 on skeletal muscle and heart development in vivo, we identified copies of miR-1 and miR-133 in *Xenopus* and tested their function through mis-expression. Introduction of miR-1 at the one cell stage leads to a dramatically shortened axis with accompanying reduction in anterior structures and an increase in body size along the dorsal-ventral axis compared to either uninjected or miGFP injected controls (n>45, two independent experiments) (FIG. 3). Although somites formed in miR-1 injected embryos (FIG. 3), whole-mount antibody staining and serial sectioning reveal the tissue is highly disorganized and fails to develop into segmented structures (FIGS. 3g, 3h, 3k). Collectively, these data suggest that the correct timing and levels of both miR-1 and miR-133 are necessary for proper skeletal muscle and heart development.

Example 7

HDAC4 contains two naturally occurring putative miR-1 sites at its 3' UTR, which are evolutionarily conserved among vertebrate species (FIG. 12). Similarly, two conserved miR-133 binding sites are found in the 3' UTR of the mammalian SRF gene (FIG. 12), which has been shown to play an important role in muscle proliferation and differentiation in vitro and in vivo[11,24,25].

Figure 4:
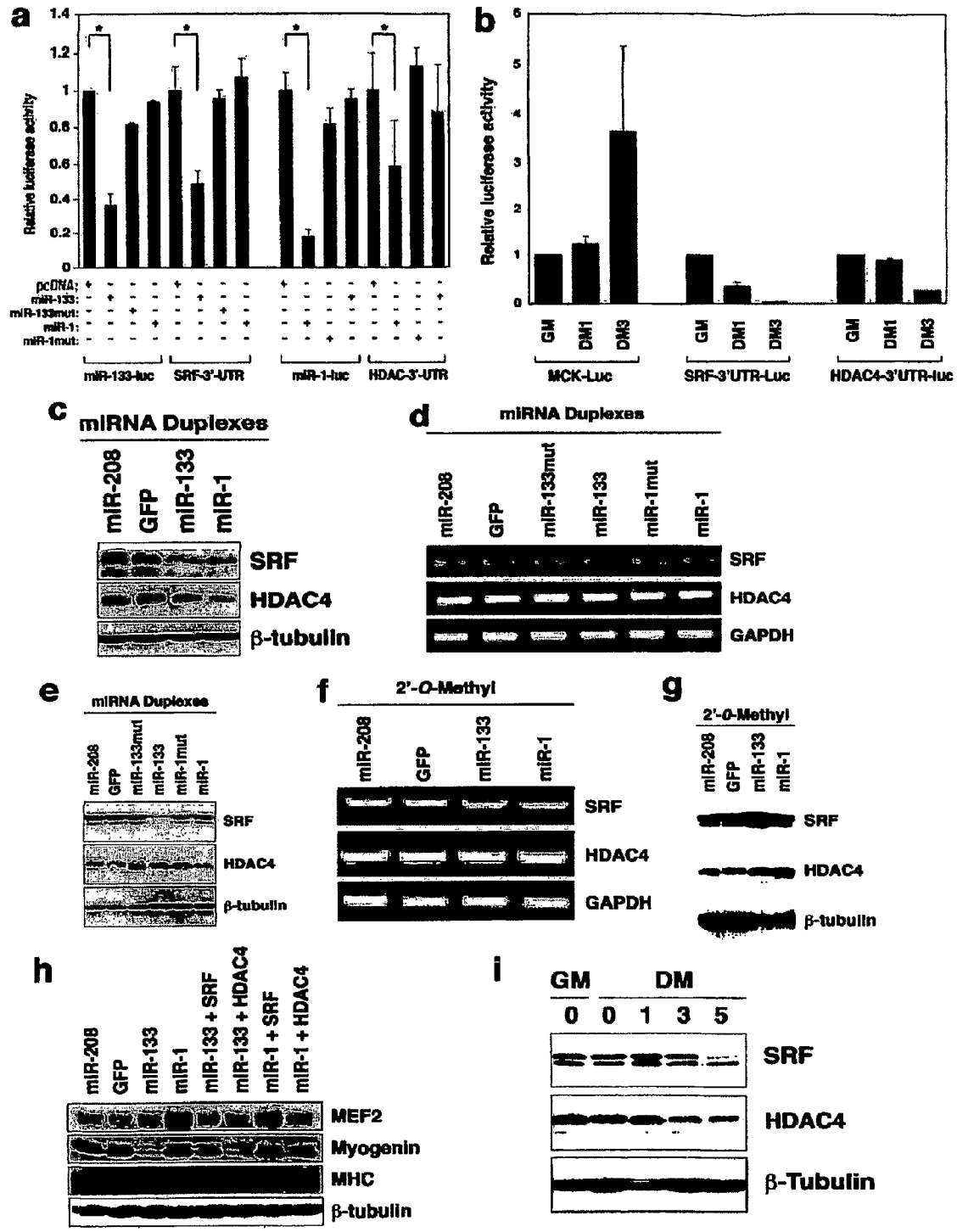
FIGS. 4a-4i depict data showing identification of miR-1 and miR-133 target genes in skeletal muscle.

We fused the 3' UTRs of mouse SRF and HDAC4 to a luciferase reporter gene and transfected these constructs along with transfection controls into mammalian cells. Ectopic overexpression of miR-1 strongly repressed a HDAC4 3' UTR luciferase reporter gene, whereas miR-133 inhibited the expression of a SRF 3' UTR luciferase reporter gene (FIG. 4a). In contrast, mutations introduced into miR-1 or miR-133 "seed" sequences abolished such repression, indicating the specificity of the action (FIG. 4a).

When the above reporters were transfected into C2C12 myoblasts and luciferase activity measured before and after the induction of cell differentiation, we found that the reporter activity was dramatically repressed in differentiated cells (FIG. 4b), indicating that increased levels of endogenous miR-1 and miR-133 inhibited the reporter gene. The effects and specificity of endogenous miR-1 and miR-133 were monitored by the miRNA'"sensor" (FIG. 11). In contrast, the luciferase activity of the MCK-luc reporter, an indicator of muscle differentiation, was increased in differentiated myocytes (FIG. 4b). Furthermore, overexpression of miR-1 led to the down-regulation of endogenous HDAC4 protein in C2C12 cells in both the growth condition (FIG. 4c) and differentiation condition (FIG. 4e), whereas miR-133 repressed the expression of endogenous SRF proteins (FIGS. 4c, 4e). In contrast, the mRNA levels of SRF and HDAC4 were not altered by those miRNAs (FIG. 4d), supporting the notion that miRNAs repress the function of their target genes mainly by inhibiting translation. When 2'-O-methyl-antisense oligos against miR-1 or miR-133 were applied, they relieved repression exerted on the protein levels of HDAC4 or SRF, respectively (FIG. 4g), with no effect on their mRNA levels (FIG. 4f).

To further verify that HDAC4 and SRF are cognate targets for miR-1 or miR-133 in regulating skeletal muscle gene expression, we tested whether cotransfecting expression plasmids for SRF or HDAC4 could "suppress" miRNA-mediated myogenesis. Indeed, as shown in FIG. 4h, overexpression of SRF partially reversed myogenic gene repression induced by miR-133. In contrast, HDAC4 counteracted the effects of miR-1 on skeletal muscle gene expression (FIG. 4h).

Consistent with the potential involvement of HDAC4 and SRF in miR-1 and mir-133-dependent skeletal muscle proliferation and differentiation, endogenous HDAC4 and SRF protein levels were down-regulated in differentiated C2C12 cells, with a concomitant increase in expression of myogenic differentiation markers and a decrease in expression of the mitotic index marker phospho-histone H3 (FIG. 4i and FIG. 7d). Decreased expression of SRF and HDAC4 proteins was accompanied by an increase expression of miR-1 and miR-133 (compare FIG. 4i with FIG. 1b). Together, these data demonstrate that miR-1 and miR-133 specifically repress HDAC4 and SRF protein levels, respectively, which in turn, contributes to (at least in part) the regulatory effects of those miRNAs on myoblast proliferation and differentiation.

Figure 5:
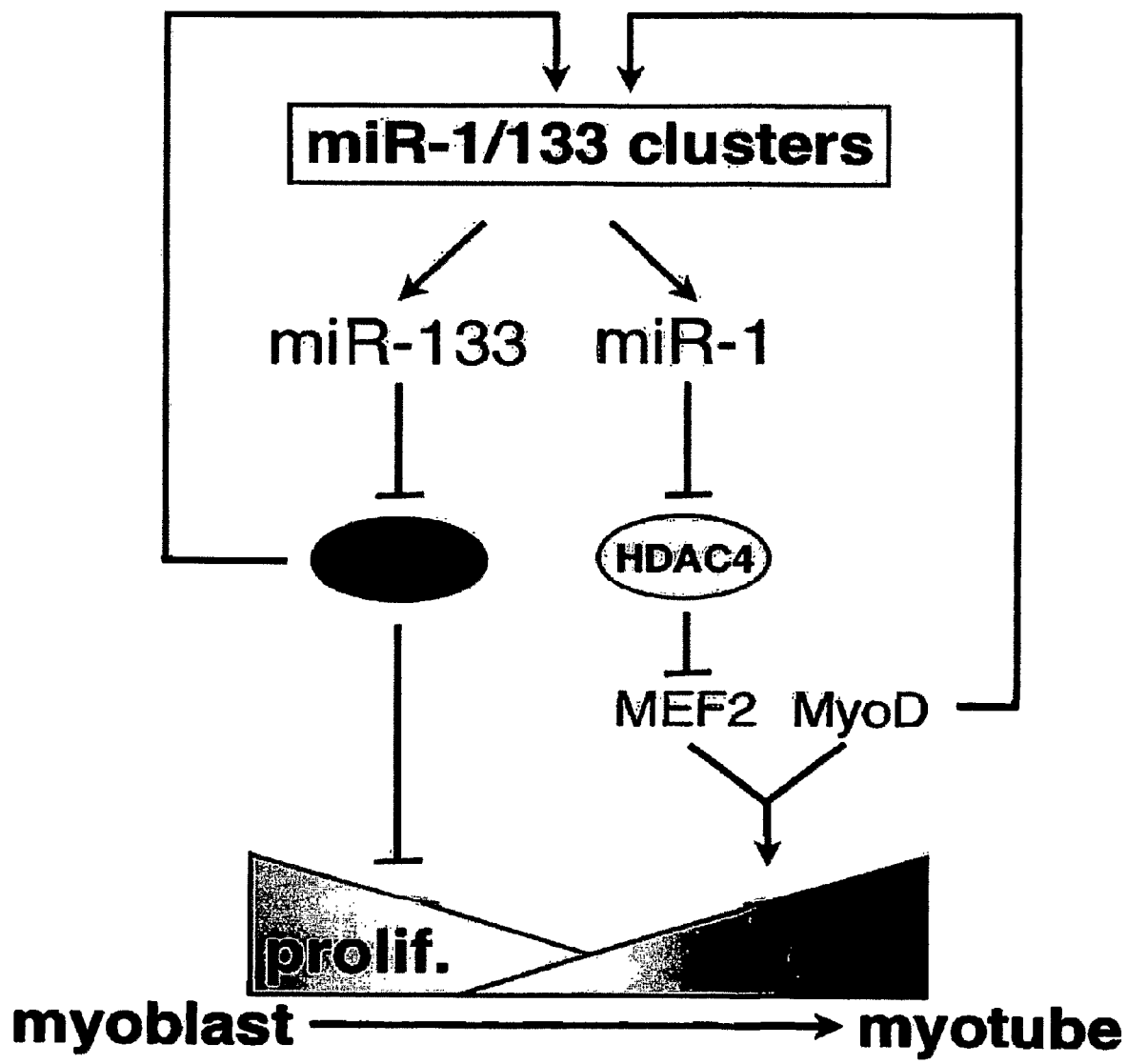
FIG. 5 shows a model for miR-1 and miR-133-mediated regulation of skeletal muscle proliferation and differentiation.

We characterized cardiac- and skeletal muscle-specific miR-1 and miR-133 and have shown their function in controlling skeletal muscle proliferation and differentiation. Of significance, we found that miR-1 and miR-133, which are clustered on the same chromosomal loci and transcribed together as a single transcript, become two independent, mature miRNAs with distinct biological functions achieved by inhibiting different target genes. This implicates the involvement of miRNAs in complex molecular mechanisms. Interestingly, while the tissue-specific expression of miR-1 and miR-133 is controlled by myoD and SRF[8], SRF expression is repressed by miR-133. Therefore, these findings reveal a negative regulatory loop in which miRNAs participate in regulatory pathways to control cellular proliferation and differentiation (FIG. 5).

Materials and Methods for Examples 1-7

MicroRNA Expression Analysis by Microarray

Total RNA was isolated from C2C12 cells cultured in growth medium (GM) consisting of Dulbecco's Modified Eagle Medium (DMEM) (Sigma Chemical Co., St. Louis, Mo., U.S.A.) with 10% fetal bovine serum (FBS) (Sigma) and 1% penicillin/streptomycin (Invitrogen, Carlsbad, Calif., U.S.A.) or differentiation medium (DM) consisting of DMEM (Sigma) with 2% horse serum (Sigma) at different time points (day 0, 1, 3, and 5 with the first day transferring into DM counted as day 0). Microarray hybridization was performed and data analyzed as described[9]. Briefly, 2.5 ug isolated RNA was labeled with 5'-phosphate-cytidyl-uridyl-Cy3-3' (Dharmacon, Inc., Lafayette, Colo., U.S.A.) using RNA ligase and hybridized with 0.5 mM mixture of oligonucleotide probes for 124 microRNAs labeled with ALEXA 647® (Cy5) (Molecular Probes, Eugene, Oreg., U.S.A.) in disposable chambers (MJ Research, Reno, Nev., U.S.A.; part number SLF-0601). Normalized log (base 2) data was hierarchically clustered by gene and is plotted as a heat map. The range of signal was from −4 fold to +4 fold. Yellow denotes high expression and blue denotes low expression, relative to the median.

Northern Blot Analysis

Total RNA was extracted from C2C12 cells, mouse embryonic or adult tissue using TRIZOL® Reagent (Invitrogen). For Northern blot analysis of miRNA, PEG was applied to remove large sized RNAs. Briefly, 30 µg of each total RNA sample were mixed 1:1 with 5x PEG solution and placed on ice 10 min. After 10 min centrifuging at maximum speed at 4° C., the supernatant was transferred to a fresh tube. RNAs were then precipitated by adding 2.5 volumes of 100% EtOH and centrifuged 30 min at maximum speed. Northern blot analysis for miRNAs was performed as described[13]. miR-1 and miR-133 oligonucleotide sequences used as probes are listed in Table 3. Northern blot analysis was used to detect primary transcripts of miRNAs and performed as described[26], using 20 µg of total RNA from each sample. Genomic fragments for miR-1 and miR-133 were PCR-cloned and serve as probes.

TABLE 3

Sequences of Oligonucleotides Disclosed Herein

| Name | Sequence |
| --- | --- |
| miR-1 probe | TACATACTICTTTACATTCCA |
| miR-133 probe | ACAGCTGGTTGAAGGGGACCAA |
| miR-133a-1-up | CATGTGACCCCTCACACACA |
| miR-133a-1-down | ACAAGGGGAGCCTGGATCCC |
| miR-133a-2-up | GGACATATGCCTAAACACGTGA |
| miR-133a-2-down | GAAACATCTTTATCCAGTTT |
| miR-1-2-up | AGACTGAGACACAGGCGACACC |
| miR-1-2-down | TGCCGGTCCATCGGTCCATTGC |
| miR-1-1-up | CACTGGATCCATTACTCTTC |
| miR-1-1-down | TTGGAATGGGGCTGTTAGTA |

TABLE 3-continued

Sequences of Oligonucleotides Disclosed Herein

| Name | Sequence |
|---|---|
| miR-1mut-up | TGAACATTCAGTGCTATAAAGAAGTATGTATTTTGGGTAGGTA |
| miR-1mut-down | TACCTACCCAAAATACATACTTCTTTATAGCACTGAATGTTCA |
| miR-133mut-up | AATCGCCTCTTCAATGGATTTGTCAACCAGCTGTAGCTATGCATTGAT |
| miR-133mut-down | ATCAATGCATAGCTACAGCTGGTTGACAAATCCATTGAAGAGGCGATT |
| miR-1 duplex | UGGAAUGUAAAGAAGUAUGUA |
| | CAUACUUCUUUACAUUCCAUA |
| miR-1-mut duplex | UUAACCAUAAAGAAGUAUGUA |
| | CAUACUUCUUUAUGGUUAAUA |
| miR-133 duplex | UUGGUCCCCUUCAACCAGCUGU |
| | AGCUGGUUGAAGGGGACCAAAU |
| miR-133-mut duplex | UCAAGUAACUUCAACCAGCUGU |
| | AGCUGGUUGAAGUUACUUGAAU |
| miR-208 duplex | AUAAGACGAGCAAAAAGCUUGU |
| | AAGCUUUUUGCUCGUCUUAUAC |
| GFP duplex | AACUUCAGGGUCAGCUUGCCUU |
| | GGCAAGCUGACCCUGAAGUUGG |
| 2'-O-methyl-miR-1 | AAAUACAUACUUCUUUACAUUCCAUAGC |
| 2'-O-methyl-miR-133 | AGCUACAGCUGGUUGAAGGGGACCAAAUCCA |
| 2'-O-methyl-miR-208 | GACCAACAAGCUUUUUGCUCGUCUUAUACGUG |
| 2'-O-methyl-GFP | AAGGCAAGCUGACCCUGAAGUU |
| HDAC4-UTR-up | CAGCACTGGTGATAGACTTGG |
| HDAC4-UTR-down | CTTAAGAATAAGTTCAATAAGAC |
| SRF-UTR-up | AGATATGGGGGCTTGTGCCC |
| SRF-UTR-down | CTGGGAGAAAGGGGGTAGAC |
| Myogenin F | TGGAGCTGTATGAGACATCCC |
| Myogenin R | TGGACAATGCTCAGGGGTCCC |
| MyoD F | GCAGGCTCTGCTGCGCGACC |
| MyoD R | TGCAGTCGATCTCTCAAAGCACC |
| Skeletal α-actin F | CAGAGCAAGCGAGGTATCC |
| Skeletal α-actin R | GTCCCCAGAATCCAACACG |
| MEF2D F | CAAGCTGTTCCAGTATGCCAG |
| MEF2D R | AAGGGATGATGTCACCAGGG |
| HDAC4 F | GAGAGAATTCTGCTAGCAATGAGCTCCCAA |

Cloning and Expression of miR-1 and miR-133

Genomic fragments for miR-1 and miR-133 precursors from mouse chromosomes 2 and 18 (ch 2 and ch 18) were PCR amplified using mouse genomic DNA as a template (for PCR primers, see Table 3 above). The PCR products were cloned into the pcDNA™ (+)3.1 vector (Invitrogen) and the expression of miRNAs was determined by transfecting expression vectors into mammalian cells (COS7, 10T1/2 or C2C12) and detected by Northern blot analysis.

Cell Culture, in Vitro Myogenesis Differentiation and Luciferase Reporter Assay

C2C12 myoblast cells were cultured and myogenesis induced as described[12]. Transient transfection luciferase reporter assays were performed as described[12,26]. miRNA duplexes and 2'-O-methyl antisense oligoribonucleotides for miR-1, miR-133, miR-208 and GFP were purchased from Dharmacon (see Table 3 for sequences). They were introduced into mammalian cells using either LIPOFECTAMINE™ (Invitrogen) transfection (200 nM) or electroporation using the Amaxa Biosystems (Gaithersburg, Md., U.S.A.) NUCLEOFECTOR® system (5 µg).

For 3' UTR-luciferase reporter construction, the multiple cloning site of the pGL3-Control Vector (Promega, Madison, Wis., U.S.A.) was removed and placed downstream of the luciferase gene. 3' UTRs for mouse HDAC4 and SRF were PCR amplified and cloned into the modified pGL3-Control Vector to result in the constructs SRF-3'UTR and HDAC4-3'UTR (see Table 3 for PCR primer sequences). Luciferase reporter assays were performed as describe[26].

Western Blot and Immunostaining

Western blots were performed as described previously[27]. The following antibodies were used: anti-myogenin; SRF; MEF2; HDAC4; and β-tubulin (Santa Cruz Biotechnology, Santa Cruz, Calif., U.S.A.); and phospho-histone H3 (Upstate Biotechnology, Lake Placid, N.Y., U.S.A.). The MF20 antibody, which recognizes striated muscle-specific MHC, was obtained from the DSHB (University of Iowa, Iowa City, Iowa, U.S.A.).

For immunostaining, treated C2C12 cell in 12-well plates were fixed with 4% formaldehyde for 5 min at 37° C. and changed to 0.1% NP40/PBS solution for 15 min at RT. Primary antibodies were incubated in 0.1% NP40-PBS with 3% BSA for 2 hr in the following concentration: anti-myogenin (1:20 dilution), anti-phospho-histone H3 (1:100 dilution), MF20 (1:10 dilution). Secondary antibodies fluorescein anti-mouse/rabbit (1:100 dilution; Vector Laboratories, Burlingame, Calif., U.S.A.) were adding in 0.1% NP40-PBS with 3% BSA for 1 hr at 37° C. DAPI was added in for 5 min at RT. After several wash with PBS, cells were subjected to fluorescence microscopy observation. Ten fields that cover the whole well were picked and green fluorescence positive cells and total cells with DAPI staining were counted for each well, respectively.

RT-PCR Analysis

RT-PCR was performed essentially as described[27]. Total RNA were extracted from C2C12 cells using TRIZOL® reagent (Invitrogen), and 2.0 µg aliquots were reverse transcribed to cDNA using random hexamers and MMLV reverse transcriptase (Invitrogen). For each case, 2.5% cDNA pool was used for amplification and PCR were performed for 24-28 cycles. Sequences for PCR primers can be found in Table 3.

Xenopus Embryo Injections and Transgenesis

Standard methods were utilized in obtaining and culturing Xenopus laevis embryos. DNA constructs were linearized with Kpn I and transgenic embryos were generated according to the methods described by Kroll & Amaya[28]. Expression of the transgene was analyzed under a Leica MZFLIII microscope. Preparation and injection of Xenopus with miRNAs was carried out essentially as previously described[29]. However, RNA was not capped prior to injection. Whole-mount immunohistology analysis was carried out as described[30].

Figure 14:
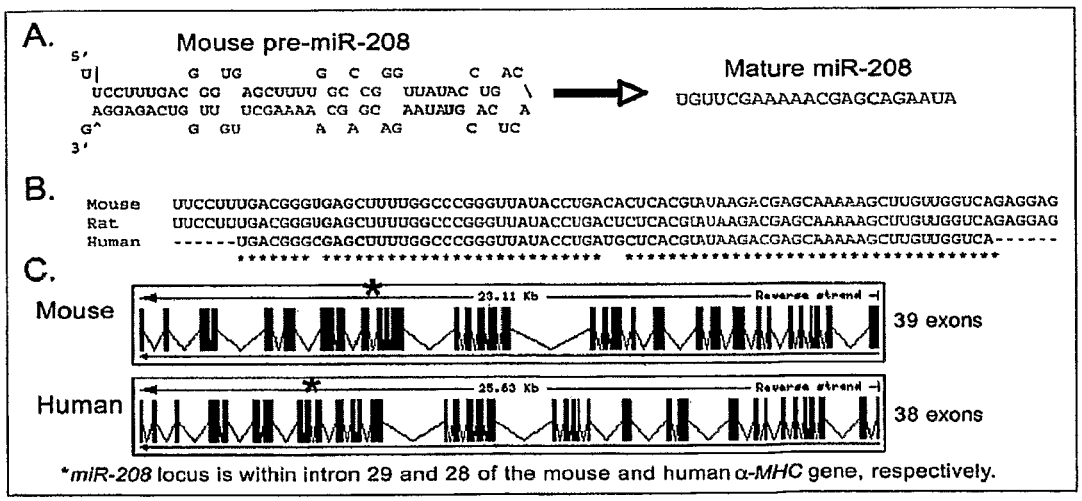
FIGS. 14*a*-14*c* depict miR-208 genomics.
Figure 15:
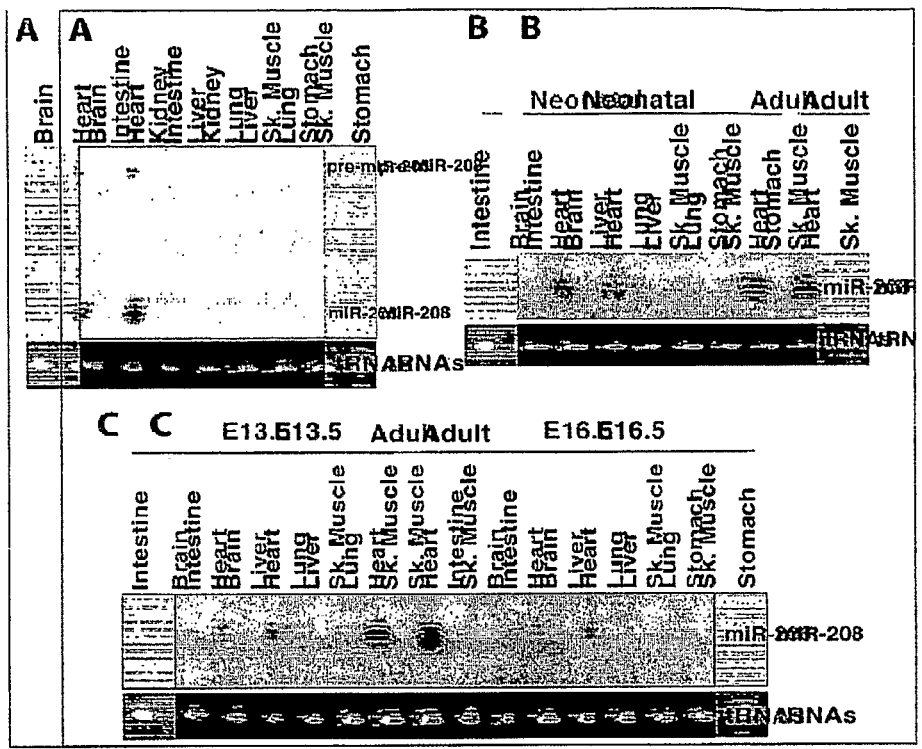
FIGS. 15a-15c show data demonstrating miR-208 is developmentally regulated. Total RNA from different mouse tissues was blotted and probed with a 5'-radiolabeled oligodeoxynucleotide complementary to miR-208. Equal loading of total RNA on the gel was verified by ethidium bromide staining prior to transfer.

Example 8 miR-208 is a cardiac-specific miRNA conserved between human, mouse, and rat (FIG. 14). Northern blot analysis revealed that miR-208 expression is developmentally regulated (FIG. 15). Northern blots were prepared from staged mouse tissues and probed with radiolabeled probe complementary to miR-208. miR-208 levels were dramatically higher in the adult mouse heart relative to E13.5, E16.5, and neonatal stage hearts. miR-208 is hosted by an intron of the cardiac muscle α-myosin heavy chain (α-MHC) gene (FIG. 14). One of two cardiac myosin heavy isoforms, α-MHC is weakly expressed during mouse development but later becomes the predominant isoform in the adult mouse heart. miR-208 and α-MHC are both cardiac-specific and transcribed from the reverse strand, which suggests that miR-208 is processed from the α-MHC intron and is expressed parallel to α-MHC transcription.

Example 9

To investigate the in vitro function of miR-208 in cardiomyocytes, we have chosen to use neonatal rat cardiomyocytes because it is a well-characterized in vitro model for studying the morphological, biochemical, and electrophysiological characteristics of cardiac cells. Neonatal cardiomyocytes do not lose their ability to replicate after birth; a large fraction undergoes mitotic division and proliferates in vitro and in vivo where cardiac gene expression is also activated. It is likely that miR-208 promotes cardiomyocyte differentiation since it is expressed highly in the adult heart relative to earlier development. In order to determine miR-208 function in the heart, this model system is used to study the effects of miR-208 expression and inhibition upon the cardiogenesis program.

In Vitro Model System

Cultured cardiomyocytes are one of the most widely used experimental models in cardiac research. The preparation of cardiomyocytes from small mammals is economical relative to whole animal studies, reliable, and allows for a broad spectrum of experiments. For both economical and technical reasons, cardiomyocytes are most commonly isolated from neonatal rats. We isolate rat cardiomyocytes essentially as previously described, with minor modifications[86].

Figure 16:
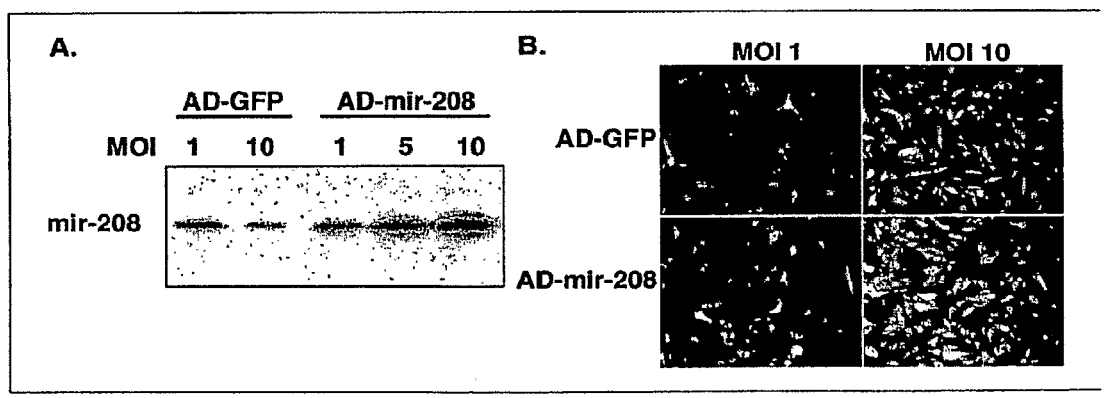
FIGS. 16a and 16b show data of ectopic miR-208 expression in cardiomyocytes.

Functional, mature miRNAs can be ectopically expressed using a RNA Pol II promoter sequence to direct transcription of the miRNA precursor sequence plus ~150 flanking nucleotides. The resulting RNA transcripts are recognized by the miRNA processing machinery and become fully functional miRNAs capable of directing translational repression. We have PCR amplified the miR-208 precursor sequence and flanking regions from mouse genomic DNA and inserted this fragment into an adenovirus vector to generate recombinant adenovirus that expresses miR-208 (Ad-208). Northern blot analysis shows a dosage-dependent increase of mir-208 expression in isolated cardiomyocytes infected with increasing concentrations Ad-208 (FIG. 16). This tool can be utilized to study the effects of miR-208 overexpression on the cardiomyocyte phenotype in vitro.

Analysis of Ectopic miR-208 Expression

A cell counting assay is used to determine if changes in miR-208 expression affects proliferation. Cardiomyocytes are plated at low density and infected with Ad-208. Although adenovirus has been used extensively with great success in cardiomyocyte studies, cells with Ad-GFP can also be infected at the same multiplicity of infection (MOI) as Ad-208 to control for indirect effects caused by adenoviral infection. Since both viruses express green fluorescent protein (GFP), infection efficiencies are also controlled for by epifluorescence microscopy.

Cells are counted under brightfield illumination prior to infection and at 24, 48, 72, and 96 hours post-infection. Cells in 10 fields of vision are counted for both conditions at each time point. Statistical analyses are applied to cell count data. The unpaired Student t-test can be used to determine the probability that the mean number of cells counted per field view differs significantly between Ad-208 and Ad-GFP infection at each particular time point; whereas the paired Student t-test can determine the probability that the mean number of cells counted for each infection differs significantly between time points. If the probability that any two means are significantly different is greater than or equal to 95%, those differences are considered significant.

The cell counting assay is complemented with studies to determine the mitotic index by using phospho-Histone H3 antibodies and to determine the percentage of cells undergoing DNA synthesis by BrdU incorporation. Fixed cells are TUNEL stained to rule out the possibility that miR-208 overexpression causes cell death. Potential outcomes of Ad-208 infection upon cardiomyocyte proliferation are decreased, increased, or no change upon cell number. Without wishing to be limited by theory, it is likely miR-208 expression will stow cardiomyocyte proliferation relative to controls since miR-208 is normally highly expressed in differentiated adult cardiomyocytes.

A set of cardiac transcription factors, including Nkx2.5, MEF2C, GATA4, myocardin, and TBX5, have been shown to be expressed in early differentiating cardiomyocytes, making them early genetic markers of cardiac differentiation. Cardiac muscle-specific contractile proteins, such as α-MHC, β-MHC, α-CA, and MLV2V, are terminal differentiation markers of cardiomyocytes. Some of these cardiac genes are differentially regulated during development. For example, β-MHC is highly expressed in embryonic heart, but becomes down regulated post-neonatally, whereas α-MHC has an opposing expression pattern. In order to determine if miR-208 has a role in regulating cardiac gene expression, the effect of ectopic miR-208 expression upon cardiac marker gene expression in neonatal rat cardiomyocytes is examined. Without wishing to be limited by theory, it is anticipated that miR-208 expression will decrease fetal gene expression and/or promote expression of adult cardiac genes.

Using semi-quantitative reverse transcriptase-PCR (RT-PCR) methods, the relative mRNA transcript levels of various cardiac marker genes in Ad-208 vs. Ad-GFP infected neonatal rat cardiomyocytes are analyzed. cDNA libraries are made from RNA isolated from infected cardiomyocytes by conventional techniques. GAPDH, which is expressed highly in nearly all tissues, is amplified and used to normalize cDNA levels. All PCR primer sets are designed to amplify product that span one or more introns, which will produce a larger PCR amplified product if DNA contamination is present. Additionally, commercially available antibodies are used to examine protein expression levels of various cardiac markers by Western blot analysis to determine if any changes detected in protein expression coincide with changes in mRNA transcript levels.

In addition to studying effects of miR-208 upon cardiac gene expression, any effects upon localization of various cardiac proteins, including transcription factors and structural components are determined. Observation of Ad-208 infected cardiomyocytes suggests that these cells exhibit different morphology to Ad-GFP infected cardiomyocytes (FIG. 16b). The Ad-208 infected cardiomyocytes appeared "rounded" relative their Ad-GFP infected counterparts.

Ad-208 and Ad-GFP infected cardiomyocytes are fixed on glass cover slips, probed with appropriate primary and secondary antibodies, nuclear stained, and mounted to slides for analysis by microscopy.

Inactivating miR-208

In parallel to the miR-208 overexpression studies, the effects of miR-208 inhibition using 2'-O-methyloligonucleotides antisense to miR-208 are studied. 2'-O-methyloligonucleotides act as sequence-specific and irreversible inhibitors of miRNA function in a stoichiometric fashion. This miRNA inhibition system is adapted to cardiomyocytes. Antisense miR-208 2'-O-methyloligonucleotides or, in controls, random 2'-O-methyloligonucleotides are transfected into cardiomyocytes by a cationic lipid reagent, or alternatively by electroporation. A reporter construct with antisense miR-208 sequence attached directly 3' to the luciferase gene (luc-miR-208-sensor) is used as a control and to test the efficacy of the system to block miR-208 function. The mRNA and protein levels, as well as protein localization, are studied as described for the miR-208 overexpression studies.

Example 10 miR-208 is weakly expressed in the embryonic heart and its expression increases dramatically in the adult heart. This example analyzes whether miR-208 function is more important for gene regulation in the developing heart or in the adult heart. During development, one could argue that miR-208 is likely not important since it is expressed weakly in the embryo. Against that argument, proper miR-208 dosage might be critical for regulating certain genetic pathways during development. Furthermore, the knockout mouse of its host gene α-MHC, which is weakly expressed during development relative to the adult stage, suffered embryonic lethality, though it is not known whether expression of miR-208 is affected in those animals[87]. The high expression of miR-208 detected in the adult heart might indicate that its most important function lies in later development. To sort through these types of issues, two mouse models are created to study miR-208 function: a miR-208 knockout mouse and a transgenic mouse that conditionally overexpresses miR-208.

miR-208 Knockout Mouse Design

A mouse functionally null for miR-208 is designed and created without affecting the expression of its host gene α-MHC. The production of embryonic-stem cell derived miR-208 knockout mice is a three-stage process: production of the targeting vector; introduction of DNA sequences into embryonic stem cells by homologous recombination; and production of genetically modified mice derived from embryonic stem cells. Related miRNAs are grouped into families based on sequence homology within their seed regions. These families might redundantly regulate the expression of the same genes, potentially complicating genetic analysis of their function in vivo. The seed region of miR-208 does not cluster with other known miRNAs in a phylogenetic tree, making miR-208 a suitable miRNA knockout candidate.

The miR-208 targeting construct is built using a strategy called recombineering, which uses homologous recombination between linear DNA fragments and circular plasmids[88, 89]. The circular plasmid can contain a 6-7 kb fragment of the α-MHC gene that miR-208 lies within centrally. The linear DNA fragment contains two homologous arms designed to replace the 22 nt miR-208 sequence with a floxed selection cassette. Bacteria transformed with the circular plasmid are electroporated with the linear DNA fragment, and subsequently, resistance encoded by the linear fragment selects for recombinant colonies. The resulting construct is used to target ES cells by homologous recombination. Once a heterozygous ES cell is identified using a PCR-based screening or by Southern blot, it is used to generate chimera by blastocyst injection. The presently disclosed knockout design leaves only a small footprint of exogenous DNA within the intron of α-MHC and helps ensure that transcription of α-MHC or the splicing pattern of α-MHC mRNA remains unaffected.

Conditional Transgenic Mouse Design

Figure 17:
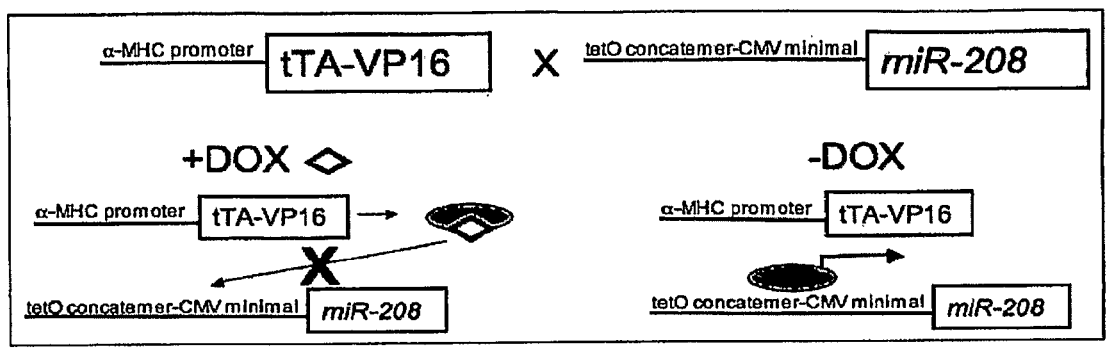
FIG. 17 shows a diagram of a conditional transgenic system disclosed herein. Two independent lines of transgenic lines of mice are utilized: one expressing tTA-VP16 fusion protein under the control the α-MHC promoter, and a second line harboring the miR-208 transgene under the control of a CMV minimal promoter. The CMV minimal promoter has several repeats of the tetracycline operon (tetO) located directly upstream. The two lines are bred together and yield, assuming a Mendelian inheritance pattern, 1 in 4 mice that are double transgenic. If doxycycline (DOX) is administered to a double transgenic mouse, the tTA-VP16 protein is bound by DOX and transcription of miR-208 is inhibited. If DOX is absent, the tTA protein binds the tetO concatemer, which allows the VP16 domain to induce miR-208 transcription from the CMV minimal promoter. Cardiac-specific target gene expression can be turned on or off by addition or withdrawal of DOX. Adapted from James et al Am J Physiol 273: H2105-H2118, herein incorporated by reference.

The conditional transgenic strategy is diagrammed in FIG. 17. The conditional transgenic approach is a binary system consisting of two transgenes. One transgene encodes miR-208 (tet208), while the other transgene encodes a transactivator (tTA) that activates the miR-208 transgene by binding a regulatory sequence within its promoter. Binding of tTA is inhibited whenever doxycycline (DOX) is present (i.e. "tet-off"), thus enabling temporal regulation of miR-208 transgene by DOX treatment.

A mouse colony homozygous for the miR-208 transgene is established. The tet208 mice is mated to transgenic mice harboring a tTA transgene to create double transgenics for study. Assuming Mendelian genetics, 1 in 4 offspring will be double transgenic and express miR-208 wherever tTA is expressed. An p-MHC promoter is utilized to direct tTA expression. The α-MHC promoter has been well-characterized and is sufficient to properly direct tissue-specific expression in early development[90]. Using the α-MHC promoter to express tTA will increase miR-208 dosage in the same tissues as endogenous miR-208 in the double transgenic animals, since endogenous miR-208 normally originates from an intron within the α-MHC gene. A transgenic mouse line that uses the mouse α-MHC promoter to direct tTA expression exists and has been used successfully[91,92]. The tet208 transgenic mouse line allows us to study the dosage effects of miR-208 expression in the developing embryo or adult mouse heart independently. Typically, early embryonic lethality in regular transgenic founders would severely limit the number of developmentally arrested embryos available for study and hinder phenotypic analysis. With the conditional strategy, we are able to delay miR-208 transgene expression in the double transgenic mice should earlier miR-208 overexpression prove lethal.

Analysis

The specific analyses conducted depend upon how the phenotypes are manifested. In general, using histological and biochemical approaches to characterize potential phenotypes in the developing embryo and/or adult is acceptable. Hearts are examined for gross abnormalities and sectioned for histological analysis to identify potentially more subtle developmental defects. The possibilities for defects are innumerable and can include anything from defective septal formation to thickened atria. It is equally possible that the phenotype can be a contractility defect that can be characterized by electrophysiological studies.

Example 11

The identification of direct molecular targets of miR-208 facilitates understanding of the mechanism underlying its biological function. Target predictions are utilized to complement observations related to the investigation of miR-208 function in vitro and in in vivo mouse models.

Without wishing to be limited by theory, it is hypothesized that Thrap1 expression is regulated by miR-208. The 3' UTR of Thrap1 contains two predicted miR-208 binding sites (FIG. 18). The two targets are located ~80 by downstream of the Thrap1 stop codon and are separated from one another by only ~50 bp. Both targets are perfectly complementary with the seed region of miR-208. The Thrap1 gene encodes a 240 kd subunit of the TRAP (thyroid hormone receptor protein) complex that is ubiquitously expressed[93]. TRAP is a multi-subunit protein complex that is a coactivator for nuclear receptors. TRAP was initially characterized for the thyroid hormone nuclear receptor[94]. Thrap1 has not been characterized, but defects in other TRAP subunits have been shown to affect nuclear receptor signaling. Gene ablation of TRAP220 in mice impaired heart and nervous system development, while Drosophila homologues of TRAP230 and TRAP240 are required for proper eye-antennal disc development[95,96]. Mutations in a gene highly similar to Thrap1, termed Thrap2, were found in patients with the congenital heart defect Transposition of the Great Arteries[97]. Thus, TRAP family members are important for proper development. Of particular interest is Thrap1 as a target of miR-208, since the thyroid hormone is known to exert profound effects upon cardiac contractility.

Figure 19:
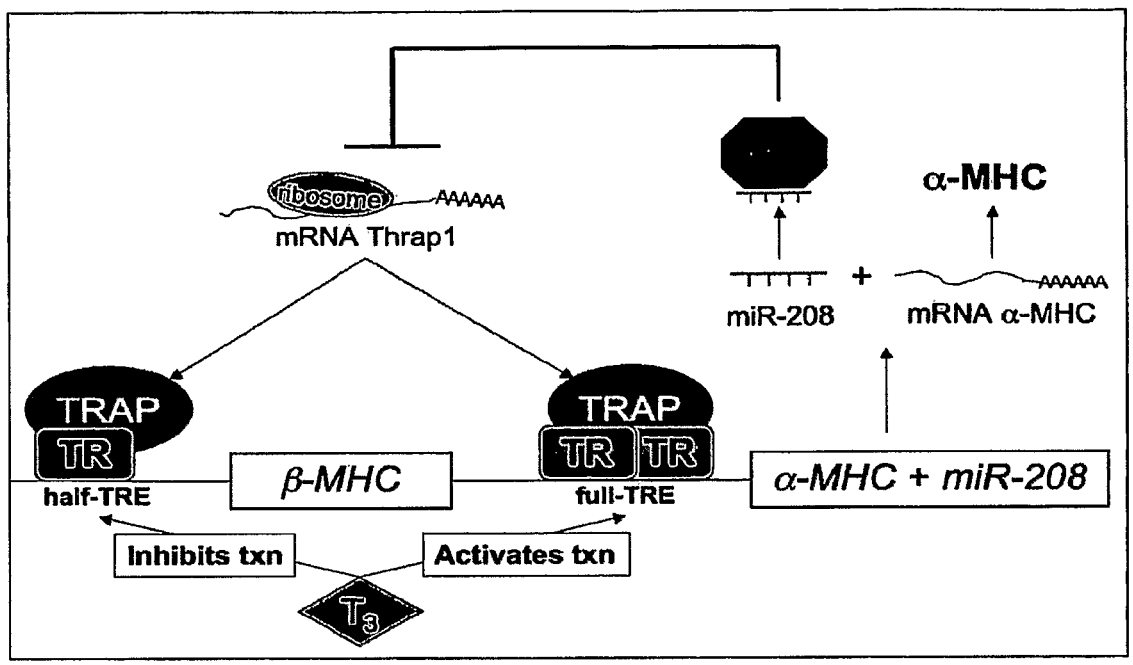
FIG. 19 shows a model of miR-208 regulation of cardiac myosin heavy chain isoform switching. Thyroid hormone nuclear receptors (TR) bind to Thyroid Receptor Elements (TREs) sequences within the promoters of the α-MHC and β-MHC genes. The α-MHC promoter contains a full-TRE bound by two TRs, while the β-MHC has is bound by a single TR at a half-TRE. TR monomers and dimers both can heterodimerize with the TRAP complex, a TR cofactor. Thyroid hormone ($T_3$) binds TRs and inhibits transcription of β-MHC while inducing α-MHC expression. miR-208 is concurrently expressed with α-MHC protein and is predicted to regulate translation of Thrap1, the largest subunit of the TRAP complex. It is believed that miR-208 is a component of a negative feedback loop that regulates cardiac myosin heavy chain isoform expression by inhibiting $T_3$ signaling.

Thyroid hormone is linked to cardiac myosin isoform switching. In cardiomyocytes, thyroid hormone causes a rapid accumulation of α-MHC mRNA while simultaneously inhibiting β-MHC expression[98,99]. Several positive acting thyroid response elements (TREs) are located within the α-MHC promoter and a negative acting half-TRE within the β-MHC promoter has been identified[100,101]. The α-MHC and β-MHC genes are arranged in tandem on chromosome 14 and they encode the two cardiac myosin heavy chain isoforms that convert ATP to mechanical work at different rates and their protein expression ratio affects the contractility of the cardiac sacromeres; α-MHC is "fast" whereas β-MHC is "slow." Their expression is developmentally regulated. In mouse and rat, β-MHC is predominant in late fetal life, but shortly after birth α-MHC becomes the predominant adult cardiac isoform. The transition is likely caused by the surge of circulating thyroid hormone occurring shortly after birth[98]. In larger mammals, like rabbits and humans, β-MHC is the predominant adult cardiac isoform. However, the promoters of the α-MHC and β-MHC genes are highly conserved between mouse and human, suggesting that they are regulated similarly. Given the origin of miR-208 from an α-MHC intron, and without wishing to be bound by theory, it is possible that miR-208 acts as a tissue-specific inhibitor of thyroid hormone signaling in a negative feedback loop to regulate the ratio of cardiac myosin heavy chain isoforms by targeting a component of the TRAP complex (FIG. 19).

The initial screening strategy asks whether overexpression of miR-208 downregulates expression of a reporter gene bearing putative target sites in its 3' UTR. We have inserted the Thrap1 3' UTR directly behind the coding sequence of a constitutively expressed luciferase reporter gene. Results suggest that miR-208 targets the Thrap1 UTR (FIG. 18). To confirm this observation, we have mutated the seed regions of the two putative target sites within the Thrap1 UTR, separately and in combination. The mutated polynucleotide can be tested to determine if they can alleviate miR-208 mediated repression.

Previous studies have shown that thyroid hormone transcriptionally activates α-MHC chain expression and inhibits β-MHC expression in cardiomyocytes[98,99,102]. Cardiomyocytes are infected with Ad-208 to determine whether miR-208 expression inhibits thyroid hormone signaling by monitoring transcript and protein levels of α-MHC and β-MHC. Inhibition of α-MHC expression by miR-208 would indirectly support our hypothesis that miR-208 targets a component of the thyroid hormone signaling pathway.

To further validate predicted targets, it can be determined whether miR-208 expression decreases mRNA or protein levels in hearts from the miR-208 knockout and miR-208 transgenic mouse models. Specific antibodies against the targeted proteins are employed. Human Thrap1 is commercially available. If not effective in mouse studies, mouse Thrap1-specific antibodies are developed.

Additional Candidate Targets for miR-208

In addition to Thrap1, we have cloned the 3' UTRs of four other interesting miR-208 predicted targets directly to the luciferase gene for reporter studies. The 3' UTRs are from SP3 (Sp3 trans-acting transcription factor 3), EYA4 (eyes absent homolog 4), CSNK2A2 (casein kinase 2, alpha prime polypeptide), and TTN (Titin).

SP3 protein expression is opposite to miR-208 expression; SP3 is a transcription factor that interacts with a variety of promoters containing GC-boxes[103,104,105]. SP3 protein is readily detected in fetal mouse hearts, but is barely detectable in the adult heart. The opposing expression patterns of SP3 and miR-208 makes it formally possible for miR-208 to regulate SP3 translation.

EYA4 is an interesting potential target of miR-208 given its established link to pathology in the human heart. Mutations have been identified in human EYA4 that cause dilated cardiomyopathy and associated heart failure[106,107]. EYA4 is a transcriptional coactivator that interacts with members of the sine-oculis family (Six1-Six6) and Dach transcription factors leading to gene activation[108,109]. The characterization of the human mutation was supported by work in zebrafish, as attenuated EYA4 levels produced morphological and hemodynamic features of heart failure[106]. Currently, no potential downstream cardiac genes of EYA4 have been identified.

CSNK2A2 is a broadly expressed protein serine/threonine kinase that has been implicated in DNA replication, regulation of basal and inducible transcription, translation and control of metabolism[110,111]. We are interested in CSKN2A2 for its potential in regulating a variety of genetic pathways.

Similar to EYA4, TTN is also an interesting miR-208 target candidate given its established association with cardiovascular function and pathology. TTN is a giant sacromeric protein expressed in both cardiac and skeletal muscle tissue and is important for sacromere assembly and force transmission[112]. Mutations in TTN have been linked to hypertrophic and dilated cardiomyopathies. Given the requirement of TTN for cardiac and skeletal muscle function, we doubt that miR-208 strongly regulates TTN expression, but it is possibly that that one sacromeric gene (i.e. α-MHC) might fine-tune the expression of another (i.e. TTN) to adjust the contractile properties of cardiomyocytes.

The 3' UTR of the predicted target gene is tested by reporter assay to determine if it confers miR-208-mediated suppression. Candidate genes are further characterized by mutating the predicted target sites and testing whether miR-208 suppression is diminished. After the initial reporter screening of candidate targets, the effects of miR-208 overexpression in vitro using cardiomyocyte cells upon the candidate gene expression at the transcript and protein levels are analyzed. The biological relevance of verified targets are studied in vivo using our miR-208 knockout and inducible transgenic mouse models. Analysis of potential miR-208 targets in vitro and in vivo can validate target predictions and confirm their biological relevance in order to understand the genetic pathways regulated by miR-208 in the heart.

Example 12

Skeletal muscles are damaged and repaired repeatedly throughout life. Muscle regeneration maintains locomotor function during aging and delays the appearance of clinical symptoms in neuromuscular diseases, such as Duchenne muscular dystrophy. This capacity for tissue repair is conferred by a subset of stem cell-like cells called satellite cells located between the basal lamina and the sarcolemma of mature myofibers. Upon injury, satellite cells reenter the cell cycle, proliferate, and then exit the cell cycle either to renew the quiescent satellite cell pool or to differentiate into mature myofibers. Both the cell proliferation and differentiation programs are essential for myogenesis.

The presently disclosed subject matter provides data demonstrating that miRNAs are responsive for the proliferation and differentiation of muscle cells.

Methods:

Cardiotoxin was injected into the tibialis anterior (TA) muscles of 6-week-old male C57BL/6 mice according to Yan et al.[114] The muscles were harvested 3 days after injection. Uninjected TA muscles were used as control. Total RNA was extracted from TA muscle and 5 µg was used for microarray analysis of microRNAs.

Figure 20:
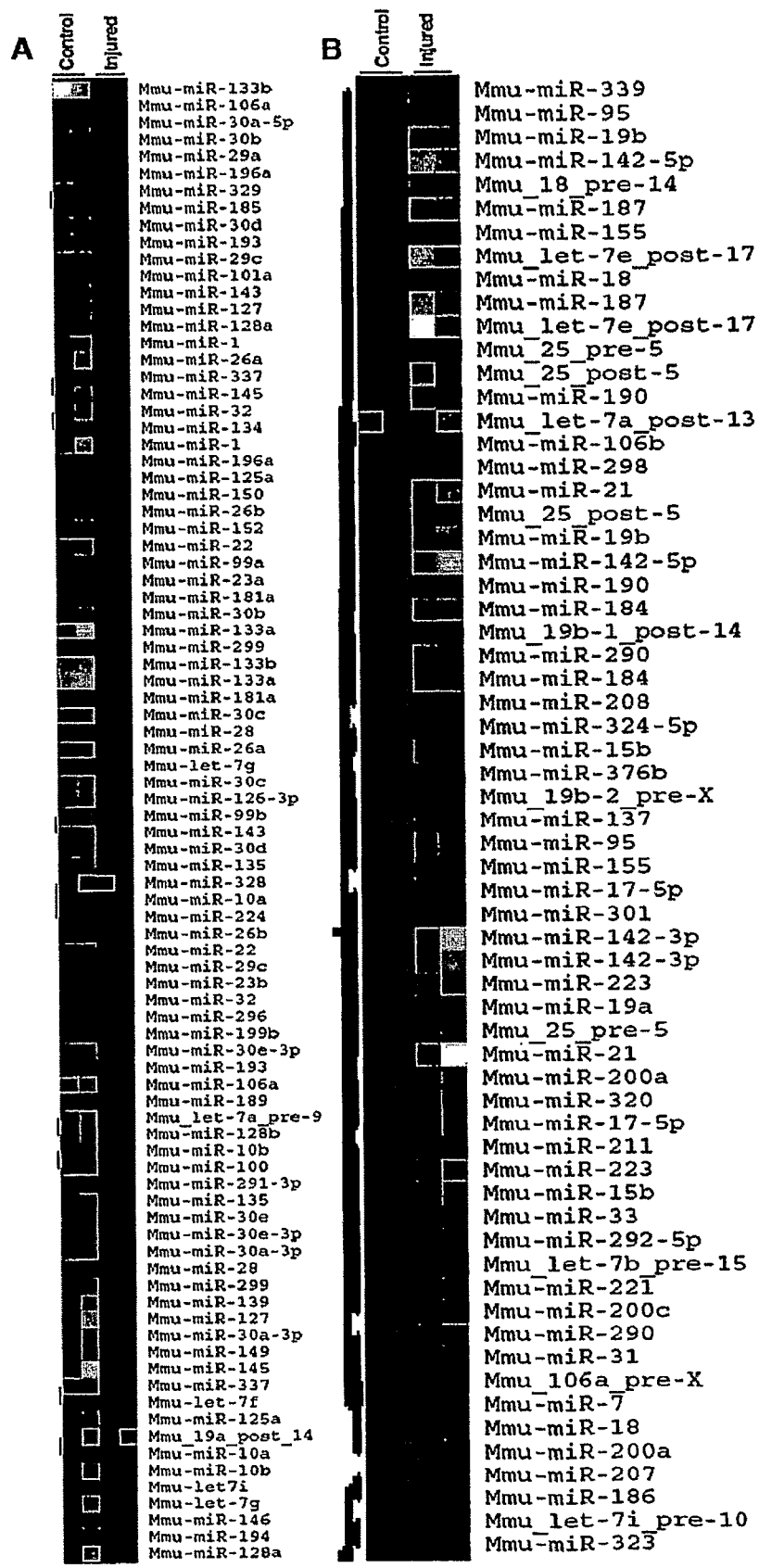
FIGS. 20A and 20B show data from miRNA array analysis of injured/regenerated skeletal muscle.

Results:

FIGS. 20A and 20B show miRNA array expression data from cardiotoxin injected (Injured) or uninjected (Control) tibialis anterior (TA) muscle. Normalized log (base 2) data was hierarchically clustered by gene and is plotted as a heat map. The range of signal was from −4 fold to +4 fold. Light shading denotes high expression and dark shading denotes low expression, relative to the median. FIG. 20A shows miRNAs that are down-regulated in injured muscle and FIG. 20B shows miRNAs that are up-regulated in injured muscle.

Example 13

Skeletal muscle satellite cells are a group of small mononuclear cells positioned between the plasma membrane and the surrounding basal lamina of mature, multinuclear muscle fibers. Satellite cells have long been considered as the precursor cells of adult skeletal muscle. Recent evidence supports the notion that satellite cells are heterogeneous and have stem cell-like potential. These cells are maintained in a quiescent state, but once activated, will proliferate extensively to form a pool of myoblasts that will differentiate and regenerate or repair muscle tissue.

The genetic pathways and molecular mechanisms that maintain satellite cells in their inactive quiescent state under normal conditions, as well as how they become activated in response to muscle injury to facilitate muscle regeneration are beginning to be revealed. Pax3 and Pax7, members of a family of paired box/homeodomain transcription factors, have been demonstrated to play important yet distinct roles in mediating the satellite cell-related skeletal muscle regeneration process. It is less clear, however, how the expression of Pax proteins are regulated during the course of satellite cell maintenance and activation. Intriguingly, the expression of Pax3 and Pax7 is down regulated in differentiating myoblasts. More importantly, ectopic overexpression of Pax3 or Pax7 in C2C12 myoblast blocks their differentiation. Those observations suggest that the status of satellite cell quiescence and self-renewal as well as myoblast proliferation and differentiation is under tight transcriptional and post-transcriptional control.

In addition, brain-derived neurotrophic factor (BDNF) is expressed in the skeletal muscle satellite cells and inhibits myogenic differentiation. It was found and is now disclosed herein that both Pax7 and BDNF are putative regulatory targets for miR-1/206, implicating the miR-1/206 plays a vital role in skeletal muscle satellite cell regulation.

Establish miRNA Overexpression and Detection System in Satellite Cells

Figure 23:
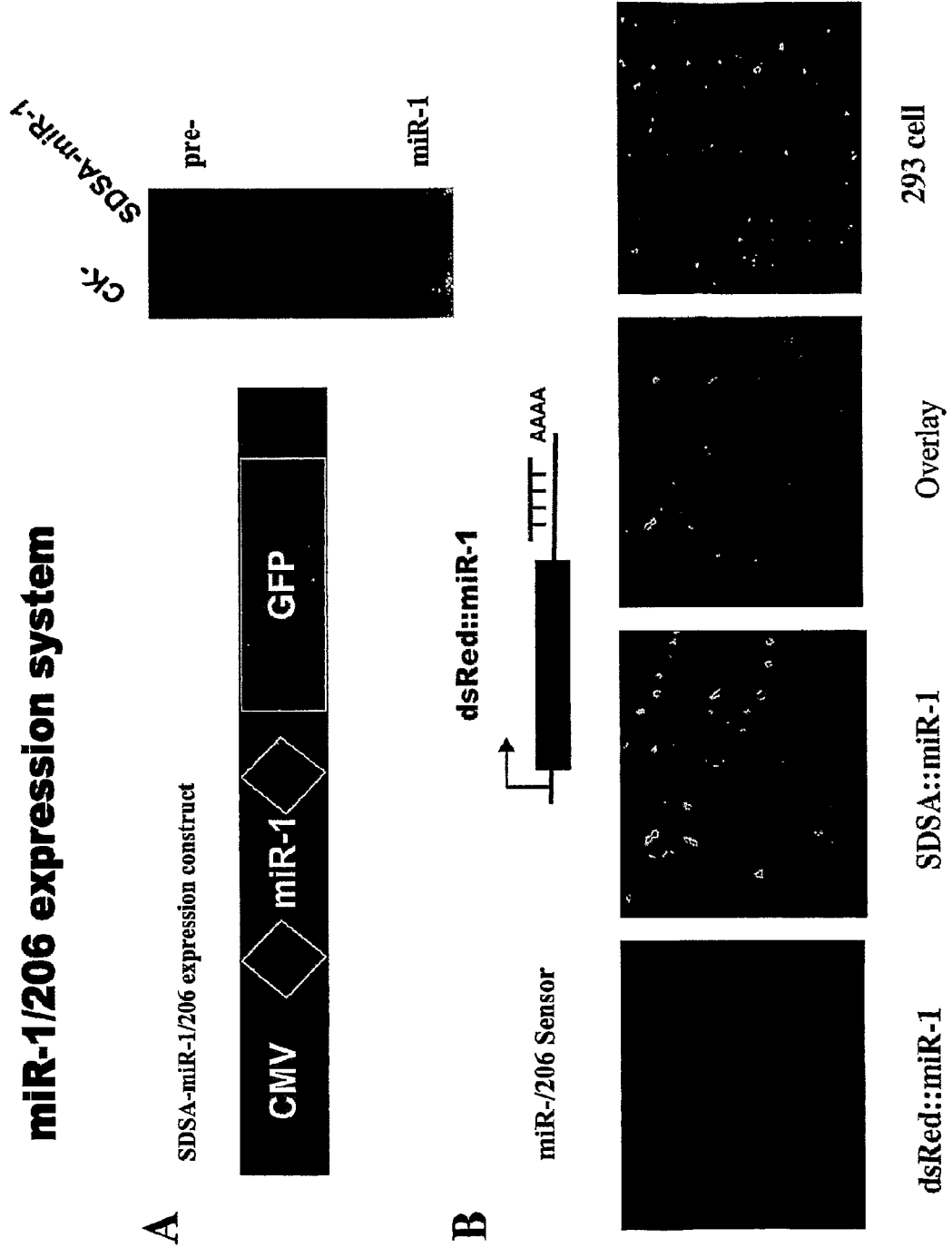
FIGS. 23A and 23B show data demonstrating the establishment of miR-1/206 expression system (FIG. 23A) and miR-1/206 sensor (FIG. 23B).

In order to efficiently everexpress miRNAs into satellite cells ectopically, a retroviral-based overexpression system was adapted. The genomic sequences flanking miR-1 and miR-206 (around 300-400 bp) are flanked with a splice donor (SD) and a splice acceptor (SA) within a murine stem cell virus (MSCV)-derived retrovirus vector in which a green fluorescent protein (GFP) coding sequence is located downstream of miRNA-SDSA sequence. In this way, both miR-1/206 and GFP will be expressed simultaneously and the expression of GFP will serve as an excellent indication of miR-1/206 expression (FIG. 23).

Figure 22:
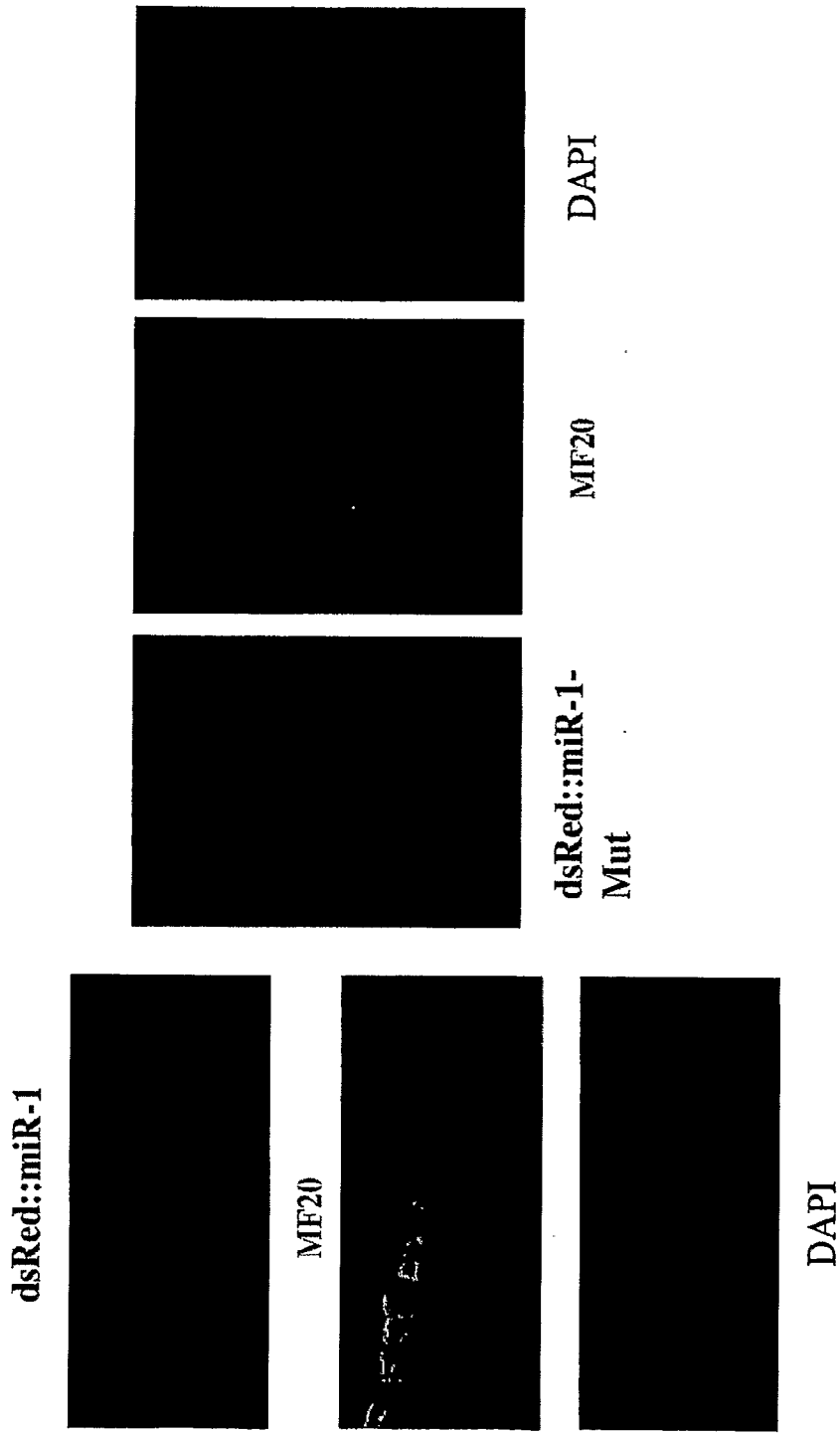
FIG. 22 shows data demonstrating the expression of miR-1 in differentiating skeletal muscle satellite cells using a miRNA sensor. Satellite cells stably expressing the miR-1 sensor (dsRed::miR-1) or the mutant sensor (dsRed::miR-1-Mut) were induced to differentiate by transferring into differentiation medium, in which bFGF was removed, and images were obtained using fluorescence to show expression of the dsRed reporter gene (dsRed::miR-1) or muscle differentiation marker gene myosin heavy chain (MF20). Low expression of dsRed in the sensor expressed differentiating cells indicates the expression of miR-1 in those cells. DAPI stains the cell nuclei.

In order to monitor the expression and the inhibitory effect of miRNAs in satellite cells, we created a "miRNA sensor" in which the expression of a dsRed gene is under the transcriptional control of a constitutively active CMV promoter. The complementary sequence of the miR-1/206 was linked to the 3' of a dsRed reporter gene and inserted into a MSCV-derived retrovirus vector so that a functional miRNA will repress the translation of dsRed protein (FIG. 22). Using this system, we can precisely detect the expression and inhibitory effect of a miRNA in satellite cells, which provide us powerful tools to further study the function of miRNAs in skeletal muscle.

Pax7 and BDNF are Regulatory Targets of miR-1/206 in Satellite Cells

Figure 24:
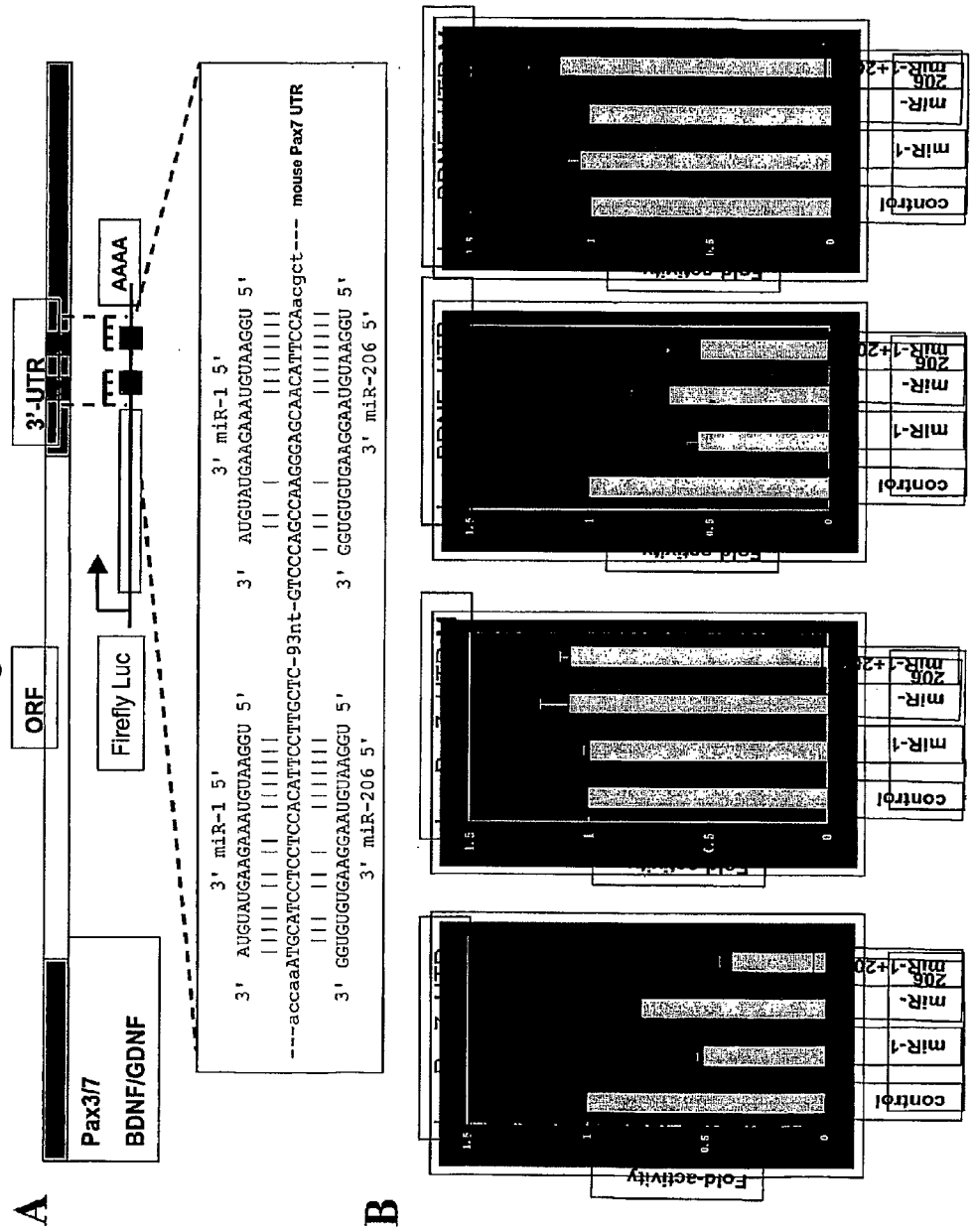
FIGS. 24A and 24B depict data showing the repression of Pax7 and BDNF 3' UTRs by miR-1/206.
Figure 25:
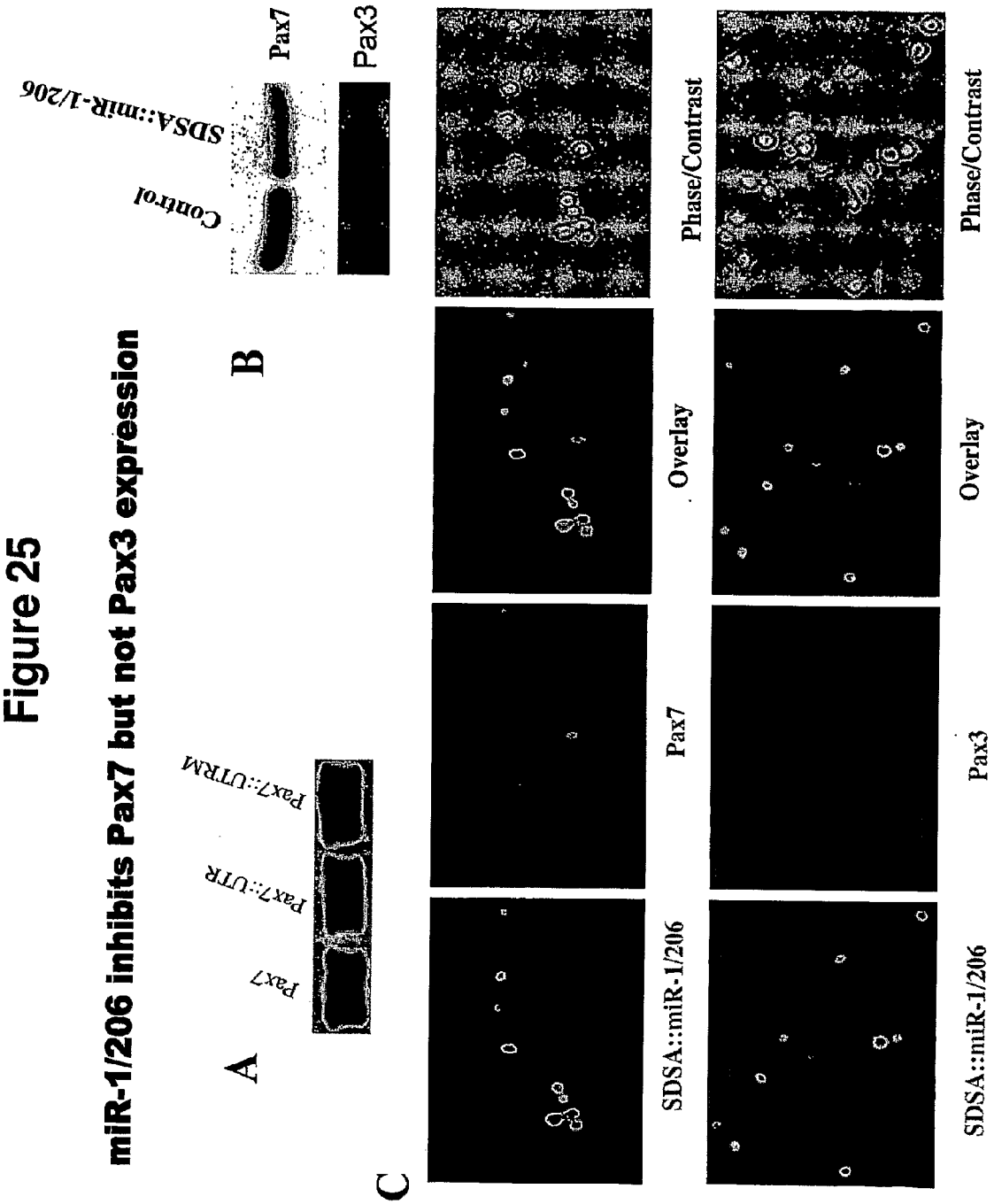
FIGS. 25A-25C show miR-1/206 inhibits the expression of Pax7, but not Pax3, in satellite cells.
Figure 26:
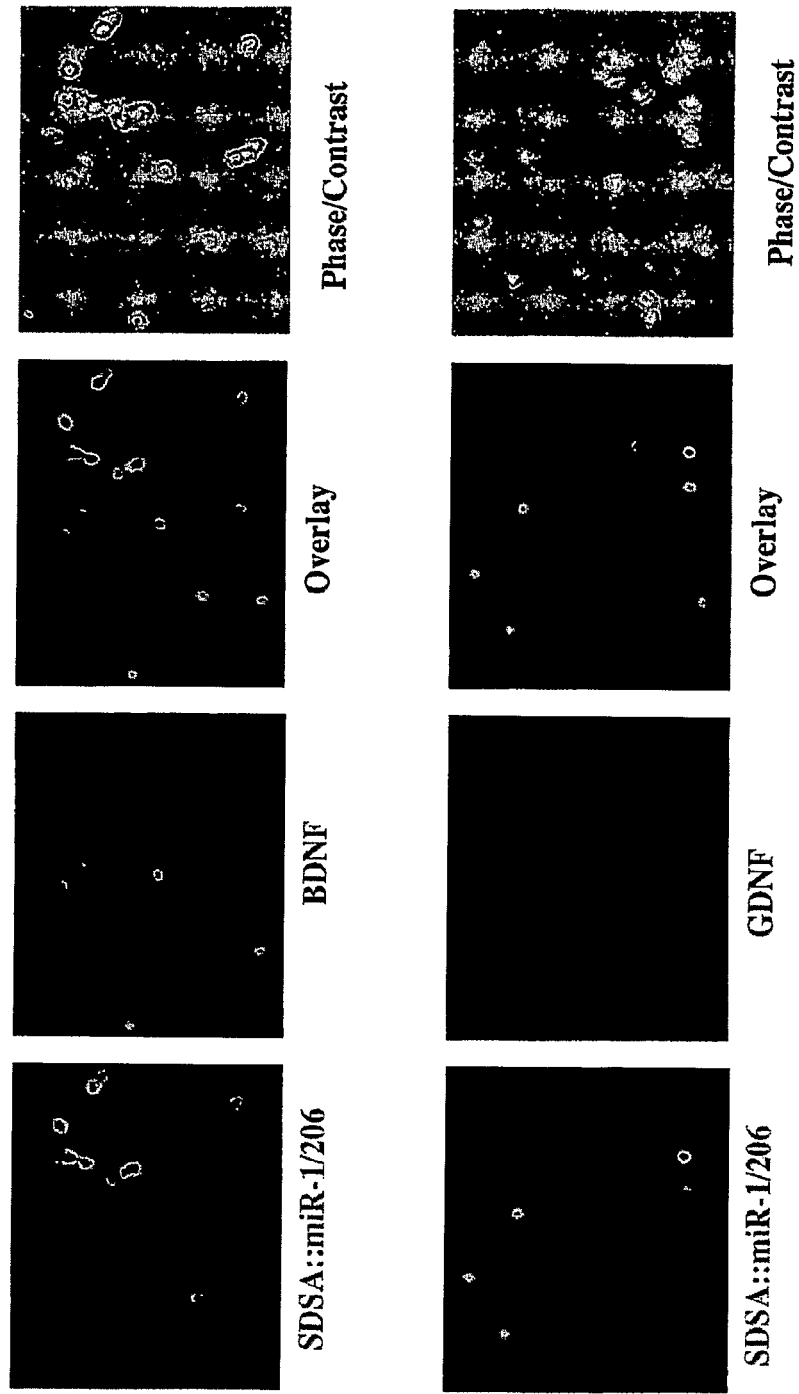
FIG. 26 shows miR-1/206 inhibits the expression of BDNF but not GDNF in satellite cells. Images were obtained using phase contrast (Phase/Contrast panels) or fluorescence to show expression of the BDNF or GDNF proteins (BDNF and GDNF panels) or miRNA::GFP (SDSA::miR-1/206 panels) or overlay (Overlay panels) in skeletal muscle satellite cells. Note the expression of BDNF, but not GDNF, is inhibited by miR-1/206.

We found that Pax7 and BDNF genes contain highly conserved miR-1/206 target sites in their 3' UTRs (FIGS. 24, 25, 26). We cloned these 3' UTR sequences into a luciferase reporter and tested whether they can be repressed by the miRNAs. As shown in FIG. 24, both miR-1 and miR-206 potently repress these reporters. miRNA-mediated repression is abolished when the conserved miRNA binding sequences were mutated, indicating the specificity of the repression. These data suggest that miR-1/206 can control the proliferation and differentiation of muscle cells and/or their precursors by repressing important target genes.

Isolation of Satellite Cells from Single Skeletal Muscle Myofibers

Figure 28:
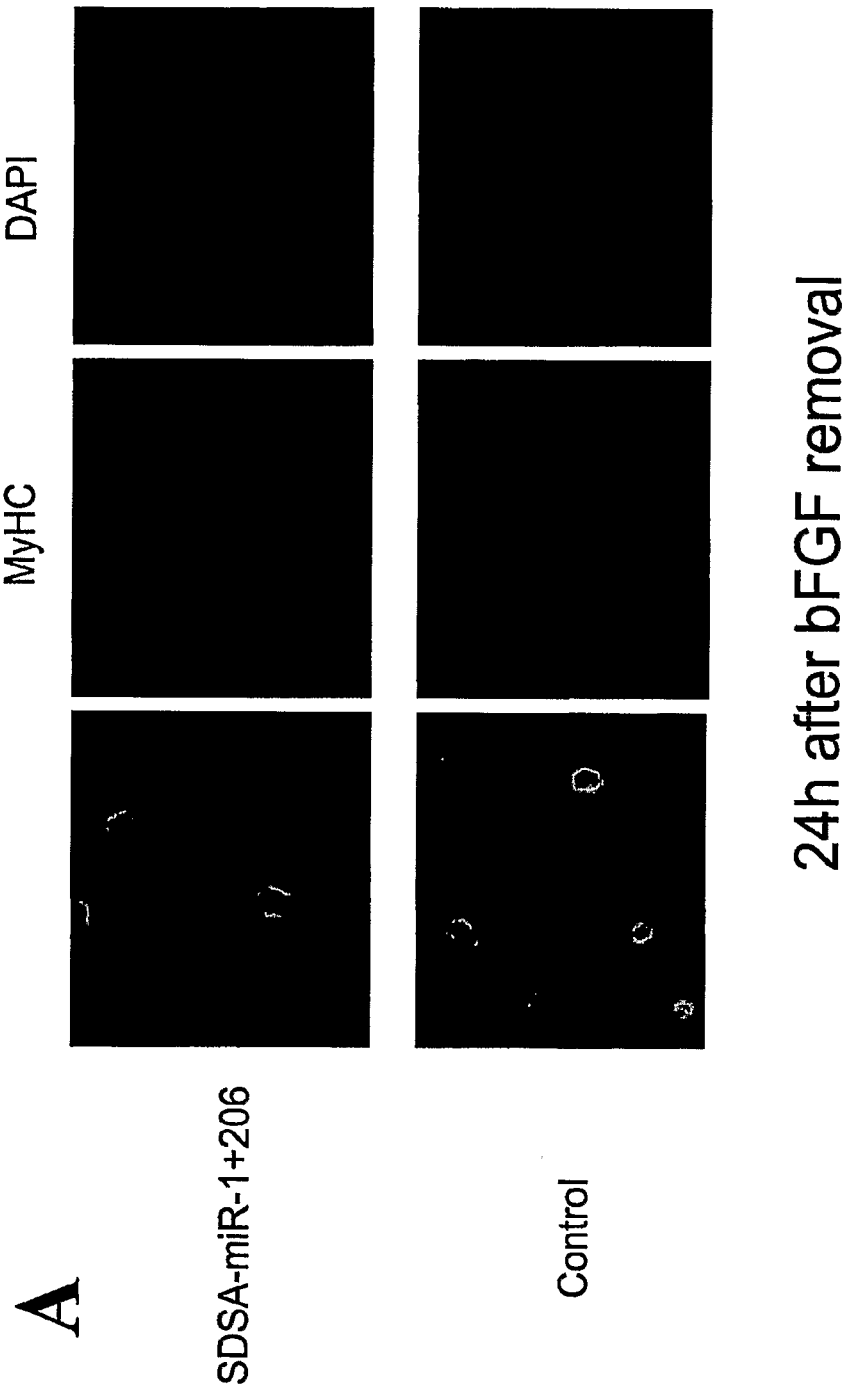
FIGS. 28A and 28B show that miR-1/206 enhances satellite cell differentiation.
Figure 28:
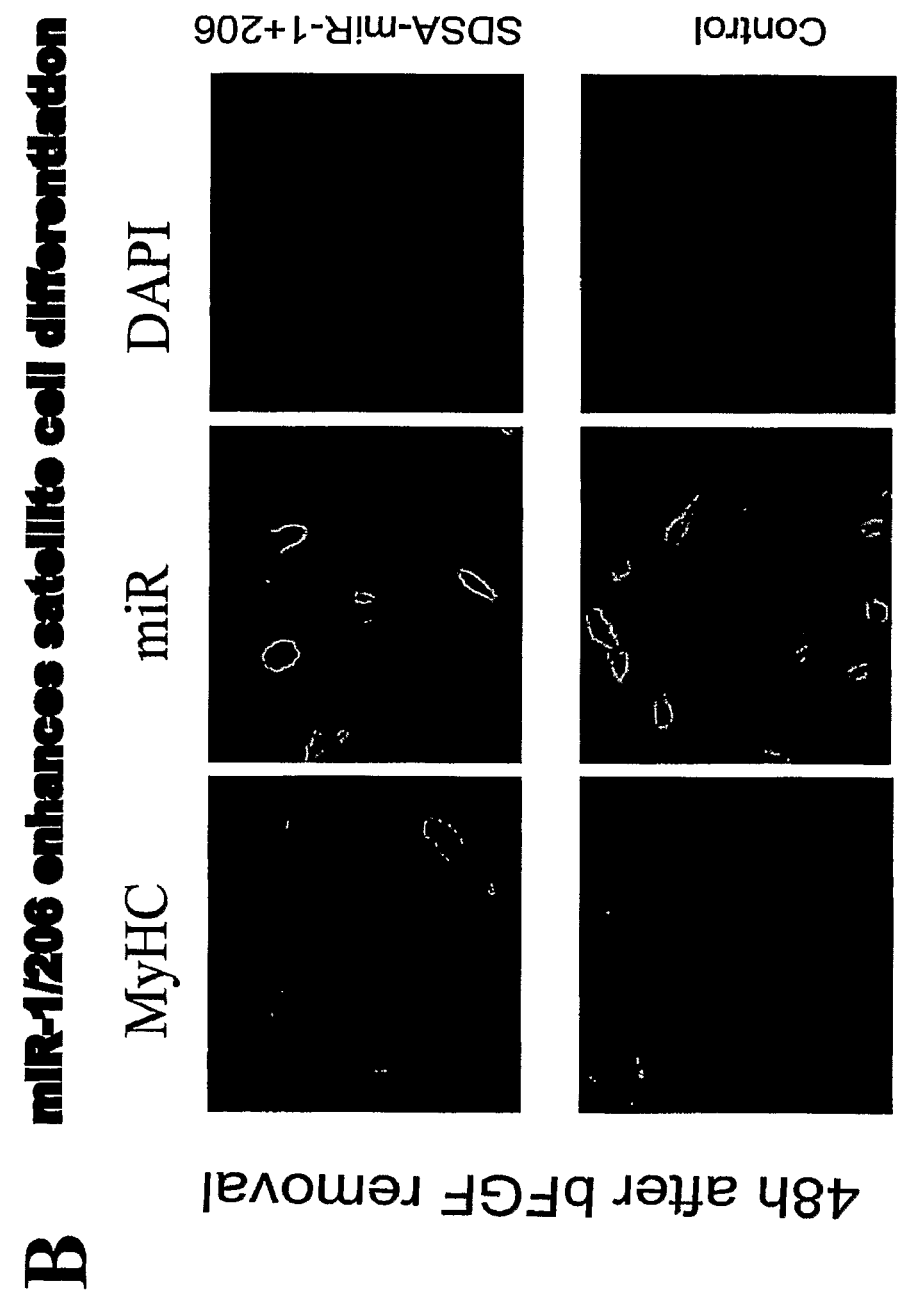

Satellite cells are adult skeletal muscle progenitor cells responsive to postnatal growth and regeneration. Without wishing to be limited by theory, we hypothesize that miRNAs are also regulators of satellite cells. To test this hypothesis, we began isolating satellite cells from hindleg or diaphragm skeletal muscle of neonatal or adult mice. We are able to isolate satellite cells from single myofibers, which yields purest satellite cell population and provides reproducible results. These satellite cells could be maintained in an undifferentiated status when bFGF was included in the culture medium, in which the expression of Pax7 and other satellite cells markers can be detected. However, they can be induced to differentiate into myoblasts and myotubes upon growth factor bFGF removal, faithfully mimic skeletal muscle differentiation process in vitro (FIG. 28).

miR-1/206 Inhibits the Proliferation of Satellite Cells

To define the function of miR-1/206 in skeletal muscle progenitor cells, the satellite cells isolated from single myofibers of adult mice are plated on 24 well tissue culture plates and miR-1/206 is introduced into the cells using a SDSA vector-based retrovirus. The expression and activity of ectopically expressed miRNAs is monitored in several ways: Northern blot analysis was applied to detect and quantitatively measure the expression of miR-1. The activity of miR-1/206 is also monitored using "sensor" reporters in which the complementary sequence for miR-1/206 is cloned 3' toward a dsRed reporter gene.

Figure 27:
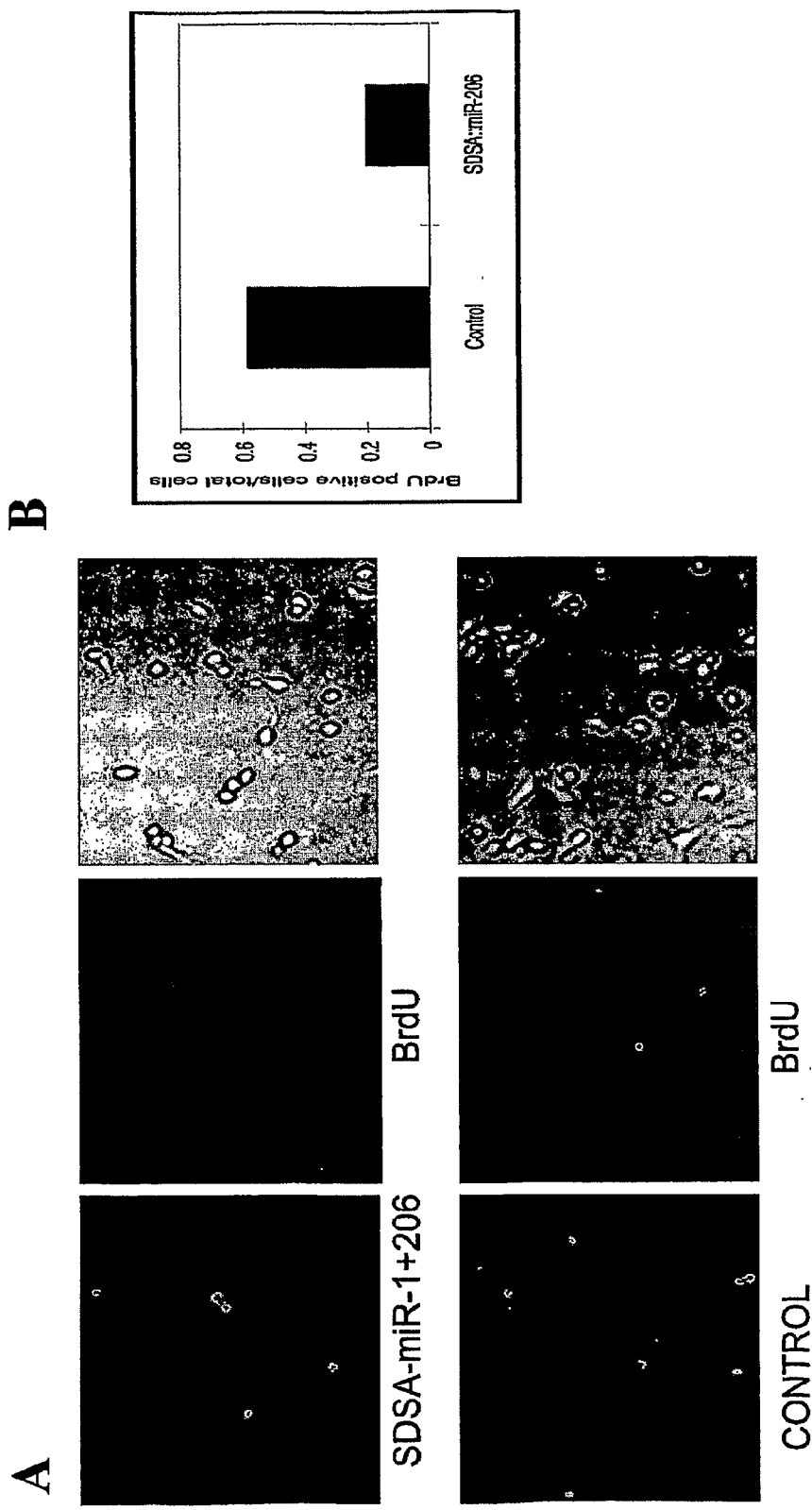
FIGS. 27A and 27B show miR-1/206 inhibits satellite cell proliferation.

For proliferation assays, satellite cell culture was labeled with BrdU 1 hr before harvesting. The cells were then fixed and proliferating cells measured by counting BrdU positive staining cells. As shown in FIG. 27, overexpression of miR-1/206 in satellite cells inhibits their proliferation.

miR-1/206 Enhances the Differentiation of Satellite Cells

Figure 29:
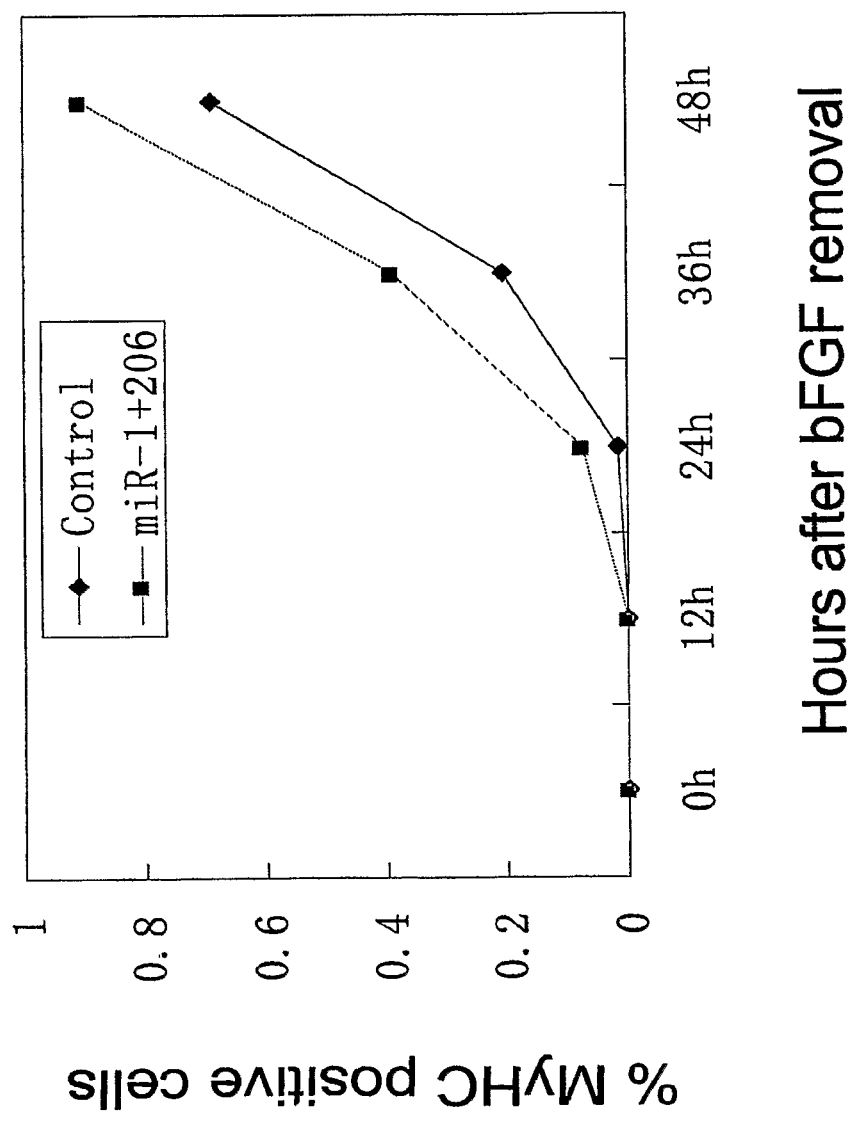
FIG. 29 is a graph showing results of experiments wherein overexpression of miR-1/206 enhances satellite cell differentiation kinetics. Satellite cells either overexpress miR-1/206 (■) or GFP (Control; ♦) were cultured in growth medium or transferred to differentiation medium, where bFGF was removed, at different time points (0, 12, 24, 36 and 48 hrs) and myosin heavy chain (MyHC) positive cells were scored. Results were presented as ratios of MyHC positive cells versus total cells.

For differentiation kinetics analysis, the satellite cells from single myofibers were plated on collagen coated 24 well plates in DMEM plus 20% FBS and 10 ng/ml of bFGF. Cells were plated at a density around $5 \times 10^3$ cells/cm$^2$ and infected with the miR-1/206 retroviruses or control retrovirus. Once the bFGF is removed from the culture medium, satellite cells will spontaneously exit cell cycle and differentiate. As shown in FIGS. 28 and 29 overexpression of miR-1/206 enhances the differentiation of satellite cells and accelerates their differentiation kinetics.

Figure 30:
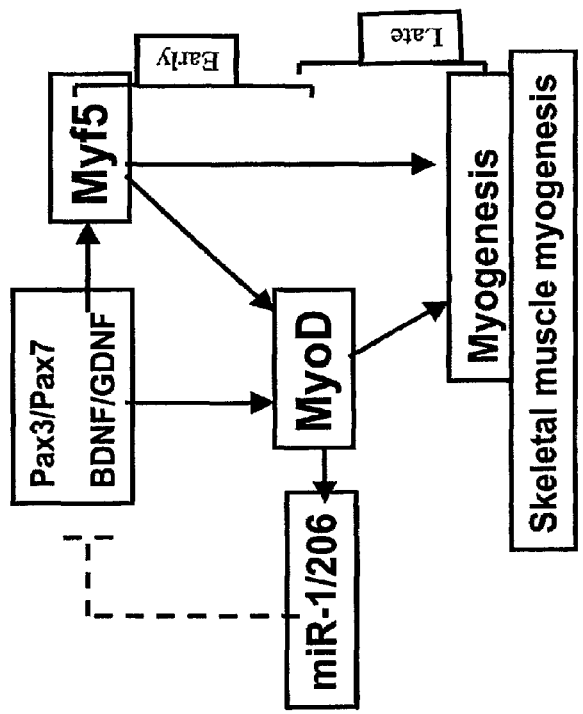
FIG. 30 shows a model for miR-1/206 in regulation of skeletal muscle satellite cell proliferation and differentiation.

In summary, the data set forth in the present Example demonstrate that miR-1 and miR-206 play an important role in controlling skeletal muscle satellite cell proliferation and differentiation process. Given the critical function of satellite cells in skeletal muscle regeneration and repair process, it is suggested, and without wishing to be limited by theory, that miR-1, miR-206 and miR-133 are important for skeletal muscle regeneration (FIG. 30).

REFERENCES

The references listed below as well as all references cited in the specification are incorporated herein by reference to the extent that they supplement, explain, provide a background for or teach methodology, techniques and/or compositions employed herein.

1. Bartel, D. P. MicroRNAs: genomics, biogenesis, mechanism, and function. *Cell* 116, 281-97 (2004).
2. Ambros, V. The functions of animal microRNAs. *Nature* 431, 350-5 (2004).
3. Lee, R. C., Feinbaum, R. L. & Ambros, V. The *C. elegans* heterochronic gene lin-4 encodes small RNAs with antisense complementarity to lin-14. *Cell* 75, 843-54 (1993).
4. Wightman, B., Ha, I. & Ruvkun, G. Posttranscriptional regulation of the heterochronic gene lin-14 by lin-4 mediates temporal pattern formation in *C. elegans*. *Cell* 75, 855-62 (1993).
5. Chen, C. Z., Li, L., Lodish, H. F. & Bartel, D. P. MicroRNAs modulate hematopoietic lineage differentiation. *Science* 303, 83-6 (2004).
6. He, L. et al. A microRNA polycistron as a potential human oncogene. *Nature* 435, 828-33 (2005).
7. Giraldez, A. J. et al. MicroRNAs regulate brain morphogenesis in zebrafish. *Science* 308, 833-8 (2005).
8. Zhao, Y., Samal, E. & Srivastava, D. Serum response factor regulates a muscle-specific microRNA that targets Hand2 during cardiogenesis. *Nature* 436, 214-20 (2005).
9. Thomson, J. M., Parker, J., Perou, C. M. & Hammond, S. M. A custom microarray platform for analysis of microRNA gene expression. *Nat Methods* 1, 47-53 (2004).
10. Blau, H. M. et al. Plasticity of the differentiated state. *Science* 230, 758-66 (1985).
11. Soulez, M. et al. Growth and differentiation of C2 myogenic cells are dependent on serum response factor. *Mol Cell Biol* 16, 6065-74 (1996).
12. Lu, J., McKinsey, T. A., Zhang, C. L. & Olson, E. N. Regulation of skeletal myogenesis by association of the MEF2 transcription factor with class II histone deacetylases. *Mol Cell* 6, 233-44 (2000).
13. Lee, R. C. & Ambros, V. An extensive class of small RNAs in *Caenorhabditis elegans*. *Science* 294, 862-4 (2001).
14. Lagos-Quintana, M. et al. Identification of tissue-specific microRNAs from mouse. *Curr Biol* 12, 735-9 (2002).
15. Sempere, L. F. et al. Expression profiling of mammalian microRNAs uncovers a subset of brain-expressed microRNAs with possible roles in murine and human neuronal differentiation. *Genome Biol* 5, R13 (2004).
16. Wienholds, E. et al. MicroRNA expression in zebrafish embryonic development. *Science* 309, 310-1 (2005).

17. Mansfield, J. H. et al. MicroRNA-responsive 'sensor' transgenes uncover Hox-like and other developmentally regulated patterns of vertebrate microRNA expression. *Nat Genet* 36, 1079-83 (2004).
18. Hutvagner, G., Simard, M. J., Mello, C. C. & Zamore, P. D. Sequence-specific inhibition of small RNA function. *PLoS Biol* 2, E98 (2004).
19. Meister, G., Landthaler, M., Dorsett, Y. & Tuschl, T. Sequence-specific inhibition of microRNA- and siRNA-induced RNA silencing. *Rna* 10, 544-50 (2004).
20. Lewis, B. P., Shih, I. H., Jones-Rhoades, M. W., Bartel, D. P. & Burge, C. B. Prediction of mammalian microRNA targets. *Cell* 115, 787-98 (2003).
21. Kiriakidou, M. et al. A combined computational-experimental approach predicts human microRNA targets. *Genes Dev* 18, 1165-78 (2004).
22. Krek, A. et al. Combinatorial microRNA target predictions. *Nat Genet* 37, 495-500 (2005).
23. McKinsey, T. A., Zhang, C. L., Lu, J. & Olson, E. N. Signal-dependent nuclear export of a histone deacetylase regulates muscle differentiation. *Nature* 408, 106-11 (2000).
24. Wang, D. et al. Regulation of cardiac growth and development by SRF and its cofactors. *Cold Spring Harb Symp Quant Biol* 67, 97-105 (2002).
25. Li, S. et al. Requirement for serum response factor for skeletal muscle growth and maturation revealed by tissue-specific gene deletion in mice. *Proc Natl Acad Sci USA* 102, 1082-7 (2005).
26. Wang, D. et al. Activation of cardiac gene expression by myocardin, a transcriptional cofactor for serum response factor. *Cell* 105, 851-62 (2001).
27. Cao, D. et al. Modulation of smooth muscle gene expression by association of histone acetyltransferases and deacetylases with myocardin. *Mol Cell Biol* 25, 364-76 (2005).
28. Kroll, K. L. & Amaya, E. Transgenic *Xenopus* embryos from sperm nuclear transplantations reveal FGF signaling requirements during gastrulation. *Development* 122, 3173-83 (1996).
29. Conlon, F. L., Sedgwick, S. G., Weston, K. M. & Smith, J. C. Inhibition of Xbra transcription activation causes defects in mesodermal patterning and reveals autoregulation of Xbra in dorsal mesoderm. *Development* 122, 2427-35 (1996).
30. Brown, D. D. et al. Tbx5 and Tbx20 act synergistically to control vertebrate heart morphogenesis. *Development* 132, 553-63 (2005).
31. Freier et al. (1986) *Proc Natl Aced Sci USA* 83:9373-9377.
32. Turner et al. (1987) *Cold Spring Herb Symp Quant Biol LII*:123-133.
33. Smith & Waterman (1981) *Adv Appl Math* 2:482-489.
34. Needleman & Wunsch (1970) *J Mol Biol* 48:443-453.
35. Pearson & Lipman (1988) *Proc Natl Acad Sci USA* 85:2444-2448.
36. Ausubel et al., eds (1989) *Current Protocols in Molecular Biology*. Wiley, New York, N.Y., United States of America.
37. Altschul et al. (1990) *J Mol Biol* 215:403-410.
38. Henikoff & Henikoff (1992) *Proc Natl Aced Sci USA* 89:10915-10919.
39. Karlin & Altschul (1993) *Proc Natl Acad Sci USA* 90:5873-5877.
40. Sambrook & Russell (2001) *Molecular Cloning: A Laboratory Manual*, 3rd ed. Cold Spring Harbor Laboratory Press, Cold Spring Harbor, N.Y.
41. Agrawal S (ed.) *Methods in Molecular Biology*, volume 20, Humana Press, Totowa, N.J., United States of America.
42. Tijssen (1993) *Laboratory Techniques in Biochemistry and Molecular Biology—Hybridization with Nucleic Acid Probes*. Elsevier, New York, United States of America.
43. Tibanyenda et al. (1984) *Eur J Biochem* 139:19-27.
44. Ebel et al. (1992) *Biochem* 31:12083-12086.
45. Goeddel (1990) Gene Expression Technology. *Methods in Enzymology*, Volume 185, Academic Press, San Diego, Calif., United States of America.
46. Silhavy (1984) *Experiments with Gene Fusions*. Cold Spring Harbor Laboratory, Cold Spring Harbor, N.Y., United States of America.
47. Glover & Hames (1995) *DNA Cloning: A Practical Approach*, 2nd ed. IRL Press at Oxford University Press, Oxford; New York.
48. Adelman et al. (1983) *DNA* 2:183-193.
49. Lee, R. C., Feinbaum, R. L., and Ambros, V. (1993). The *C. elegans* heterochronic gene lin-4 encodes small RNAs with antisense complementarity to lin-14. Cell 75, 843-854.
50. Wightman, B., Ha, I., and Ruvkun, G. (1993). Posttranscriptional regulation of the heterochronic gene lin-14 by lin-4 mediates temporal pattern formation in *C. elegans*. Cell 75, 855-862.
51. Lee, Y., Kim, M., Han, J., Yeom, K. H., Lee, S., Baek, S. H., and Kim, V. N. (2004). MicroRNA genes are transcribed by RNA polymerase II. Embo J 23, 4051-4060.
52. Bracht, J., Hunter, S., Eachus, R., Weeks, P., and Pasquinelli, A. E. (2004). Trans-splicing and polyadenylation of let-7 microRNA primary transcripts. Rna 10, 1586-1594.
53. Rodriguez, A., Griffiths-Jones, S., Ashurst, J. L., and Bradley, A. (2004). Identification of mammalian microRNA host genes and transcription units. Genome Res 14, 1902-1910.
54. Lee, Y., Ahn, C., Han, J., Choi, H., Kim, J., Yim, J., Lee, J., Provost, P., Radmark, O., Kim, S., and Kim, V. N. (2003). The nuclear RNase III Drosha initiates microRNA processing. Nature 425, 415-419.
55. Basyuk, E., Suavet, F., Doglio, A., Bordonne, R., and Bertrand, E. (2003). Human let-7 stem-loop precursors harbor features of RNase III cleavage products. Nucleic Acids Res 31, 6593-6597.
56. Lund, E., Guttinger, S., Calado, A., Dahlberg, J. E., and Kutay, U. (2004). Nuclear export of microRNA precursors. Science 303, 95-98.
57. Yi, R., Qin, Y., Macara, I. G., and Cullen, B. R. (2003). Exportin-5 mediates the nuclear export of pre-microRNAs and short hairpin RNAs. Genes Dev 17, 3011-3016.
58. Yi, R., Doehle, B. P., Qin, Y., Macara, I. G., and Cullen, B. R. (2005). Overexpression of exportin 5 enhances RNA interference mediated by short hairpin RNAs and microRNAs. Rna 11, 220-226.
59. Bohnsack, M. T., Czaplinski, K., and Gorlich, D. (2004). Exportin 5 is a RanGTP-dependent dsRNA-binding protein that mediates nuclear export of pre-miRNAs. Rna 10, 185-191.
60. Gwizdek, C., Ossareh-Nazari, B., Brownawell, A. M., Evers, S., Macara, I. G., and Dargemont, C. (2004). Minihelix-containing RNAs mediate exportin-5-dependent nuclear export of the double-stranded RNA-binding protein ILF3. J Biol Chem 279, 884-891.
61. Grishok, A., Pasquinelli, A. E., Conte, D., Li, N., Parrish, S., Ha, I., Baillie, D. L., Fire, A., Ruvkun, G., and Mello, C. C. (2001). Genes and mechanisms related to RNA interference regulate expression of the small temporal RNAs that control C. elegans developmental timing. Cell 106, 23-34.
62. Hutvagner, G., McLachlan, J., Pasquinelli, A. E., Balint, E., Tuschl, T., and Zamore, P. D. (2001). A cellular function for the RNA-interference enzyme Dicer in the maturation of the let-7 small temporal RNA. Science 293, 834-838.
63. Ketting, R. F., Fischer, S. E., Bernstein, E., Sijen, T., Hannon, G. J., and Plasterk, R. H. (2001). Dicer functions in RNA interference and in synthesis of small RNA involved in developmental timing in C. elegans. Genes Dev 15, 2654-2659.
64. Schwarz, D. S., Hutvagner, G., Du, T., Xu, Z., Aronin, N., and Zamore, P. D. (2003). Asymmetry in the assembly of the RNAi enzyme complex. Cell 115, 199-208.
65. Khvorova, A., Reynolds, A., and Jayasena, S. D. (2003). Functional siRNAs and miRNAs exhibit strand bias. Cell 115, 209-216.
66. Pillai, R. S., Anus, C. G., and Filipowicz, W. (2004). Tethering of human go proteins to mRNA mimics the miRNA-mediated repression of protein synthesis. Rna 10, 1518-1525.
67. Doench, J. G., and Sharp, P. A. (2004). Specificity of microRNA target selection in translational repression. Genes Dev 18, 504-511.
68. Bartel, D. P. (2004). MicroRNAs: genomics, biogenesis, mechanism, and function. Cell 116, 281-297.
69. Bernstein, E., Kim, S. Y., Carmell, M. A., Murchison, E. P., Alcorn, H., Li, M. Z., Mills, A. A., Elledge, S. J., Anderson, K. V., and Hannon, G. J. (2003). Dicer is essential for mouse development. Nat Genet 35, 215-217.
70. Harte, B. D., McManus, M. T., Mansfield, J. H., Hornstein, E., and Tabin, C. J. (2005). The RNaseIII enzyme Dicer is required for morphogenesis but not patterning of the vertebrate limb. Proc Natl Acad Sci USA.
71. Giraldez, A. J., Cinalli, R. M., Glasner, M. E., Enright, A. J., Thomson, J. M., Baskerville, S., Hammond, S. M., Bartel, D. P., and Schier, A. F. (2005). MicroRNAs regulate brain morphogenesis in zebrafish. Science 308, 833-838.
72. Poy, M. N., Eliasson, L., Krutzfeldt, J., Kuwajima, S., Ma, X., Macdonald, P. E., Pfeffer, S., Tuschl, T., Rajewsky, N., Rorsman, P., and Stoffel, M. (2004). A pancreatic islet-specific microRNA regulates insulin secretion. Nature 432, 226-230.
73. Esau, C., Kang, X., Peralta, E., Hanson, E., Marcusson, E. G., Ravichandran, L. V., Sun, Y., Koo, S., Perera, R. J., Jain, R., et al. (2004). MicroRNA-143 regulates adipocyte differentiation. J Biol Chem 279, 52361-52365.
74. He, L., Thomson, J. M., Hemann, M. T., Hernando-Monge, E., Mu, D., Goodson, S., Powers, S., Cordon-Cardo, C., Lowe, S. W., Hannon, G. J., and Hammond, S. M. (2005). A microRNA polycistron as a potential human oncogene. Nature 435, 828-833.
75. Chen, C. Z., Li, L., Lodish, H. F., and Bartel, D. P. (2004). MicroRNAs modulate hematopoietic lineage differentiation. Science 303, 83-86.
76. Johnston, R. J., and Hobert, O. (2003). A microRNA controlling left/right neuronal asymmetry in Caenorhabditis elegans. Nature 426, 845-849.
77. Chang, S., Johnston, R. J., Jr., Frokjaer-Jensen, C., Lockery, S., and Hobert, O. (2004). MicroRNAs act sequentially and asymmetrically to control chemosensory laterality in the nematode. Nature 430, 785-789.
78. Yekta, S., Shih, I. H., and Bartel, D. P. (2004). MicroRNA-directed cleavage of HOXB8 mRNA. Science 304, 594-596.
79. Mansfield, J. H., Harte, B. D., Nissen, R., Obenauer, J., Srineel, J., Chaudhuri, A., Farzan-Kashani, R., Zuker, M., Pasquinelli, A. E., Ruvkun, G., et al. (2004). MicroRNA-responsive 'sensor' transgenes uncover Hox-like and other developmentally regulated patterns of vertebrate microRNA expression. Nat Genet 36, 1079-1083.
80. Zhao, Y., Samal, E., and Srivastava, D. (2005). Serum response factor regulates a muscle-specific microRNA that targets Hand2 during cardiogenesis. Nature 436, 214-220.
81. Lewis, B. P., Shih, I. H., Jones-Rhoades, M. W., Bartel, D. P., and Burge, C. B. (2003). Prediction of mammalian microRNA targets. Cell 115, 787-798.
82. John, B., Enright, A. J., Aravin, A., Tuschl, T., Sander, C., and Marks, D. S. (2004). Human MicroRNA targets. PLoS Biol 2, e363.
83. Kiriakidou, M., Nelson, P. T., Kouranov, A., Fitziev, P., Bouyioukos, C., Mourelatos, Z., and Hatzigeorgiou, A. (2004). A combined computational-experimental approach predicts human microRNA targets. Genes Dev 18, 1165-1178.
84. Krek, A., Grun, D., Poy, M. N., Wolf, R., Rosenberg, L., Epstein, E. J., MacMenamin, P., da Piedade, I., Gunsalus, K. C., Stoffel, M., and Rajewsky, N. (2005). Combinatorial microRNA target predictions. Nat Genet 37, 495-500.
85. Rajewsky, N., and Socci, N. D. (2004). Computational identification of microRNA targets. Dev Biol 267, 529-535.
86. Nicol, R. L., Frey, N., Pearson, G., Cobb, M., Richardson, J., and Olson, E. N. (2001). Activated MEK5 induces serial assembly of sarcomeres and eccentric cardiac hypertrophy. Embo J 20, 2757-2767.
87. Jones, W. K., Grupp, I. L., Doetschman, T., Grupp, G., Osinska, H., Hewett, T. E., Boivin, G., Gulick, J., Ng, W. A., and Robbins, J. (1996). Ablation of the murine alpha myosin heavy chain gene leads to dosage effects and functional deficits in the heart. J Clin Invest 98, 1906-1917.
88. Liu, P., Jenkins, N. A., and Copeland, N. G. (2003). A highly efficient recombineering-based method for generating conditional knockout mutations. Genome Res 13, 476-484.
89. Cotta-de-Almeida, V., Schonhoff, S., Shibata, T., Leiter, A., and Snapper, S. B. (2003). A new method for rapidly generating gene-targeting vectors by engineering BACs through homologous recombination in bacteria. Genome Res 13, 2190-2194.
90. Subramaniam, A., Jones, W. K., Gulick, J., Wert, S., Neumann, J., and Robbins, J. (1991). Tissue-specific regulation of the alpha-myosin heavy chain gene promoter in transgenic mice. J Biol Chem 266, 24613-24620.
91. Sanbe, A., Gulick, J., Hanks, M. C., Liang, Q., Osinska, H., and Robbins, J. (2003). Reengineering inducible cardiac-specific transgenesis with an attenuated myosin heavy chain promoter. Circ Res 92, 609-616.
92. Czubryt, M. P., McAnally, J., Fishman, G. I., and Olson, E. N. (2003). Regulation of peroxisome proliferator-activated receptor gamma coactivator 1 alpha (PGC-1 alpha) and mitochondrial function by MEF2 and HDAC5. Proc Natl Acad Sci USA 100, 1711-1716.
93. Ito, M., Yuan, C. X., Malik, S., Gu, W., Fondell, J. D., Yamamura, S., Fu, Z. Y., Zhang, X., Qin, J., and Roeder, R. G. (1999). Identity between TRAP and SMCC complexes indicates novel pathways for the function of nuclear receptors and diverse mammalian activators. Mol Cell 3, 361-370.

94. Fondell, J. D., Ge, H., and Roeder, R. G. (1996). Ligand induction of a transcriptionally active thyroid hormone receptor coactivator complex. Proc Natl Acad Sci USA 93, 8329-8333.

95. Treisman, J. (2001). *Drosophila* homologues of the transcriptional coactivation complex subunits TRAP240 and TRAP230 are required for identical processes in eye-antennal disc development. Development 128, 603-615.

96. Ito, M., Yuan, C. X., Okano, H. J., Darnell, R. B., and Roeder, R. G. (2000). Involvement of the TRAP220 component of the TRAP/SMCC coactivator complex in embryonic development and thyroid hormone action. Mol Cell 5, 683-693.

97. Muncke, N., Jung, C., Rudiger, H., Ulmer, H., Roeth, R., Hubert, A., Goldmuntz, E., Driscoll, D., Goodship, J., Schon, K., and Rappold, G. (2003). Missense mutations and gene interruption in PROSIT240, a novel TRAP240-like gene, in patients with congenital heart defect (transposition of the great arteries). Circulation 108, 2843-2850.

98. Lompre, A. M., Nadal-Ginard, B., and Mandavi, V. (1984). Expression of the cardiac ventricular alpha- and beta-myosin heavy chain genes is developmentally and hormonally regulated. J Biol Chem 259, 6437-6446.

99. Everett, A. W., Sinha, A. M., Umeda, P. K., Jakovcic, S., Rabinowitz, M., and Zak, R. (1984). Regulation of myosin synthesis by thyroid hormone: relative change in the alpha- and beta-myosin heavy chain mRNA levels in rabbit heart. Biochemistry 23, 1596-1599.

100. Darling, D. S., Carter, R. L., Yen, P. M., Welborn, J. M., Chin, W. W., and Umeda, P. K. (1993). Different dimerization activities of alpha and beta thyroid hormone receptor isoforms. J Biol Chem 268, 10221-10227.

101. Subramaniam, A., Gulick, J., Neumann, J., Knotts, S., and Robbins, J. (1993). Transgenic analysis of the thyroid-responsive elements in the alpha-cardiac myosin heavy chain gene promoter. J Biol Chem 268, 4331-4336.

102. Gustafson, T. A., Markham, B. E., Bahl, J. J., and Morkin, E. (1987). Thyroid hormone regulates expression of a transfected alpha-myosin heavy-chain fusion gene in fetal heart cells. Proc Natl Acad Sci USA 84, 3122-3126.

103. Santalucia, T., Boheler, K. R., Brand, N. J., Sahye, U., Fandos, C., Vinals, F., Ferre, J., Testar, X., Palacin, M., and Zorzano, A. (1999). Factors involved in GLUT-1 glucose transporter gene transcription in cardiac muscle. J Biol Chem 274, 17626-17634.

104. Hagen, G., Muller, S., Beato, M., and Suske, G. (1994). Sp1-mediated transcriptional activation is repressed by Sp3. Embo J 13, 3843-3851.

105. Hagen, G., Muller, S., Beato, M., and Suske, G. (1992). Cloning by recognition site screening of two novel GT box binding proteins: a family of Sp1 related genes. Nucleic Acids Res 20, 5519-5525.

106. Schonberger, J., Wang, L., Shin, J. T., Kim, S. D., Depreux, F. F., Zhu, H., Zon, L., Pizard, A., Kim, J. B., Macrae, C. A., et al. (2005). Mutation in the transcriptional coactivator EYA4 causes dilated cardiomyopathy and sensorineural hearing loss. Nat Genet 37, 418-422.

107. Wayne, S., Robertson, N. G., DeClau, F., Chen, N., Verhoeven, K., Prasad, S., Tranebjarg, L., Morton, C. C., Ryan, A. F., Van Camp, G., and Smith, R. J. (2001). Mutations in the transcriptional activator EYA4 cause late-onset deafness at the DFNA10 locus. Hum Mol Genet 10, 195-200.

108. Borsani, G., DeGrandi, A., Ballabio, A., Bulfone, A., Bernard, L., Banfi, S., Gattuso, C., Mariani, M., Dixon, M., Donnai, D., et al. (1999). EYA4, a novel vertebrate gene related to *Drosophila* eyes absent. Hum Mol Genet 8, 11-23.

109. Bonini, N. M., Leiserson, W. M., and Benzer, S. (1993). The eyes absent gene: genetic control of cell survival and differentiation in the developing *Drosophila* eye. Cell 72, 379-395.

110. Heanue, T. A., Reshef, R., Davis, R. J., Mardon, G., Oliver, G., Tomarev, S., Lassar, A. B., and Tabin, C. J. (1999). Synergistic regulation of vertebrate muscle development by Dach2, Eya2, and Six1, homologs of genes required for *Drosophila* eye formation. Genes Dev 13, 3231-3243.

111. Xu, X., Rich, E. S., Jr., and Seldin, D. C. (1998). Murine protein kinase CK2 alpha': cDNA and genomic cloning and chromosomal mapping. Genomics 48, 79-86.

112. Pinna, L. A., and Meggio, F. (1997). Protein kinase CK2 ("casein kinase-2") and its implication in cell division and proliferation. Prog Cell Cycle Res 3, 77-97.

113. Granzier, H. L., and Labeit, S. (2004). The giant protein titin: a major player in myocardial mechanics, signaling, and disease. Circ Res 94, 284-295.

114. Yan et al (2003). J. Biol. Chem. 278(10), 8826-8836.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for treating a muscle injury in a subject comprising administering to a muscle injury site in the subject a combination of miR-133, wherein miR-133 comprises the nucleotide sequence of SEQ ID NO: 2, and an inhibitor of miR-1, wherein the inhibitor is a polynucleotide comprising a nucleotide sequence that is complementary to SEQ ID NO: 1.

2. The method of claim 1, further comprising administering to the muscle injury site at a subsequent time point a combination of miR-1, wherein miR-1 comprises the nucleotide sequence of SEQ ID NO: 1, and an inhibitor of miR-133, wherein the inhibitor is a polynucleotide comprising a nucleotide sequence that is complementary to SEQ ID NO: 2.

3. The method of claim 1, wherein the muscle injury results from a mechanical muscle trauma, a muscular degenerative disorder, a cardiac insult, or a combination thereof.

4. The method of claim 1, wherein the subject is a mammal.

5. The method of claim 1, wherein the inhibitor of miR-1 is a modified polynucleotide.

6. The method of claim 5, wherein the modified polynucleotide is a 2'-O-methyl polynucleotide.

7. The method of claim 6, wherein the inhibitor of miR-1 is 2'-O-methyl-miR-1 (SEQ ID NO: 62).

8. The method of claim 2, wherein the inhibitor of miR-133 is a modified polynucleotide.

9. The method of claim 8, wherein the modified polynucleotide is a 2'-O-methyl polynucleotide.

10. The method of claim 9, wherein the inhibitor of miR-133 is 2'-O-methyl-miR-133 (SEQ ID NO: 63).

11. The method of claim 1, wherein miR-133 is encoded by a vector.

12. The method of claim 11, wherein the vector comprises:
(a) a promoter operatively linked to a nucleic acid molecule encoding miR-133; and
(b) a transcription termination sequence.

13. A method for treating a muscle injury in a subject comprising administering to a muscle injury site in the subject a combination of miR-1, wherein miR-1 comprises the nucleotide sequence of SEQ ID NO: 1, and an inhibitor of miR-133, wherein the inhibitor is a polynucleotide comprising a nucleotide sequence that is complementary to SEQ ID NO: 2.

14. The method of claim 13, wherein the subject is a mammal.

15. An in vitro method for inducing myocyte differentiation comprising contacting a myocyte with miR-1, wherein miR-1 comprises the nucleotide sequence of SEQ ID NO: 1, and an inhibitor of miR-133, wherein the inhibitor is a polynucleotide comprising a nucleotide sequence that is complementary to SEQ ID NO: 2, wherein differentiation of the myocyte is induced.

16. The method of claim 15, wherein miR-1 is encoded by a vector.

17. An in vitro method for promoting myocyte proliferation comprising contacting a myocyte with miR-133, wherein miR-133 comprises the nucleotide sequence of SEQ ID NO: 2 and an inhibitor of miR-1, wherein the inhibitor is a polynucleotide comprising nucleotide sequence that is complementary to SEQ ID NO: 1, wherein proliferation of the myocyte is promoted.

18. The method of claim 17, wherein miR-133 is encoded by a vector.

19. The method of claim 2, wherein miR-1 is encoded by a vector.

20. The method of claim 19, wherein the vector comprises:
(a) a promoter operatively linked to a nucleic acid molecule encoding miR-1; and
(b) a transcription termination sequence.

* * * * *

UNITED STATES PATENT AND TRADEMARK OFFICE
CERTIFICATE OF CORRECTION

PATENT NO. : 8,431,542 B2
APPLICATION NO. : 12/086109
DATED : April 30, 2013
INVENTOR(S) : Wang et al.

It is certified that error appears in the above-identified patent and that said Letters Patent is hereby corrected as shown below:

On title page, item 73 Assignee
        replace "Durham, NC"
        with --Chapel Hill, NC--.

Signed and Sealed this
Second Day of July, 2013

Teresa Stanek Rea
*Acting Director of the United States Patent and Trademark Office*

SEQUENCE LISTING

<160> NUMBER OF SEQ ID NOS: 82

<210> SEQ ID NO 1
<211> LENGTH: 21
<212> TYPE: RNA
<213> ORGANISM: Artificial sequence
<220> FEATURE:
<223> OTHER INFORMATION: Artificially synthesized miRNA

<400> SEQUENCE: 1
uggaauguaa agaaguaugu a                                              21

<210> SEQ ID NO 2
<211> LENGTH: 22
<212> TYPE: RNA
<213> ORGANISM: Artificial sequence

```
<220> FEATURE:
<223> OTHER INFORMATION: Artificially synthesized miRNA

<400> SEQUENCE: 2
uugguccccu ucaaccagcu gu                                                    22

<210> SEQ ID NO 3
<211> LENGTH: 22
<212> TYPE: RNA
<213> ORGANISM: Artificial sequence
<220> FEATURE:
<223> OTHER INFORMATION: Artificially synthesized miRNA

<400> SEQUENCE: 3
uggaauguaa ggaagugugu gg                                                    22

<210> SEQ ID NO 4
<211> LENGTH: 22
<212> TYPE: RNA
<213> ORGANISM: Artificial sequence
<220> FEATURE:
<223> OTHER INFORMATION: Artificially synthesized miRNA

<400> SEQUENCE: 4
auaagacgag caaaaagcuu gu                                                    22

<210> SEQ ID NO 5
<211> LENGTH: 22
<212> TYPE: RNA
<213> ORGANISM: Artificial sequence
<220> FEATURE:
<223> OTHER INFORMATION: Artificially synthesized miRNA

<400> SEQUENCE: 5
aagcugccag uugaagaacu gu                                                    22

<210> SEQ ID NO 6
<211> LENGTH: 22
<212> TYPE: RNA
<213> ORGANISM: Artificial sequence
<220> FEATURE:
<223> OTHER INFORMATION: Artificially synthesized miRNA
<220> FEATURE:
<221> NAME/KEY: misc_feature
<222> LOCATION: (11)..(11)
<223> OTHER INFORMATION: y can be C or U
<220> FEATURE:
<221> NAME/KEY: misc_feature
<222> LOCATION: (21)..(21)
<223> OTHER INFORMATION: y can be C or U

<400> SEQUENCE: 6
uucaaguaau ycaggauagg yu                                                    22

<210> SEQ ID NO 7
<211> LENGTH: 23
<212> TYPE: RNA
<213> ORGANISM: Artificial sequence
<220> FEATURE:
<223> OTHER INFORMATION: Artificially synthesized miRNA
<220> FEATURE:
<221> NAME/KEY: misc_feature
<222> LOCATION: (10)..(10)
<223> OTHER INFORMATION: y can be C or U
<220> FEATURE:
<221> NAME/KEY: misc_feature
<222> LOCATION: (18)..(18)
<223> OTHER INFORMATION: r can be G or A
<220> FEATURE:
<221> NAME/KEY: misc_feature
```

<222> LOCATION: (21)..(21)
<223> OTHER INFORMATION: k can be G or U

<400> SEQUENCE: 7
uagcaccauy ugaaaucrgu kuu 23

<210> SEQ ID NO 8
<211> LENGTH: 23
<212> TYPE: RNA
<213> ORGANISM: Artificial sequence
<220> FEATURE:
<223> OTHER INFORMATION: Artificially synthesized miRNA
<220> FEATURE:
<221> NAME/KEY: misc_feature
<222> LOCATION: (1)..(22)
<223> OTHER INFORMATION: y can be C or U; k can be G or U; w can be U or A; m can be C or A; s can be G or C; h can be A, C, or U; v can be G, A, or C; n can be A, G, C, or U; b can be C, G, or U

<400> SEQUENCE: 8
ykuwmaswys shhswyuvnv vbc 23

<210> SEQ ID NO 9
<211> LENGTH: 22
<212> TYPE: RNA
<213> ORGANISM: Artificial sequence
<220> FEATURE:
<223> OTHER INFORMATION: Artificially synthesized miRNA
<220> FEATURE:
<221> NAME/KEY: misc_feature
<222> LOCATION: (22)..(22)
<223> OTHER INFORMATION: y can be C or U

<400> SEQUENCE: 9
ucacagugaa ccggucucuu uy 22

<210> SEQ ID NO 10
<211> LENGTH: 22
<212> TYPE: RNA
<213> ORGANISM: Artificial sequence
<220> FEATURE:
<223> OTHER INFORMATION: Artificially synthesized miRNA

<400> SEQUENCE: 10
ugagaugaag cacuguagcu ca 22

<210> SEQ ID NO 11
<211> LENGTH: 24
<212> TYPE: RNA
<213> ORGANISM: Artificial sequence
<220> FEATURE:
<223> OTHER INFORMATION: Artificially synthesized miRNA

<400> SEQUENCE: 11
guccaguuuu cccaggaauc ccuu 24

<210> SEQ ID NO 12
<211> LENGTH: 21
<212> TYPE: RNA
<213> ORGANISM: Artificial sequence
<220> FEATURE:
<223> OTHER INFORMATION: Artificially synthesized miRNA

<400> SEQUENCE: 12
uucaaguaau ccaggauagg c 21

<210> SEQ ID NO 13
<211> LENGTH: 22

```
<212> TYPE: RNA
<213> ORGANISM: Artificial sequence
<220> FEATURE:
<223> OTHER INFORMATION: Artificially synthesized miRNA

<400> SEQUENCE: 13
uucaaguaau ucaggauagg uu                                               22

<210> SEQ ID NO 14
<211> LENGTH: 21
<212> TYPE: RNA
<213> ORGANISM: Artificial sequence
<220> FEATURE:
<223> OTHER INFORMATION: Artificially synthesized miRNA

<400> SEQUENCE: 14
uagcaccauc ugaaaucggu u                                                21

<210> SEQ ID NO 15
<211> LENGTH: 23
<212> TYPE: RNA
<213> ORGANISM: Artificial sequence
<220> FEATURE:
<223> OTHER INFORMATION: Artificially synthesized miRNA

<400> SEQUENCE: 15
uagcaccauu ugaaaucagu guu                                              23

<210> SEQ ID NO 16
<211> LENGTH: 20
<212> TYPE: RNA
<213> ORGANISM: Artificial sequence
<220> FEATURE:
<223> OTHER INFORMATION: Artificially synthesized miRNA

<400> SEQUENCE: 16
uagcaccauu ugaaaucggu                                                  20

<210> SEQ ID NO 17
<211> LENGTH: 22
<212> TYPE: RNA
<213> ORGANISM: Artificial sequence
<220> FEATURE:
<223> OTHER INFORMATION: Artificially synthesized miRNA

<400> SEQUENCE: 17
cuuucagucg gauguuugca gc                                               22

<210> SEQ ID NO 18
<211> LENGTH: 22
<212> TYPE: RNA
<213> ORGANISM: Artificial sequence
<220> FEATURE:
<223> OTHER INFORMATION: Artificially synthesized miRNA

<400> SEQUENCE: 18
uguaaacauc cuacacucag cu                                               22

<210> SEQ ID NO 19
<211> LENGTH: 23
<212> TYPE: RNA
<213> ORGANISM: Artificial sequence
<220> FEATURE:
<223> OTHER INFORMATION: Artificially synthesized miRNA

<400> SEQUENCE: 19
uguaaacauc cuacacucuc agc                                              23
```

-continued

<210> SEQ ID NO 20
<211> LENGTH: 22
<212> TYPE: RNA
<213> ORGANISM: Artificial sequence
<220> FEATURE:
<223> OTHER INFORMATION: Artificially synthesized miRNA

<400> SEQUENCE: 20
uguaaacauc cccgacugga ag                                                22

<210> SEQ ID NO 21
<211> LENGTH: 21
<212> TYPE: RNA
<213> ORGANISM: Artificial sequence
<220> FEATURE:
<223> OTHER INFORMATION: Artificially synthesized miRNA

<400> SEQUENCE: 21
cuuucagucg gauguuuaca g                                                 21

<210> SEQ ID NO 22
<211> LENGTH: 22
<212> TYPE: RNA
<213> ORGANISM: Artificial sequence
<220> FEATURE:
<223> OTHER INFORMATION: Artificially synthesized miRNA

<400> SEQUENCE: 22
ucacagugaa ccggucucuu uu                                                22

<210> SEQ ID NO 23
<211> LENGTH: 22
<212> TYPE: RNA
<213> ORGANISM: Artificial sequence
<220> FEATURE:
<223> OTHER INFORMATION: Artificially synthesized miRNA

<400> SEQUENCE: 23
ucacagugaa ccggucucuu uc                                                22

<210> SEQ ID NO 24
<211> LENGTH: 63
<212> TYPE: DNA
<213> ORGANISM: Homo sapiens

<400> SEQUENCE: 24
tttttctttt tgatcagaac attccttctt tactggtcac agccacgtgc tcattccatt       60
ctt                                                                     63

<210> SEQ ID NO 25
<211> LENGTH: 63
<212> TYPE: DNA
<213> ORGANISM: Pan troglodytes

<400> SEQUENCE: 25
tttttctttt tgatcagaac attccttctt tactggtcac agccacgtgc tcattccatt       60
ctt                                                                     63

<210> SEQ ID NO 26
<211> LENGTH: 61
<212> TYPE: DNA
<213> ORGANISM: Mus musculus

<400> SEQUENCE: 26

```
tgtttctttc ctcagaacat tccttcttca ctggtcacag ccacgtgctc attccatcct    60
t                                                                   61

<210> SEQ ID NO 27
<211> LENGTH: 65
<212> TYPE: DNA
<213> ORGANISM: Rattus rattus

<400> SEQUENCE: 27
tgtttctttc ctcagaacat tccttccttc ttcactggtc ccagccacgt gctcattcca    60
tcctt                                                               65

<210> SEQ ID NO 28
<211> LENGTH: 61
<212> TYPE: DNA
<213> ORGANISM: Canis familiaris

<400> SEQUENCE: 28
gttttacttt tcgatcagaa cattccttct ttactggtca cagccatgtg ctcattccat    60
t                                                                   61

<210> SEQ ID NO 29
<211> LENGTH: 64
<212> TYPE: DNA
<213> ORGANISM: Gallus gallus

<400> SEQUENCE: 29
tttttacttt cgatacggaa cattcctttt ttattagtct cagtcatgta ttcattccat    60
tctt                                                                64

<210> SEQ ID NO 30
<211> LENGTH: 23
<212> TYPE: DNA
<213> ORGANISM: Homo sapiens

<400> SEQUENCE: 30
gctcctgggt tggagggaac cac                                           23

<210> SEQ ID NO 31
<211> LENGTH: 22
<212> TYPE: DNA
<213> ORGANISM: Homo sapiens

<400> SEQUENCE: 31
ttagcttacc caatgggacc gt                                            22

<210> SEQ ID NO 32
<211> LENGTH: 26
<212> TYPE: DNA
<213> ORGANISM: Rattus rattus

<400> SEQUENCE: 32
ggggctcttg ggttgaaggg aaccac                                        26

<210> SEQ ID NO 33
<211> LENGTH: 22
<212> TYPE: DNA
<213> ORGANISM: Rattus rattus

<400> SEQUENCE: 33
ttagcttacc caatgggacc gt                                            22
```

```
<210> SEQ ID NO 34
<211> LENGTH: 83
<212> TYPE: RNA
<213> ORGANISM: Mus musculus

<400> SEQUENCE: 34
uuccuuugac gggugagcuu uuggcccggg uuauaccuga cacucacgua uaagacgagc    60
aaaaagcuug uuggucagag gag                                          83

<210> SEQ ID NO 35
<211> LENGTH: 83
<212> TYPE: RNA
<213> ORGANISM: Mus musculus

<400> SEQUENCE: 35
uuccuuugac gggugagcuu uuggcccggg uuauaccuga cacucacgua uaagacgagc    60
aaaaagcuug uuggucagag gag                                          83

<210> SEQ ID NO 36
<211> LENGTH: 83
<212> TYPE: RNA
<213> ORGANISM: Rattus rattus

<400> SEQUENCE: 36
uuccuuugac gggugagcuu uuggcccggg uuauaccuga cucucacgua uaagacgagc    60
aaaaagcuug uuggucagag gag                                          83

<210> SEQ ID NO 37
<211> LENGTH: 71
<212> TYPE: RNA
<213> ORGANISM: Homo sapiens

<400> SEQUENCE: 37
ugacgggcga gcuuuuggcc cgguuauac cugaugcuca cguauaagac gagcaaaaag    60
cuuguugguc a                                                       71

<210> SEQ ID NO 38
<211> LENGTH: 24
<212> TYPE: RNA
<213> ORGANISM: Homo sapiens

<400> SEQUENCE: 38
cuaaaauaua uguaaucguc uuaa                                         24

<210> SEQ ID NO 39
<211> LENGTH: 24
<212> TYPE: RNA
<213> ORGANISM: Mus musculus

<400> SEQUENCE: 39
cuaaaauaua uguaaucguc uuaa                                         24

<210> SEQ ID NO 40
<211> LENGTH: 32
<212> TYPE: DNA
<213> ORGANISM: Mus musculus

<400> SEQUENCE: 40
accaaatgca tcctcctcca cattccttgc tc                                32
```

<210> SEQ ID NO 41
<211> LENGTH: 31
<212> TYPE: DNA
<213> ORGANISM: Mus musculus

<400> SEQUENCE: 41
gtcccagcca agggagcaac attccaacgc t					31

<210> SEQ ID NO 42
<211> LENGTH: 21
<212> TYPE: DNA
<213> ORGANISM: Artificial sequence
<220> FEATURE:
<223> OTHER INFORMATION: Artificially synthesized miR-1 probe

<400> SEQUENCE: 42
tacatacttc tttacattcc a					21

<210> SEQ ID NO 43
<211> LENGTH: 22
<212> TYPE: DNA
<213> ORGANISM: Artificial sequence
<220> FEATURE:
<223> OTHER INFORMATION: Artificially synthesized miR-133 probe

<400> SEQUENCE: 43
acagctggtt gaaggggacc aa					22

<210> SEQ ID NO 44
<211> LENGTH: 20
<212> TYPE: DNA
<213> ORGANISM: Artificial sequence
<220> FEATURE:
<223> OTHER INFORMATION: Artificially synthesized miR-133a-1-up
      regulation probe

<400> SEQUENCE: 44
catgtgaccc ctcacacaca					20

<210> SEQ ID NO 45
<211> LENGTH: 20
<212> TYPE: DNA
<213> ORGANISM: Artificial
<220> FEATURE:
<223> OTHER INFORMATION: Artificially synthesized miR-133a-1-down
      regulation probe

<400> SEQUENCE: 45
acaaggggag cctggatccc					20

<210> SEQ ID NO 46
<211> LENGTH: 22
<212> TYPE: DNA
<213> ORGANISM: Artificial sequence
<220> FEATURE:
<223> OTHER INFORMATION: Artificially synthesized miR-133a-2-up probe

<400> SEQUENCE: 46
ggacatatgc ctaaacacgt ga					22

<210> SEQ ID NO 47
<211> LENGTH: 20
<212> TYPE: DNA
<213> ORGANISM: Artificial sequence
<220> FEATURE:
<223> OTHER INFORMATION: Artificially synthesized miR-133a-2-down  probe

<400> SEQUENCE: 47

```
gaaacatctt tatccagttt                                              20
```

<210> SEQ ID NO 48
<211> LENGTH: 22
<212> TYPE: DNA
<213> ORGANISM: Artificial sequence
<220> FEATURE:
<223> OTHER INFORMATION: Artificially synthesized miR-1-2-up probe

<400> SEQUENCE: 48

```
agactgagac acaggcgaca cc                                           22
```

<210> SEQ ID NO 49
<211> LENGTH: 22
<212> TYPE: DNA
<213> ORGANISM: Artificial sequence
<220> FEATURE:
<223> OTHER INFORMATION: Artificially synthesized miR-1-2-down probe

<400> SEQUENCE: 49

```
tgccggtcca tcggtccatt gc                                           22
```

<210> SEQ ID NO 50
<211> LENGTH: 20
<212> TYPE: DNA
<213> ORGANISM: Artificial sequence
<220> FEATURE:
<223> OTHER INFORMATION: Artificially synthesized miR-1-1-up probe

<400> SEQUENCE: 50

```
cactggatcc attactcttc                                              20
```

<210> SEQ ID NO 51
<211> LENGTH: 20
<212> TYPE: DNA
<213> ORGANISM: Artificial sequence
<220> FEATURE:
<223> OTHER INFORMATION: Artificially synthesized miR-1-1-down probe

<400> SEQUENCE: 51

```
ttggaatggg gctgttagta                                              20
```

<210> SEQ ID NO 52
<211> LENGTH: 43
<212> TYPE: DNA
<213> ORGANISM: Artificial sequence
<220> FEATURE:
<223> OTHER INFORMATION: Artificially synthesized miR-1mut-up probe

<400> SEQUENCE: 52

```
tgaacattca gtgctataaa gaagtatgta ttttgggtag gta                    43
```

<210> SEQ ID NO 53
<211> LENGTH: 43
<212> TYPE: DNA
<213> ORGANISM: Artificial sequence
<220> FEATURE:
<223> OTHER INFORMATION: Artificially synthesized miR-1mut-down probe

<400> SEQUENCE: 53

```
tacctaccca aaatacatac ttctttatag cactgaatgt tca                    43
```

<210> SEQ ID NO 54
<211> LENGTH: 48
<212> TYPE: DNA
<213> ORGANISM: Artificial sequence

```
<220> FEATURE:
<223> OTHER INFORMATION: Artificially synthesized miR-133mut-up probe

<400> SEQUENCE: 54
aatcgcctct tcaatggatt tgtcaaccag ctgtagctat gcattgat          48

<210> SEQ ID NO 55
<211> LENGTH: 48
<212> TYPE: DNA
<213> ORGANISM: Artificial sequence
<220> FEATURE:
<223> OTHER INFORMATION: Artificially synthesized miR-133mut-down probe

<400> SEQUENCE: 55
atcaatgcat agctacagct ggttgacaaa tccattgaag aggcgatt          48

<210> SEQ ID NO 56
<211> LENGTH: 42
<212> TYPE: RNA
<213> ORGANISM: Artificial sequence
<220> FEATURE:
<223> OTHER INFORMATION: Artificially synthesized miR-1 duplex

<400> SEQUENCE: 56
uggaauguaa agaaguaugu acauacuucu uuacauucca ua               42

<210> SEQ ID NO 57
<211> LENGTH: 42
<212> TYPE: RNA
<213> ORGANISM: Artificial sequence
<220> FEATURE:
<223> OTHER INFORMATION: Artificially synthesized miR-1-mut duplex

<400> SEQUENCE: 57
uuaaccauaa agaaguaugu acauacuucu uuauggmuaa ua               42

<210> SEQ ID NO 58
<211> LENGTH: 44
<212> TYPE: RNA
<213> ORGANISM: Artificial sequence
<220> FEATURE:
<223> OTHER INFORMATION: Artificially synthesized miR-133 duplex

<400> SEQUENCE: 58
uugguccccu ucaaccagcu guagcugguu gaaggggacc aaau             44

<210> SEQ ID NO 59
<211> LENGTH: 44
<212> TYPE: RNA
<213> ORGANISM: Artificial sequence
<220> FEATURE:
<223> OTHER INFORMATION: Artificially synthesized miR-133-mut duplex

<400> SEQUENCE: 59
ucaaguaacu ucaaccagcu guagcugguu gaaguuacuu gaau             44

<210> SEQ ID NO 60
<211> LENGTH: 44
<212> TYPE: RNA
<213> ORGANISM: Artificial sequence
<220> FEATURE:
<223> OTHER INFORMATION: Artificially synthesized miR-208 duplex

<400> SEQUENCE: 60
auaagacgag caaaaagcuu guaagcuuuu ugcucgucuu auac             44
```

```
<210> SEQ ID NO 61
<211> LENGTH: 44
<212> TYPE: RNA
<213> ORGANISM: Artificial sequence
<220> FEATURE:
<223> OTHER INFORMATION: Artificially synthesized GFP duplex

<400> SEQUENCE: 61
aacuucaggg ucagcuugcc uuggcaagcu gacccugaag uugg                44

<210> SEQ ID NO 62
<211> LENGTH: 28
<212> TYPE: RNA
<213> ORGANISM: Artificial sequence
<220> FEATURE:
<223> OTHER INFORMATION: Artificially synthesized 2'-O-methyl-miR-1

<400> SEQUENCE: 62
aaauacauac uucuuuacau uccauagc                                  28

<210> SEQ ID NO 63
<211> LENGTH: 31
<212> TYPE: RNA
<213> ORGANISM: Artificial sequence
<220> FEATURE:
<223> OTHER INFORMATION: Artificially synthesized 2'-O-methyl-miR-133

<400> SEQUENCE: 63
agcuacagcu gguugaaggg gaccaaaucc a                              31

<210> SEQ ID NO 64
<211> LENGTH: 32
<212> TYPE: RNA
<213> ORGANISM: Artificial sequence
<220> FEATURE:
<223> OTHER INFORMATION: Artificially synthesized 2'-O-methyl-miR-208

<400> SEQUENCE: 64
gaccaacaag cuuuuugcuc gucuuauacg ug                             32

<210> SEQ ID NO 65
<211> LENGTH: 22
<212> TYPE: RNA
<213> ORGANISM: Artificial sequence
<220> FEATURE:
<223> OTHER INFORMATION: Artificially synthesized 2'-O-methyl-GFP

<400> SEQUENCE: 65
aaggcaagcu gacccugaag uu                                        22

<210> SEQ ID NO 66
<211> LENGTH: 21
<212> TYPE: DNA
<213> ORGANISM: Artificial sequence
<220> FEATURE:
<223> OTHER INFORMATION: Artificially synthesized HDAC4-UTR-up

<400> SEQUENCE: 66
cagcactggt gatagacttg g                                         21

<210> SEQ ID NO 67
<211> LENGTH: 23
<212> TYPE: DNA
<213> ORGANISM: Artificial sequence
<220> FEATURE:
<223> OTHER INFORMATION: Artificially synthesized HDAC4-UTR-down

<400> SEQUENCE: 67
```

```
cttaagaata agttcaataa gac                                         23
```

<210> SEQ ID NO 68
<211> LENGTH: 20
<212> TYPE: DNA
<213> ORGANISM: Artificial sequence
<220> FEATURE:
<223> OTHER INFORMATION: Artificiallly synthesized SRF-UTR-up

<400> SEQUENCE: 68

```
agatatgggg gcttgtgccc                                             20
```

<210> SEQ ID NO 69
<211> LENGTH: 20
<212> TYPE: DNA
<213> ORGANISM: Artificial sequence
<220> FEATURE:
<223> OTHER INFORMATION: Artificially synthesized SRF-UTR-down

<400> SEQUENCE: 69

```
ctgggagaaa gggggtagac                                             20
```

<210> SEQ ID NO 70
<211> LENGTH: 21
<212> TYPE: DNA
<213> ORGANISM: Artificial sequence
<220> FEATURE:
<223> OTHER INFORMATION: Artificially synthesized Myogenin F PCR primer

<400> SEQUENCE: 70

```
tggagctgta tgagacatcc c                                           21
```

<210> SEQ ID NO 71
<211> LENGTH: 21
<212> TYPE: DNA
<213> ORGANISM: Artificial sequence
<220> FEATURE:
<223> OTHER INFORMATION: Artificially synthesized Myogenin R PCR primer

<400> SEQUENCE: 71

```
tggacaatgc tcagggtcc c                                            21
```

<210> SEQ ID NO 72
<211> LENGTH: 20
<212> TYPE: DNA
<213> ORGANISM: Artificial sequence
<220> FEATURE:
<223> OTHER INFORMATION: Artificially synthesized MyoD F PCR primer

<400> SEQUENCE: 72

```
gcaggctctg ctgcgcgacc                                             20
```

<210> SEQ ID NO 73
<211> LENGTH: 23
<212> TYPE: DNA
<213> ORGANISM: Artificial sequence
<220> FEATURE:
<223> OTHER INFORMATION: Artificially synthesized MyoD R PCR primer

<400> SEQUENCE: 73

```
tgcagtcgat ctctcaaagc acc                                         23
```

<210> SEQ ID NO 74
<211> LENGTH: 19
<212> TYPE: DNA
<213> ORGANISM: Artificial sequence

```
<220> FEATURE:
<223> OTHER INFORMATION: Artificially synthesized Skeletal  -actin F
      PCR primer

<400> SEQUENCE: 74
cagagcaagc gaggtatcc                                                19

<210> SEQ ID NO 75
<211> LENGTH: 19
<212> TYPE: DNA
<213> ORGANISM: Artificial sequence
<220> FEATURE:
<223> OTHER INFORMATION: Artificially synthesized Skeletal  -actin R
      PCR primer

<400> SEQUENCE: 75
gtccccagaa tccaacacg                                                19

<210> SEQ ID NO 76
<211> LENGTH: 21
<212> TYPE: DNA
<213> ORGANISM: Artificial sequence
<220> FEATURE:
<223> OTHER INFORMATION: Artificially synthesized MEF2D F PCR primer

<400> SEQUENCE: 76
caagctgttc cagtatgcca g                                             21

<210> SEQ ID NO 77
<211> LENGTH: 20
<212> TYPE: DNA
<213> ORGANISM: Artificial sequence
<220> FEATURE:
<223> OTHER INFORMATION: Artificially synthesized MEF2D R PCR primer

<400> SEQUENCE: 77
aagggatgat gtcaccaggg                                               20

<210> SEQ ID NO 78
<211> LENGTH: 30
<212> TYPE: DNA
<213> ORGANISM: Artificial sequence
<220> FEATURE:
<223> OTHER INFORMATION: Artificially synthesized HDAC4 F PCR primer

<400> SEQUENCE: 78
gagagaattc tgctagcaat gagctcccaa                                    30

<210> SEQ ID NO 79
<211> LENGTH: 34
<212> TYPE: DNA
<213> ORGANISM: Artificial sequence
<220> FEATURE:
<223> OTHER INFORMATION: Artificially synthesized HDAC4 R PCR primer

<400> SEQUENCE: 79
gagactcgag ctatgcaggt tccaagggca gtga                               34

<210> SEQ ID NO 80
<211> LENGTH: 21
<212> TYPE: DNA
<213> ORGANISM: Artificial sequence
<220> FEATURE:
<223> OTHER INFORMATION: Artificially synthesized SRF F PCR primer

<400> SEQUENCE: 80
gtccccatgc agtgatgtat g                                             21
```

<210> SEQ ID NO 81
<211> LENGTH: 20
<212> TYPE: DNA
<213> ORGANISM: Artificial sequence
<220> FEATURE:
<223> OTHER INFORMATION: Artificially synthesized SRF R PCR primer

<400> SEQUENCE: 81
gtagctcggt gaggttgctg                                                 20

<210> SEQ ID NO 82
<211> LENGTH: 2620
<212> TYPE: DNA
<213> ORGANISM: Mus musculus

<400> SEQUENCE: 82
gagcaagttt cactagggcc acacagtatc attgagcact gagcgtggaa ggagacagat      60
gggccacgtt tctcctccct ctttctagcc ttccttctcc ctcccttttc ttatacatta     120
tatcctggcg gcagttttcc ctccctccac tcctcccagt tccttcccca cttccattct     180
cccccagatc cattcctctt atgcccccc ccccaagag caggctttcc atgaataccc      240
accaaacatg gcataacaag ttacaataag atcaggaaca aaccctcata tcaaggctgg     300
atgaggcaac ccaacaggag gaaaagggcc ccaagagcag gcaaaaaact cccactgttg     360
tgtcttctgc tagaacacaa agctacacaa ctataatgta tatgcagagg acccagctca     420
gtctcatcag ggtccgtgtt tgttgctaca gtttctgtga acctctgtgg gctctgctta     480
gttggttctg tgggttgtgt tcttgtggca tcctcaactc ctctggctcc tacaatcttt     540
cctcccatct tctttggagt tcccctggcc atgcctgatg tttggttggc ttggctgtgt     600
gggcctctgc atttatttcc gtcagttgct ggaaagcatc cctctgttga cagttggtcc     660
atgcactgat ctatgaggat agcagagtat cactaggaat tacttattg tcttttttgc     720 cagtcgtttt tggttctctc ccgagtctct gggctgtcca gtctctggtt cctggccttc     780
cagacactgt cagttgtggg ttcccttttg tggtgttggc ctcaacttgg ccagtcattg     840
gttggccatt cccacaagtt ctacaccacc attaccctag catgtctcgc aggcaggaca     900
gattgtacgc ggaaggattt atggctgggt tatgtctcag tcccagggct ggaagccttg     960
cctggttaaa gaagacagct agttctgact cagtattccc tgttactagc agaattcact    1020
aggattaccc tcaccctcag ggcatttcca cagcactagg gttctgcatt gcctctccaa    1080
taccccctcc aattccagtc gccttcca gaactctcct cccccagcct gatccctatt     1140
gttcccaccc ccatccaccc ccagtccacc tacaaagctc tttcccttc caagaagat      1200 ccatgagttt ctctgtgtct gtggattgga gtatgatctg tggatttagc agctaatgtt    1260
cacttaccag tgagtacaca ccgttttgtct tttgggtctg ggttacctca ctcagggtgg    1320
attttggatt ttttttttg agtgctatcc atttgtctgc aaatgtcatg atgtcatttt    1380
ttttaacagc tgaggaattc tctcagaacc acatttttctt tatccattat tcagattgtt    1440 cccagttttct ggctattata aggctgctat gaacatggtt gaacaagtgt ccttgtggta    1500
tcggtacaca ggatgtggca tcctttgggt atatgcctag gagtggtatc gatgggtctc    1560
gaggtagatc aattcccgat tttctgagaa actgccatat ctgtttccaa agtggctgtg    1620
taagtttgcg ctcccaccag caacggagga gtgttctcct tactcctccc acattatcaa    1680
cagtgtgagc tgtcacttgt gttttgatc ttagcctttc tgcacaggtgt aagatggaat    1740 ctcaaagtag ctttgatttg catttccctg ctggctaagg atgttgaaca tttcctttaag    1800

```
tgtttctcag ccatttgaga tttatccatt gagaattctg tttagatctg aactccacct    1860
tctaattgga ttatttggtt tttaaaatat ccactttctc gagttcttaa tgggttttgg    1920
atattagccc tctgtcaaat gtggagttgg tgaagatctt ttcccattcg gtaggttttg    1980
tcctattgac agtgtcctt  gcttcacaga agcttttcag tttcatgagg tcccatttat    2040
tgattgttga atcttggtct tcttagtgcc tgtgctattg atgtctattc aggaagttgt    2100
ctcctgtgcc aatgcgttca aggctatttc ccactttctc ttctattagg ttcagtgtat    2160
ctcattttat gttgaggtct ttgatccact tagagttgag ttttgtgcag agtgatagat    2220
atggatctat ttgcattctt ctacatgcag atatccagta agaccagcat catttattgc    2280
ggatgctttt taaattttt  cgcttgtgta tttctggctt ctttataaaa atcaggtgtt    2340
cactgatttc attgatcagc caatgctttt ctgccgatac catgtggttt tattgctata    2400
gctctgaggt acagcttgag tcagggatgt gatgccctg  gacgtcctt  tattgtacag    2460 gagtatccta ggtttagcta tcctaggttt tttggttttc cacatggagt taagtattgt    2520
cctttcaagg tctatagaga attgcattgg gattttggtg gagattgtat tgcatttgta    2580
gatttggtag ggtggccatt tttactatgg taatcctacc                          2620
```